US006242221B1

(12) United States Patent
Robinson

(10) Patent No.: US 6,242,221 B1
(45) Date of Patent: Jun. 5, 2001

(54) GENOMIC POLYPHENOL OXIDASE GENE FRAGMENTS OF PLANTS

(75) Inventor: Simon Piers Robinson, Hawthorn (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

(21) Appl. No.: 09/129,030

(22) Filed: Aug. 4, 1998

Related U.S. Application Data

(63) Continuation of application No. PCT/AU97/00041, filed on Jan. 24, 1997.

(30) Foreign Application Priority Data

Feb. 5, 1996 (AU) .................................................. PN7856
Sep. 16, 1996 (AU) .................................................. PO2361

(51) Int. Cl.[7] .......................... C07H 21/04; C12N 15/63; C12N 15/64; C12P 19/34

(52) U.S. Cl. .................... 435/91.2; 435/91.4; 435/320.1; 536/24.3

(58) Field of Search ................................ 536/23.2, 23.6, 536/24.3; 435/69.1, 320.1, 419, 468, 469, 470, 91.2, 91.4; 800/278, 286, 298

(56) References Cited

U.S. PATENT DOCUMENTS 5,846,531 * 12/1998 Weiner et al. ...................... 424/94.4

FOREIGN PATENT DOCUMENTS

WO 94/03607 * 2/1994 (WO) .
9302195 2/1996 (WO) .
9637617 11/1996 (WO) .

OTHER PUBLICATIONS

Bachem CWB, et al. “Antisense expression of polyphenol oxidase genes inhibits enzymatic browning in potato tubers.” Bio/Tech. 12: 1101–1105, Nov. 1994.*

Stam M, et al. “The silence of genes in transgenic plants.” Ann. Bot. 79: 3–12, 1997.*

Koziel MG, et al. “Optimizing expression of transgenes with an emphasis on post–transcriptional events.” Plant Mol. Biol. 32: 393–405, 1996.*

Smith CJS et al. “Antisense RNA inhibition of polygalacturonase gene expression in transgenic tomatoes.” Nature 334: 724–726, Aug. 25, 1988.*

Ian B. Dry et al., (1994) “Molecular cloning and characteristic of grape berry polyphenol oxidase”, *Plant Molecular Biology*, 26: 495–502.

Jeffrey W. Cary et al., (1992) “Cloning and characterization of cDNAs coding for Vicia faba polyphenol oxidase”, *Plant Molecular Biology*, 20: 245–253.

Paul K. Boss et al., (1995) “An apple polyphenol oxidase cDNA is up–regulated in wounded tissues”, *Plant Molecular Biology*, 27: 429–433.

Peter W. Thygessen et al., (1995) “Polyphenol Oxidase in Potato”, *Plant Physiol*, 109: 525–531.

Tamar Shahar et al., (1992) “The Tomato 66.3–kD Polyphenoloxidase Gene: Molecular Identification and Development Expression”, *The Plant Cell*, 4: 135–147.

Sally M. Newman et al., (1993) “Organisation of the tomato polyphenol oxidase gene family”, *Plant Molecular Biology*, 21: 1035–1051.

Michelle D. Hunt et al., (1993) “cDNA cloning and expression of potato polyphenol oxidase”, *Plant Molecular Biology*, 21:59–68.

Richard W. Joy et al., (1995) “Cloning and Characterization of Polyphenol Oxidase cDNAs of *Phytolacca americana*”, *Plant Physiol*, 107: 1083–1089.

Geoffrey Hind et al., (1995) “Spinach Thylakoid Polyphenol Oxidase: Cloning, Characterization, and Relation to a Putative Protein Kinase”, *Biochemistry*, 34: 8157–8167.

Carolyn S. Bucheli et al., (1996) “Isolation of a full–length cDNA encoding polyphenol oxidase from sugarcane, a C4 grass”, *Molecular Biology*, 31: 1233–1238.

* cited by examiner

*Primary Examiner*—Amy J. Nelson
(74) *Attorney, Agent, or Firm*—John P. White; Cooper & Dunham LLP

(57) ABSTRACT

The present invention relates to the isolation of polyphenol oxidase (PPO) gene fragments from plants. In a first aspect of the present invention there is provided a method for preparing PPO gene fragments, which method includes providing a sample of plant tissue, a first primer in sense orientation having a sequence corresponding to a conserved region of a PPO gene, a second primer in antisense orientation having a sequence corresponding to a conserved region of a PPO gene; isolating genomic DNA from the plant tissue; and amplifying the genomic DNA using the first and second primers. Surprisingly, the applicant has found that PPO genes in plants lack introns and, therefore, fragments of PPO genes may be amplified directly from genomic DNA of a range of plants. The lack of introns means that the size of the fragments can be predicted and bands of the appropriate size can be selected for cloning.

21 Claims, 49 Drawing Sheets

```
ttt ctg gcg ttc cac aga tac tac ttg tac ttc tat gag aga atc ctg   48
Phe Leu Ala Phe His Arg Tyr Tyr Leu Tyr Phe Tyr Glu Arg Ile Leu

gga aaa ttg atc aac gac ccg tcg ctc gcc tcg act ttc tgg aac tgg   96
Gly Lys Leu Ile Asn Asp Pro Ser Leu Ala Ser Thr Phe Trp Asn Trp

gat gct ccg gct ggc atg caa ctc cca ggc atg ttt gcc aat cct aag   144
Asp Ala Pro Ala Gly Met Gln Leu Pro Gly Met Phe Ala Asn Pro Lys

tcg ccg ctc tac gac aag ttc cga aac gcc aac cat cag tcg ccg aag   192
Ser Pro Leu Tyr Asp Lys Phe Arg Asn Ala Asn His Gln Ser Pro Lys

ctc att gac ctc aat tac aat ctc aag gat gaa aac gtc tcc gac gaa   240
Leu Ile Asp Leu Asn Tyr Asn Leu Lys Asp Glu Asn Val Ser Asp Glu

act caa ata aac acc aac ctc aag atc atg tac agg caa atg gtg tcc   288
Thr Gln Ile Asn Thr Asn Leu Lys Ile Met Tyr Arg Gln Met Val Ser

aac gcc aag aac cct aag ctg ttc ttt gga aac cct tat agg gct ggg   336
Asn Ala Lys Asn Pro Lys Leu Phe Phe Gly Asn Pro Tyr Arg Ala Gly

gac gag cct agc ccc gga ggc gga gca ata gag act act cca cat gga   384
Asp Glu Pro Ser Pro Gly Gly Gly Ala Ile Glu Thr Thr Pro His Gly
```

FIG. 1A

```
ccg gtc cac att tgg acc ggt gac aac ata cag ccg aat ctt gag gac    432
Pro Val His Ile Trp Thr Gly Asp Asn Ile Gln Pro Asn Leu Glu Asp

atg gga aac ttc tac tct gct ggt aga gac cct ata ttt ttc tct cat    480
Met Gly Asn Phe Tyr Ser Ala Gly Arg Asp Pro Ile Phe Phe Ser His

cac tct aac gtt gac cgt ttg tgg agt gtg tgg aaa acc cta gga ggc    528
His Ser Asn Val Asp Arg Leu Trp Ser Val Trp Lys Thr Leu Gly Gly

aag aga gcg gat ttc act gac tct gat tgg ttg gat tcg ggg ttt ttg    576
Lys Arg Ala Asp Phe Thr Asp Ser Asp Trp Leu Asp Ser Gly Phe Leu

ttc tac gat gaa aa                                                 590
Phe Tyr Asp Glu
```

FIG. 1B

```
gat ccg acg ttt gcg ttg ccg ttt tgg aac tgg gac aac cct gct ggc     48
Asp Pro Thr Phe Ala Leu Pro Phe Trp Asn Trp Asp Asn Pro Ala Gly

atg cag ctg cct gcc ttg ttc gcc aat cct aaa tca ccg ctt tac gac     96
Met Gln Leu Pro Ala Leu Phe Ala Asn Pro Lys Ser Pro Leu Tyr Asp

cag ttc aga gcc gcc gct cat cag ccg ccg acc ctg atc gac ctc gat    144
Gln Phe Arg Ala Ala Ala His Gln Pro Pro Thr Leu Ile Asp Leu Asp

ttc aac ggt acg gag gac aac aca tca aac aca aca caa atc aac agc    192
Phe Asn Gly Thr Glu Asp Asn Thr Ser Asn Thr Thr Gln Ile Asn Ser

aac tta agc att atg tac cgt caa atg gta tct aac gcc aag aat gct    240
Asn Leu Ser Ile Met Tyr Arg Gln Met Val Ser Asn Ala Lys Asn Ala

cag ctc ttc ttc ggc aac cca tac cgg gct ggg gac gag cct gac ccc    288
Gln Leu Phe Phe Gly Asn Pro Tyr Arg Ala Gly Asp Glu Pro Asp Pro

ggt ggt ggc tcc att gag gga act cca cac ggg ccg gtt cac ttg tgg    336
Gly Gly Gly Ser Ile Glu Gly Thr Pro His Gly Pro Val His Leu Trp

acc ggt gac aat acg cag cct aac ttt gag gac atg gga aac ttc tac    384
Thr Gly Asp Asn Thr Gln Pro Asn Phe Glu Asp Met Gly Asn Phe Tyr
```

FIG. 2A

```
tcc gcc gga aga gat cct att ttc ttc tcg cac cac tcc aat gtt gat    432
Ser Ala Gly Arg Asp Pro Ile Phe Phe Ser His His Ser Asn Val Asp

agg atg tgg agt att tgg aag acc cta gct ccc aaa aac aaa gac atc    480
Arg Met Trp Ser Ile Trp Lys Thr Leu Ala Pro Lys Asn Lys Asp Ile

acc gac tcc gat tgg tta gac tcc ggc ttc ctg ttc tac gac gaa aa     527
Thr Asp Ser Asp Trp Leu Asp Ser Gly Phe Leu Phe Tyr Asp Glu
```

FIG. 2B

```
gat ccg acg ttt gcg ttg cca tat tgg aac tgg gac aat cca agc ggc   48
Asp Pro Thr Phe Ala Leu Pro Tyr Trp Asn Trp Asp Asn Pro Ser Gly

atg cgt ttg gct tat atg ttc gat gtc gaa ggt tct tcc ttg tac gat   96
Met Arg Leu Ala Tyr Met Phe Asp Val Glu Gly Ser Ser Leu Tyr Asp

gca aga cgt aat cca cat gtc cgt aat gga acc ata atc gat ctt ggt  144
Ala Arg Arg Asn Pro His Val Arg Asn Gly Thr Ile Ile Asp Leu Gly

ttt ttc ggt gat gaa gtc aaa act aat gaa cta cag atg ata act aac  192
Phe Phe Gly Asp Glu Val Lys Thr Asn Glu Leu Gln Met Ile Thr Asn

aac tta att tta atg tat cgt caa atg ata act aac gct cca tgc ccg  240
Asn Leu Ile Leu Met Tyr Arg Gln Met Ile Thr Asn Ala Pro Cys Pro

ctg ttg ttc ttc gga gag cct tat aga ttc gga tct aat ccc gaa cct  288
Leu Leu Phe Phe Gly Glu Pro Tyr Arg Phe Gly Ser Asn Pro Glu Pro
```

FIG. 3A

```
ggg atg gga acc att gaa aac atc cct cac aat ccg gtc cac att tgg     336
Gly Met Gly Thr Ile Glu Asn Ile Pro His Asn Pro Val His Ile Trp

act ggt act gtg cgg ggg acg gat ttg ggt aat ggt gcg aaa tca tac     384
Thr Gly Thr Val Arg Gly Thr Asp Leu Gly Asn Gly Ala Lys Ser Tyr

ggt gag gat atg ggt aat ttc tac tca act gct tta gac cca gtt ttt     432
Gly Glu Asp Met Gly Asn Phe Tyr Ser Thr Ala Leu Asp Pro Val Phe

ttc tgc cac cac gcc aat gtc gat cgc atg tgg                         465
Phe Cys His His Ala Asn Val Asp Arg Met Trp
```

FIG. 3B

```
gat ccg acg ttt ggt ttg cca tat tgg aac tgg gat cat cca aag ggc    48
Asp Pro Thr Phe Gly Leu Pro Tyr Trp Asn Trp Asp His Pro Lys Gly

atg cgt ttg cca cac atg ttt gat caa cca aat gtg tac cct gat ctt    96
Met Arg Leu Pro His Met Phe Asp Gln Pro Asn Val Tyr Pro Asp Leu

tac gat cca aga cgt aac caa gag cac cgc ggt tcg gta atc atg gac   144
Tyr Asp Pro Arg Arg Asn Gln Glu His Arg Gly Ser Val Ile Met Asp

ctt ggt cat ttt ggt caa gac gtg aaa gga act gac tta caa atg atg   192
Leu Gly His Phe Gly Gln Asp Val Lys Gly Thr Asp Leu Gln Met Met

agc aat aac ctt act cta atg tat cgt caa atg att acc aat tca ccg   240
Ser Asn Asn Leu Thr Leu Met Tyr Arg Gln Met Ile Thr Asn Ser Pro

tgt cca caa ctg ttt ttt ggt aag cca tat tgt acg gaa gtt gga ccc   288
Cys Pro Gln Leu Phe Phe Gly Lys Pro Tyr Cys Thr Glu Val Gly Pro
```

FIG. 4A

```
aaa cca ggg cag gga gct att gaa aac atc cct cat act cct gtc cac    336
Lys Pro Gly Gln Gly Ala Ile Glu Asn Ile Pro His Thr Pro Val His

att tgg gtt ggt agt aag cct aat gag aat aac tgt aaa aac ggt gaa    384
Ile Trp Val Gly Ser Lys Pro Asn Glu Asn Asn Cys Lys Asn Gly Glu

gat atg ggg aat ttc tat tca gct ggt aag gat cct gct ttc tat agt    432
Asp Met Gly Asn Phe Tyr Ser Ala Gly Lys Asp Pro Ala Phe Tyr Ser

cac cat cca aat gta gat cgc atg tgg aca ata tgg aag aca tta gga    480
His His Pro Asn Val Asp Arg Met Trp Thr Ile Trp Lys Thr Leu Gly

ggg aaa cgc gag gac atc aac aag cca gat tat ttg aac agt gag ttc    528
Gly Lys Arg Glu Asp Ile Asn Lys Pro Asp Tyr Leu Asn Ser Glu Phe

ttc ttc tat gac gaa aa                                             545
Phe Phe Tyr Asp Glu
```

FIG. 4B

```
gat ccg acg ttc gcg ttg ccc ttc tgg aac tgg gac gct ccg gac ggc   48
Asp Pro Thr Phe Ala Leu Pro Phe Trp Asn Trp Asp Ala Pro Asp Gly

atg tac atg cca gcc att ttc gag gac gac ccc gta ata aac cct ctc   96
Met Tyr Met Pro Ala Ile Phe Glu Asp Asp Pro Val Ile Asn Pro Leu

tac gat gcc aac cga aac gcc aag cac cgc gtg ccg ggg acg gtt tta   144
Tyr Asp Ala Asn Arg Asn Ala Lys His Arg Val Pro Gly Thr Val Leu

gac ctc aac tac cac ggc aag gac ggc aat acc aag gac gac aac aca   192
Asp Leu Asn Tyr His Gly Lys Asp Gly Asn Thr Lys Asp Asp Asn Thr

ata atc aat gat aat ctc cgc acc atg aac tcg aaa atg ctg tct att   240
Ile Ile Asn Asp Asn Leu Arg Thr Met Asn Ser Lys Met Leu Ser Ile

tca agc aca gac tgg tgt tca ttc ttc ggt cac cct tac cgg gct gga   288
Ser Ser Thr Asp Trp Cys Ser Phe Phe Gly His Pro Tyr Arg Ala Gly
```

FIG. 5A

```
tac caa cca aac ccc ggt gct ggc aat att gag agt atc cct cac aat   336
Tyr Gln Pro Asn Pro Gly Ala Gly Asn Ile Glu Ser Ile Pro His Asn

acc gtc cac aat tgg gct ggt acg gac tca agc ttg cca cca tac act   384
Thr Val His Asn Trp Ala Gly Thr Asp Ser Ser Leu Pro Pro Tyr Thr

ggg gag gac atg gga gtc ttc tac tct gcg ggt cga gat ccc atc ttc   432
Gly Glu Asp Met Gly Val Phe Tyr Ser Ala Gly Arg Asp Pro Ile Phe

ttc gca cac cat gcc aac gtg gac cgc atg tgg tac ttg tgg aag aac   480
Phe Ala His His Ala Asn Val Asp Arg Met Trp Tyr Leu Trp Lys Asn

aac ttt ggg gga cag gac ata gaa gac act gat tgg ttg gac agc tcg   528
Asn Phe Gly Gly Gln Asp Ile Glu Asp Thr Asp Trp Leu Asp Ser Ser

ttt ctg ttc tat gac gaa aa                                        548
Phe Leu Phe Tyr Asp Glu
```

FIG. 5B

```
ttt ttg ccg ttc cat cgt tac tac ctc tac ttc tat gag aag atc ttg   48
Phe Leu Pro Phe His Arg Tyr Tyr Leu Tyr Phe Tyr Glu Lys Ile Leu

ggc aag ttg att gga gat gag aca ttt gct ctc ccc ttc tgg aac tgg   96
Gly Lys Leu Ile Gly Asp Glu Thr Phe Ala Leu Pro Phe Trp Asn Trp

gat gca ccg ggt gga atg cca atg ccg tcc atg tac gcc aaa cca tcg  144
Asp Ala Pro Gly Gly Met Pro Met Pro Ser Met Tyr Ala Lys Pro Ser

tcg ccg ctc tac gac gag ctg aga gac gcc aag cac cag ccg ccg acg  192
Ser Pro Leu Tyr Asp Glu Leu Arg Asp Ala Lys His Gln Pro Pro Thr

ctg gtg gat ctg gac tac aac ttc cag gat ccc acc aac acc gac aag  240
Leu Val Asp Leu Asp Tyr Asn Phe Gln Asp Pro Thr Asn Thr Asp Lys

cag cag ata gcc agc aac ctc tcc atc atg tac cgg cag gtg gtg tcg  288
Gln Gln Ile Ala Ser Asn Leu Ser Ile Met Tyr Arg Gln Val Val Ser

aat ggc aag acg gcg cag ttg ttc atg ggt gcg gcg tac cgg gcc ggc  336
Asn Gly Lys Thr Ala Gln Leu Phe Met Gly Ala Ala Tyr Arg Ala Gly
```

FIG. 6A

```
ggg gag ccg gac ccc ggt gcc ggg tcg cta gag aac gtg ccg cat ggg    384
Gly Glu Pro Asp Pro Gly Ala Gly Ser Leu Glu Asn Val Pro His Gly

ccg gtc cat atc tgg acc ggt gac cgg act cag ccc aac acg gag aac    432
Pro Val His Ile Trp Thr Gly Asp Arg Thr Gln Pro Asn Thr Glu Asn

atg ggg aac ttc tac tcg gcg gca agg gac ccg atc ttc ttc gcc cac    480
Met Gly Asn Phe Tyr Ser Ala Ala Arg Asp Pro Ile Phe Phe Ala His

cac tcg aac gtc gac cgg atg tgg agc gtg tgg aag acc ctg gga ggg    528
His Ser Asn Val Asp Arg Met Trp Ser Val Trp Lys Thr Leu Gly Gly

aag agg aag gac ttc act gac cca gat tgg ctc aac tcg ggc ttc ctt    576
Lys Arg Lys Asp Phe Thr Asp Pro Asp Trp Leu Asn Ser Gly Phe Leu

ttc tac gac gaa aa                                                 590
Phe Tyr Asp Glu
```

FIG. 6B ttc ctg ccg ttt cac cgt ttc tac ctc tac ttc tat gag aag atc ttg 48
Phe Leu Pro Phe His Arg Phe Tyr Leu Tyr Phe Tyr Glu Lys Ile Leu ggc aag ttg att gga gat gag aca ttt gct ctc ccc ttc tgg aac tgg 96
Gly Lys Leu Ile Gly Asp Glu Thr Phe Ala Leu Pro Phe Trp Asn Trp gac gca ccg gac gga atg cca atg ccg tcc atg tac gcc aat tct tcg 144
Asp Ala Pro Asp Gly Met Pro Met Pro Ser Met Tyr Ala Asn Ser Ser gcg ccg ttc tac gac aag ctg aga gat gcc aag cac cag ccg ccg acg 192
Ala Pro Phe Tyr Asp Lys Leu Arg Asp Ala Lys His Gln Pro Pro Thr ctt gtg gat ttg gac tac aac ttc caa gat ccc acc aac acc gat atg 240
Leu Val Asp Leu Asp Tyr Asn Phe Gln Asp Pro Thr Asn Thr Asp Met cag cag ata tcc agc aac ctg tcc gtc atg tac cag cag gtg gtg tcg 288
Gln Gln Ile Ser Ser Asn Leu Ser Val Met Tyr Gln Gln Val Val Ser

FIG. 7A

```
aat gcc aag acg gcg gag ttg ttc atg ggt gcg gcg tac cgg gcc gga    336
Asn Ala Lys Thr Ala Glu Leu Phe Met Gly Ala Ala Tyr Arg Ala Gly

ggg gag ccg gac tcc ggt gcc ggg tcg cta gag aac gtg ccg cat ggg    384
Gly Glu Pro Asp Ser Gly Ala Gly Ser Leu Glu Asn Val Pro His Gly

ccg atc cat atc tgg acc ggt gac cgg act caa ccc aac ccg gag aac    432
Pro Ile His Ile Trp Thr Gly Asp Arg Thr Gln Pro Asn Pro Glu Asn

atg ggg aac ttc tac tcg gcg gga agg gac ccc atc ttc ttc gcc cac    480
Met Gly Asn Phe Tyr Ser Ala Gly Arg Asp Pro Ile Phe Phe Ala His

cac tcg aac gtc gac cgg atg tgg gac gtg tgg aag acc ctg gga ggg    528
His Ser Asn Val Asp Arg Met Trp Asp Val Trp Lys Thr Leu Gly Gly

aag agg aag gac ttc act gac gcg gat tgg ctc aac gcg ggc ttc ctc    576
Lys Arg Lys Asp Phe Thr Asp Ala Asp Trp Leu Asn Ala Gly Phe Leu

ttc tac gat gag aa                                                 590
Phe Tyr Asp Glu
```

FIG. 7B

```
gat ccg acg ttt gct ttg ccg ttc tgg aac tgg gac gcg ccg gcc ggc    48
Asp Pro Thr Phe Ala Leu Pro Phe Trp Asn Trp Asp Ala Pro Ala Gly

atg caa ctg cct gcc ttg tac gcc aac ccg gac tct ccc ctc tac gac    96
Met Gln Leu Pro Ala Leu Tyr Ala Asn Pro Asp Ser Pro Leu Tyr Asp

gag ctc cga gcc gcc acc cac cag ccg ccg gca ctc ctc gat ctc gaa   144
Glu Leu Arg Ala Ala Thr His Gln Pro Pro Ala Leu Leu Asp Leu Glu

ttc aac ggc acg gac gag aaa gtc aac aga gaa gct caa gtc aac tcc   192
Phe Asn Gly Thr Asp Glu Lys Val Asn Arg Glu Ala Gln Val Asn Ser

aat ctc aag atc atg tac agg cag atg gtg tcc aac gcc aag aaa ccg   240
Asn Leu Lys Ile Met Tyr Arg Gln Met Val Ser Asn Ala Lys Lys Pro

ctg ttg ttc ttt ggc tgg cct tat agg gct ggg act gaa gcg gac ccc   288
Leu Leu Phe Phe Gly Trp Pro Tyr Arg Ala Gly Thr Glu Ala Asp Pro

gga ccc ggt tca gtt gag aca act ccg cac ggg ccg gtt cat tta tgg   336
Gly Pro Gly Ser Val Glu Thr Thr Pro His Gly Pro Val His Leu Trp

acg gga gat aac acc cag cca aac ttt gag aac atg ggg aat ttt tat   384
Thr Gly Asp Asn Thr Gln Pro Asn Phe Glu Asn Met Gly Asn Phe Tyr

tcg gca gcc agg gat cct ata ttt ttt tcg cac cac tcc aac gtc gat   432
Ser Ala Ala Arg Asp Pro Ile Phe Phe Ser His His Ser Asn Val Asp

cgc atg tgg                                                       441
Arg Met Trp
```

FIG. 8

```
gat ccg acg ttc gct ttg ccc ttc tgg aac tgg gac gct cct gac ggc    48
Asp Pro Thr Phe Ala Leu Pro Phe Trp Asn Trp Asp Ala Pro Asp Gly

atg tac atg cca gcc att ttc gag gac gac ccc gta tta aac cct ctc    96
Met Tyr Met Pro Ala Ile Phe Glu Asp Asp Pro Val Leu Asn Pro Leu

tac gat gcc aac cga aac gcc aag cac cgt gtg ccg ggg acg gtt tta    144
Tyr Asp Ala Asn Arg Asn Ala Lys His Arg Val Pro Gly Thr Val Leu

gac ctc aac tac cac ggc aag gac gac aat acc aag gac gac gac aca    192
Asp Leu Asn Tyr His Gly Lys Asp Asp Asn Thr Lys Asp Asp Asp Thr

ata atc cgg cat aat ctc gtc acc atg aac tcg caa atg ctg tct att    240
Ile Ile Arg His Asn Leu Val Thr Met Asn Ser Gln Met Leu Ser Ile

tca agc aca gac tgg tgc tca ttc ttc ggt cat cct tac cgc gct gga    288
Ser Ser Thr Asp Trp Cys Ser Phe Phe Gly His Pro Tyr Arg Ala Gly
```

FIG. 9A

```
tac caa cca aac ccc ggt gct ggc aat att gag aaa atc cct cac agt    336
Tyr Gln Pro Asn Pro Gly Ala Gly Asn Ile Glu Lys Ile Pro His Ser

acc gtc cac aat tgg act ggt acg gac tca agt ttg cca cca aac act    384
Thr Val His Asn Trp Thr Gly Thr Asp Ser Ser Leu Pro Pro Asn Thr

ggg gag gac atg gga gtt tta tac tct gcg ggt aga gat ccc att ttt    432
Gly Glu Asp Met Gly Val Leu Tyr Ser Ala Gly Arg Asp Pro Ile Phe

ttc gca cac cat gcc aac gtg gac cgc atg tgg tac ttg tgg aag aac    480
Phe Ala His His Ala Asn Val Asp Arg Met Trp Tyr Leu Trp Lys Asn

aac ttt ggg gga cag gac ata gaa gac act gat tgg ctt gac agc tcg    528
Asn Phe Gly Gly Gln Asp Ile Glu Asp Thr Asp Trp Leu Asp Ser Ser

ttt ctg ttc tac gac gaa aa                                         548
Phe Leu Phe Tyr Asp Glu
```

FIG. 9B

```
gat ccg acg ttt gcg ttg ccc ttt tgg aac tgg gat gct cca gaa ggg    48
Asp Pro Thr Phe Ala Leu Pro Phe Trp Asn Trp Asp Ala Pro Glu Gly

atg tac atg cca acc ata ttt gag gag gat ggt gta att aac cct ctc    96
Met Tyr Met Pro Thr Ile Phe Glu Glu Asp Gly Val Ile Asn Pro Leu

tat gat ccc tac cga aat gac aag cac cgg cgt cca ggg aca atc gtg   144
Tyr Asp Pro Tyr Arg Asn Asp Lys His Arg Arg Pro Gly Thr Ile Val

gac ctc aac tac ggg cta ggc atg gac aac aac acc cga gac act gac   192
Asp Leu Asn Tyr Gly Leu Gly Met Asp Asn Asn Thr Arg Asp Thr Asp

aca ata gag aat tat aat ctc ttc acc atg cac aac aaa atg ttg agt   240
Thr Ile Glu Asn Tyr Asn Leu Phe Thr Met His Asn Lys Met Leu Ser

ggt gct cgc tgg gac tgg tgc tta ttc ttt ggc cat cct tac agg gca   288
Gly Ala Arg Trp Asp Trp Cys Leu Phe Phe Gly His Pro Tyr Arg Ala

ggg gac aac cca aat cca gga gcc ggc aac atc gag ctt gtt ccc cat   336
Gly Asp Asn Pro Asn Pro Gly Ala Gly Asn Ile Glu Leu Val Pro His

aac acc gtc cac gat tgg act ggc act act caa gac tca acc cag ggt   384
Asn Thr Val His Asp Trp Thr Gly Thr Thr Gln Asp Ser Thr Gln Gly

ggg gtg gac atg ggg ata ttc tac tct gca ggt aga gat cca gtg ttt   432
Gly Val Asp Met Gly Ile Phe Tyr Ser Ala Gly Arg Asp Pro Val Phe

tac gct cac cat gcc aac gtc gat cgc atg tgg                       465
Tyr Ala His His Ala Asn Val Asp Arg Met Trp
```

FIG. 10

```
gat ccg acg ttt gct ttg ccg ttt tgg aac tac gac gcg cca gct ggc    48
Asp Pro Thr Phe Ala Leu Pro Phe Trp Asn Tyr Asp Ala Pro Ala Gly

atg caa atc cct gcc ttg tac act aac ccg gac tct cca ctt tac gac    96
Met Gln Ile Pro Ala Leu Tyr Thr Asn Pro Asp Ser Pro Leu Tyr Asp

aag ttc cgc gct gcc agc cat cag ccg ccg act ctc atc gat ctt gac   144
Lys Phe Arg Ala Ala Ser His Gln Pro Pro Thr Leu Ile Asp Leu Asp

ttc aac ggc acg gac gaa aca att tcc aac gat gct cga atc gac gcc   192
Phe Asn Gly Thr Asp Glu Thr Ile Ser Asn Asp Ala Arg Ile Asp Ala

aac ctc aaa ctc atg tat agg cag atg att tcc aac gcc aag aaa cag   240
Asn Leu Lys Leu Met Tyr Arg Gln Met Ile Ser Asn Ala Lys Lys Gln

ctg ttg ttc ttt ggt gcg ccc ttg agg gct ggc act gaa cca gat cca   288
Leu Leu Phe Phe Gly Ala Pro Leu Arg Ala Gly Thr Glu Pro Asp Pro
```

FIG. 11A

```
ggg cag ggt tca atc gaa acg gcc cca cat ggt ccg gtt cat tta tgg    336
Gly Gln Gly Ser Ile Glu Thr Ala Pro His Gly Pro Val His Leu Trp

acc gga gat aac acg caa cct aat att gaa gac atg ggg aat ttt tac    384
Thr Gly Asp Asn Thr Gln Pro Asn Ile Glu Asp Met Gly Asn Phe Tyr

tcc gct gga agg gat cca ata ttt ttt gcg cac cat tcg aat gtg gat    432
Ser Ala Gly Arg Asp Pro Ile Phe Phe Ala His His Ser Asn Val Asp

cga atg tgg aat att tgg aaa agt tta ggg act aaa gat aaa gat att    480
Arg Met Trp Asn Ile Trp Lys Ser Leu Gly Thr Lys Asp Lys Asp Ile

aac gat ccg gat tgg ttg gat tcg ggg ttc ttg ttc tac gat gaa aa     527
Asn Asp Pro Asp Trp Leu Asp Ser Gly Phe Leu Phe Tyr Asp Glu
```

FIG. 11B

```
ctg cat tgt gcg tat tgc aat ggt gcc tac gtc caa cca ggc tct gat    48
Leu His Cys Ala Tyr Cys Asn Gly Ala Tyr Val Gln Pro Gly Ser Asp

caa gaa att tca gtc cat tac tcg tgg tta ttc ttc cct ttt cat aga    96
Gln Glu Ile Ser Val His Tyr Ser Trp Leu Phe Phe Pro Phe His Arg

tgg tat ttg tac ttc tat gaa gga atc ttg gga aag cta ata ggc gat   144
Trp Tyr Leu Tyr Phe Tyr Glu Gly Ile Leu Gly Lys Leu Ile Gly Asp

ccc agt ttt gga ctg ccc ttt tgg aac tgg gac aac att ggt ggc atg   192
Pro Ser Phe Gly Leu Pro Phe Trp Asn Trp Asp Asn Ile Gly Gly Met

acc ata ccg tcc ata ttt atg gac caa tcg tca gca ttg tat aac gaa   240
Thr Ile Pro Ser Ile Phe Met Asp Gln Ser Ser Ala Leu Tyr Asn Glu

aat cgt aac caa agt cat ctg cca cca acg gtc gtg gac ttg ggg tat   288
Asn Arg Asn Gln Ser His Leu Pro Pro Thr Val Val Asp Leu Gly Tyr

aat ggt acg gat aga gat gca aca tgc aca gaa agg ata gaa aac aat   336
Asn Gly Thr Asp Arg Asp Ala Thr Cys Thr Glu Arg Ile Glu Asn Asn
```

FIG. 12A

```
ttg gcg atc atg tac cgt caa atg gtc tct aat gcc acc act ggc aga    384
Leu Ala Ile Met Tyr Arg Gln Met Val Ser Asn Ala Thr Thr Gly Arg

gat ttc ttt gga aag gaa tac cgg gcc ggc gat gag ccc aat gcc ttt    432
\Asp Phe Phe Gly Lys Glu Tyr Arg Ala Gly Asp Glu Pro Asn Ala Phe

gct ggc gca ggg tcc atc gag gcc agt ccc cat att cca ctc cac agg    480
Ala Gly Ala Gly Ser Ile Glu Ala Ser Pro His Ile Pro Leu His Arg

tgg gtc ggc gat cca agg caa cca aat ggt gaa gat ttg ggt aat ttc    528
Trp Val Gly Asp Pro Arg Gln Pro Asn Gly Glu Asp Leu Gly Asn Phe

tac tca gct gga aga gat gtt ctg ttc tat agc cat cat gca aat gtg    576
Tyr Ser Ala Gly Arg Asp Val Leu Phe Tyr Ser His His Ala Asn Val

gac cgg atg tgg aca att tgg caa caa ttg gga ggt aaa agg aag gag    624
Asp Arg Met Trp Thr Ile Trp Gln Gln Leu Gly Gly Lys Arg Lys Glu

gtc ccc gat cca gat tgg ctg aat tct tcc ttc att ttc tac gac gaa    672
Val Pro Asp Pro Asp Trp Leu Asn Ser Ser Phe Ile Phe Tyr Asp Glu

aa                                                                 674
```

FIG. 12B

```
tg cat tgt gcg tat tgc aac ggt gcc tac atc caa tca ggc tct gat      47
   His Cys Ala Tyr Cys Asn Gly Ala Tyr Ile Gln Ser Gly Ser Asp

caa gaa att caa gtc cat aac tcg tgg cta ttc ttt cct ttt cat aga     95
Gln Glu Ile Gln Val His Asn Ser Trp Leu Phe Phe Pro Phe His Arg

tgg tat ttg tac ttc tat gaa aga atc ttg gga aag cta ata ggc gat    143
Trp Tyr Leu Tyr Phe Tyr Glu Arg Ile Leu Gly Lys Leu Ile Gly Asp

ccc agt ttt gga ctg ccc ttt tgg aac tgg gac aac att ggt ggt atg    191
Pro Ser Phe Gly Leu Pro Phe Trp Asn Trp Asp Asn Ile Gly Gly Met

acc cta ccg tcc ata ttt cag gac caa tcg tca gca ctg tat aac caa    239
Thr Leu Pro Ser Ile Phe Gln Asp Gln Ser Ser Ala Leu Tyr Asn Gln

aat cgt aac caa agt cat ctg cca cca aca gtc gtg gac ttg ggg tat    287
Asn Arg Asn Gln Ser His Leu Pro Pro Thr Val Val Asp Leu Gly Tyr

aat ggt acg gat aca gat gca aca gac ata gaa agg ata aaa aac aat    335
Asn Gly Thr Asp Thr Asp Ala Thr Asp Ile Glu Arg Ile Lys Asn Asn
```

FIG. 13A

```
ttg gca atc atg tac cgt caa atg gtc act aat tcc acc act gcc aaa    383
Leu Ala Ile Met Tyr Arg Gln Met Val Thr Asn Ser Thr Thr Ala Lys

gat ttc ttt gga aag gaa tac cgg gcc ggc gat gcg ccc agc ccg ggt    431
Asp Phe Phe Gly Lys Glu Tyr Arg Ala Gly Asp Ala Pro Ser Pro Gly

gca ggg tcc atc gag gcc att ccc cat atc cca atc cac agg tgg gtc    479
Ala Gly Ser Ile Glu Ala Ile Pro His Ile Pro Ile His Arg Trp Val

ggc gat cca agg cag cca aat ggt gaa gat atg ggt aat ttc tac tca    527
Gly Asp Pro Arg Gln Pro Asn Gly Glu Asp Met Gly Asn Phe Tyr Ser

gct gga aga gat att gtg ttc tat agc cat cat gca aat gtg gac cgg    575
Ala Gly Arg Asp Ile Val Phe Tyr Ser His His Ala Asn Val Asp Arg

atg tgg aca att tgg cag caa ttg gga ggt aaa agg aag gag gtc ccc    623
Met Trp Thr Ile Trp Gln Gln Leu Gly Gly Lys Arg Lys Glu Val Pro

gat cca gat tgg ctg aat tct tcc ttc att ttc tac gat gaa aa         667
Asp Pro Asp Trp Leu Asn Ser Ser Phe Ile Phe Tyr Asp Glu
```

FIG. 13B

```
cat tgc gcg tat tgc gac ggc gcg tac gac caa gtc ggc ttc ccc aac    48
His Cys Ala Tyr Cys Asp Gly Ala Tyr Asp Gln Val Gly Phe Pro Asn

ctc gag ctc caa atc cat caa tgc tgg ctt ttc ttc ccc ttc cat cgt    96
Leu Glu Leu Gln Ile His Gln Cys Trp Leu Phe Phe Pro Phe His Arg

tac tac cta tac ttc cac gaa aga atc ttg gcc aaa ctc ata gac gat    144
Tyr Tyr Leu Tyr Phe His Glu Arg Ile Leu Ala Lys Leu Ile Asp Asp

ccg acg ttc gcg ttg ccg ttt tgg aac tgg gac gcg cca gct ggc atg    192
Pro Thr Phe Ala Leu Pro Phe Trp Asn Trp Asp Ala Pro Ala Gly Met

caa ctc cct gcc ttg ttc gct aac ccg gac tct ccg ctt tac gac gag    240
Gln Leu Pro Ala Leu Phe Ala Asn Pro Asp Ser Pro Leu Tyr Asp Glu

ctt cgc gct gcc agc cat cag ccg ccg act ctc atc gat ctt gac ttc    288
Leu Arg Ala Ala Ser His Gln Pro Pro Thr Leu Ile Asp Leu Asp Phe
```

FIG. 14A

```
aac ggc acg gat gaa aca atg tcc aac gat gct caa atc gaa gcc aac    336
Asn Gly Thr Asp Glu Thr Met Ser Asn Asp Ala Gln Ile Glu Ala Asn

ctc aaa att atg tat agg cag atg gtt tcc aac tcc aag aaa ccg ctg    384
Leu Lys Ile Met Tyr Arg Gln Met Val Ser Asn Ser Lys Lys Pro Leu

ttg ttc ttt ggt tcg ccc tac agg gct ggc act gaa cca gat cca ggg    432
Leu Phe Phe Gly Ser Pro Tyr Arg Ala Gly Thr Glu Pro Asp Pro Gly

ggc ggt tca atc gaa acg acc cca cat ggt ccg gtt cat tta tgg acc    480
Gly Gly Ser Ile Glu Thr Thr Pro His Gly Pro Val His Leu Trp Thr

gga gat aac acg caa cct aat ttt gaa gac atg ggg aat ttt tac tcc    528
Gly Asp Asn Thr Gln Pro Asn Phe Glu Asp Met Gly Asn Phe Tyr Ser

gct gga agg gat cca ata ttt ttt tcg cac cat tcg aat ata gat cga    576
Ala Gly Arg Asp Pro Ile Phe Phe Ser His His Ser Asn Ile Asp Arg

atg tgg aat att                                                    588
Met Trp Asn Ile
```

FIG. 14B

```
ctg cat tgt gcg tat tgc gat ggg gca tac gat caa gtc ggt ttc cct    48
Leu His Cys Ala Tyr Cys Asp Gly Ala Tyr Asp Gln Val Gly Phe Pro

gat ctc gag ctt caa gtc cat ggc tca tgg ttg ttc tta cct ttc cac    96
Asp Leu Glu Leu Gln Val His Gly Ser Trp Leu Phe Leu Pro Phe His

cgc tat tac tta tac ttc ttc gac aaa att tgt ggc gga tta atc gat   144
Arg Tyr Tyr Leu Tyr Phe Phe Asp Lys Ile Cys Gly Gly Leu Ile Asp

gat cca aat ttc gca atc cct ttt tgg aac tgg gat gca cct gat ggc   192
Asp Pro Asn Phe Ala Ile Pro Phe Trp Asn Trp Asp Ala Pro Asp Gly

atg aag atc cct gat att tac acg aat aag aaa tct ccg ttg tac gat   240
Met Lys Ile Pro Asp Ile Tyr Thr Asn Lys Lys Ser Pro Leu Tyr Asp

gct ctt cgt gat gcg aag cat caa gca ccg tct ctg att gat ctt gac   288
Ala Leu Arg Asp Ala Lys His Gln Ala Pro Ser Leu Ile Asp Leu Asp
```

FIG. 15A

```
tac aat ggt gac gat gaa aat ctt agc cga tcg aga caa acc tcc aca    336
Tyr Asn Gly Asp Asp Glu Asn Leu Ser Arg Ser Arg Gln Thr Ser Thr

aat ctc aca att atg tac aga caa atg gtg tct agt tcc aag act gct    384
Asn Leu Thr Ile Met Tyr Arg Gln Met Val Ser Ser Ser Lys Thr Ala

agt ctt ttc atg ggt act cct tat cgt gca ggt gat gag gct agc cct    432
Ser Leu Phe Met Gly Thr Pro Tyr Arg Ala Gly Asp Glu Ala Ser Pro

ggc tct ggc tcg ctc gag agc ata cca cat ggc ccg gtt cat atc tgg    480
Gly Ser Gly Ser Leu Glu Ser Ile Pro His Gly Pro Val His Ile Trp

acc gga gat agg aac cag caa aat ggt gca gac atg ggt aac ttt tat    528
Thr Gly Asp Arg Asn Gln Gln Asn Gly Ala Asp Met Gly Asn Phe Tyr

tct gca gcc aga gac cct att ttt tat gca cat cat gcg aat atc gac    576
Ser Ala Ala Arg Asp Pro Ile Phe Tyr Ala His His Ala Asn Ile Asp

aga atg tgg tca gtt tgg aaa act cta gga gga aga agg aat gat ttt    624
Arg Met Trp Ser Val Trp Lys Thr Leu Gly Gly Arg Arg Asn Asp Phe

aca gat aaa gac tgg ctt gat ttt ttg ttc ttg ttc tac gac gag aa     671
Thr Asp Lys Asp Trp Leu Asp Phe Leu Phe Leu Phe Tyr Asp Glu
```

FIG. 15B

```
cat tgt gcg tac tgt aat gga gcc tat cac ctg tct cat cct ttc caa    48
His Cys Ala Tyr Cys Asn Gly Ala Tyr His Leu Ser His Pro Phe Gln

gac aca aaa ctc gac att cac agg tct tgg ttt ttc ttt ccc ttc cac    96
Asp Thr Lys Leu Asp Ile His Arg Ser Trp Phe Phe Phe Pro Phe His

cgt tgg tac att tac ttc ttt gaa cga att ttg ggg aac ttg att ggt    144
Arg Trp Tyr Ile Tyr Phe Phe Glu Arg Ile Leu Gly Asn Leu Ile Gly

gac cct aac ttt gct tta cca ttt tgg agt tgg gat tct ata gag ggc    192
Asp Pro Asn Phe Ala Leu Pro Phe Trp Ser Trp Asp Ser Ile Glu Gly

atg caa atg cca tcg tat ttc gca aac cct aac tcg tca gtt tat cac    240
Met Gln Met Pro Ser Tyr Phe Ala Asn Pro Asn Ser Ser Val Tyr His

aaa ctc cga cac cag aaa cac ctg cca ccc cac gtg gtg gac ctg aac    288
Lys Leu Arg His Gln Lys His Leu Pro Pro His Val Val Asp Leu Asn
```

FIG. 16A

```
tat gca agt gaa agt agc tat gtc cct tct cat caa caa gtt tcg tat    336
Tyr Ala Ser Glu Ser Ser Tyr Val Pro Ser His Gln Gln Val Ser Tyr

aat tta gcc acc atg tac aga caa atg gtg cta gca agt acc acg gaa    384
Asn Leu Ala Thr Met Tyr Arg Gln Met Val Leu Ala Ser Thr Thr Glu

ttg ttc atg gga ggc cct ttt cga cta ggg gat aac cct cgt cct ggt    432
Leu Phe Met Gly Gly Pro Phe Arg Leu Gly Asp Asn Pro Arg Pro Gly

cct ggt tct gtg gag gct gct cca cat aac acc gtt cat aca tgg gtt    480
Pro Gly Ser Val Glu Ala Ala Pro His Asn Thr Val His Thr Trp Val

ggt gga gcc gaa act cca aac cat gag gac atg gga acg ttt tac aca    528
Gly Gly Ala Glu Thr Pro Asn His Glu Asp Met Gly Thr Phe Tyr Thr

gct gct aga gac ccc att ttc tat ggt cat cac tcg aac ttg gat cga    576
Ala Ala Arg Asp Pro Ile Phe Tyr Gly His His Ser Asn Leu Asp Arg

atg tgg gcg ata tgg aaa aca ctg gga gaa gga aga aag gac tat agt    624
Met Trp Ala Ile Trp Lys Thr Leu Gly Glu Gly Arg Lys Asp Tyr Ser

gat gaa gat tgg tta gat tct gag ttt ttc ttc tat gac gaa aa         668
Asp Glu Asp Trp Leu Asp Ser Glu Phe Phe Phe Tyr Asp Glu
```

FIG. 16B

```
cac tgc gcg tat tgc aat ggt gcc tat cac caa gtt ggg ttt cct gac    48
His Cys Ala Tyr Cys Asn Gly Ala Tyr His Gln Val Gly Phe Pro Asp

ctt gac tta caa gtc cac aac tcc tgg cta ttc ttc cct tac cat cgt    96
Leu Asp Leu Gln Val His Asn Ser Trp Leu Phe Phe Pro Tyr His Arg

ttt tac ctt tat ttc tat gag aga ata ttg gga agc ttg att ggt gac   144
Phe Tyr Leu Tyr Phe Tyr Glu Arg Ile Leu Gly Ser Leu Ile Gly Asp

cca act ttt gct att cca ttt tgg aac tgg gac cac cct aaa ggt ggc   192
Pro Thr Phe Ala Ile Pro Phe Trp Asn Trp Asp His Pro Lys Gly Gly

atg acg atg cct tcc ctt ttc aca gat aaa aac tcc cct tta tat gac   240
Met Thr Met Pro Ser Leu Phe Thr Asp Lys Asn Ser Pro Leu Tyr Asp

cct cgc agg aat ctt tct cat caa cca cca act ctt ata gac cta gat   288
Pro Arg Arg Asn Leu Ser His Gln Pro Pro Thr Leu Ile Asp Leu Asp
```

FIG. 17A

```
tat aac aga aag gac gat aac aat ccc aac cag agt gaa agt gtt gct   336
Tyr Asn Arg Lys Asp Asp Asn Asn Pro Asn Gln Ser Glu Ser Val Ala

gac caa atc tct agt aac ctt act ata atg tat agg aac gtt gtc tcg   384
Asp Gln Ile Ser Ser Asn Leu Thr Ile Met Tyr Arg Asn Val Val Ser

ggt ggg aaa ctc ccg aag ctc ttc ctt gga agc cct tat cgt gct ggt   432
Gly Gly Lys Leu Pro Lys Leu Phe Leu Gly Ser Pro Tyr Arg Ala Gly

tca gat cct gac cct ggt gct ggg agc cta gag cat gtt cct cat att   480
Ser Asp Pro Asp Pro Gly Ala Gly Ser Leu Glu His Val Pro His Ile

cca gtt cac tct tgg tgt ggt gat ccc cga gag cct aac cgt gag gac   528
Pro Val His Ser Trp Cys Gly Asp Pro Arg Glu Pro Asn Arg Glu Asp

atg gga gtc ttc tat tca gct ggc aaa gac cct att ttt tat gct cac   576
Met Gly Val Phe Tyr Ser Ala Gly Lys Asp Pro Ile Phe Tyr Ala His

cat gcc aac gtg gat aga gtg tgg agc ata tgg aaa aca ata cca ggt   624
His Ala Asn Val Asp Arg Val Trp Ser Ile Trp Lys Thr Ile Pro Gly

ggg aaa aga agg gat ttc act gat cct gat tgg cta gaa tct agc ttt   672
Gly Lys Arg Arg Asp Phe Thr Asp Pro Asp Trp Leu Glu Ser Ser Phe

ttg ttc tac gat gaa aa                                            689
Leu Phe Tyr Asp Glu
```

FIG. 17B

```
cat tgt gcg tat tgt gac ggt gca tat cac caa gtt ggg ttc cct gac    48
His Cys Ala Tyr Cys Asp Gly Ala Tyr His Gln Val Gly Phe Pro Asp

ctt gat ctc caa gtc cac aac tct tgg ctc ttc ttt ccc ttc cat cga    96
Leu Asp Leu Gln Val His Asn Ser Trp Leu Phe Phe Pro Phe His Arg

tgg tat ctc tat ttc tac gaa aga atc ttg ggg agc ttg atc aac gac    144
Trp Tyr Leu Tyr Phe Tyr Glu Arg Ile Leu Gly Ser Leu Ile Asn Asp

cca acc ttc gcc ctc ccg ttt tgg aac tgg gat gct ccc aag ggc atg    192
Pro Thr Phe Ala Leu Pro Phe Trp Asn Trp Asp Ala Pro Lys Gly Met

caa ctt cct tcc att tat gca gac cct aaa tca cct ctc tat gat cct    240
Gln Leu Pro Ser Ile Tyr Ala Asp Pro Lys Ser Pro Leu Tyr Asp Pro

ctt cgc aat tct aat cat caa cct cca aca ctc gtt gac ctt gac ttc    288
Leu Arg Asn Ser Asn His Gln Pro Pro Thr Leu Val Asp Leu Asp Phe

gac att gag gat cct gat gcc gat gga aaa atc tcc tcc aac ctt acc    336
Asp Ile Glu Asp Pro Asp Ala Asp Gly Lys Ile Ser Ser Asn Leu Thr
```

FIG. 18A

```
ata atg tat agg caa gtt gtg tct aat ggg aaa act cct aga ctg ttc    384
Ile Met Tyr Arg Gln Val Val Ser Asn Gly Lys Thr Pro Arg Leu Phe

ctt gga aat gct tac cgt gct gga gat gaa ccc gac ccg ggt ggt gga    432
Leu Gly Asn Ala Tyr Arg Ala Gly Asp Glu Pro Asp Pro Gly Gly Gly

tcc gta gag aac gtt cca cat gga cct gtt cat gta tgg acc ggt gat    480
Ser Val Glu Asn Val Pro His Gly Pro Val His Val Trp Thr Gly Asp

atc gac cag ccc aac att gag aac atg gga act ttc tat tcg gct gca    528
Ile Asp Gln Pro Asn Ile Glu Asn Met Gly Thr Phe Tyr Ser Ala Ala

aga gac ccc att ttc ttc tct cat cat tcc aat ata gat agg atg tgg    576
Arg Asp ro Ile Phe Phe Ser His His Ser Asn Ile Asp Arg Met Trp

tcc ata tgg aaa aca ctt ggt ggg aaa aga agg gat ttc agt gac tcg    624
Ser Ile Trp Lys Thr Leu Gly Gly Lys Arg Arg Asp Phe Ser Asp Ser

gat tgg tta gaa tct ggg ctt ctc ttt tac gac gag aa                 662
Asp Trp Leu Glu Ser Gly Leu Leu Phe Tyr Asp Glu
```

FIG. 18B

```
ttg ccg ttt tgg aac tgg gac acc aag gac ggc atg acg ttc ccc gcc    48
Leu Pro Phe Trp Asn Trp Asp Thr Lys Asp Gly Met Thr Phe Pro Ala

atc ttc cag gat gcg gca tcc ccg ctg tac gac ccg aga cgc gac caa    96
Ile Phe Gln Asp Ala Ala Ser Pro Leu Tyr Asp Pro Arg Arg Asp Gln

cgc cac gtc aag gac ggc aag atc ctc gac ctc aag tac gcc tac acc   144
Arg His Val Lys Asp Gly Lys Ile Leu Asp Leu Lys Tyr Ala Tyr Thr

gaa aac act gca tcc gac agc gag atc ata cgg gag aac ctc tgc ttc   192
Glu Asn Thr Ala Ser Asp Ser Glu Ile Ile Arg Glu Asn Leu Cys Phe

ata cag aag acg ttc aag cac agc ctg tcg ctg gcg gaa ctg ttc atg   240
Ile Gln Lys Thr Phe Lys His Ser Leu Ser Leu Ala Glu Leu Phe Met

ggg gat ccc gtg cgc gcg ggg gag aag gag atc cag gag gct aat ggg   288
Gly Asp Pro Val Arg Ala Gly Glu Lys Glu Ile Gln Glu Ala Asn Gly

cag atg gaa gtc atc cac aat gcg gcg cac atg tgg gtc gga gag ccg   336
Gln Met Glu Val Ile His Asn Ala Ala His Met Trp Val Gly Glu Pro

gac gga tac aag gaa aac atg ggg gac ttc tcc acc gcc gcc cgc gat   384
Asp Gly Tyr Lys Glu Asn Met Gly Asp Phe Ser Thr Ala Ala Arg Asp

tct gtt ttc ttc tgc cac cat tgc aat gtc gac agc atg tgg           426
Ser Val Phe Phe Cys His His Cys Asn Val Asp Ser Met Trp
```

FIG. 19

```
ttg ccg ttt tgg aac tgg gac gca ccc ggc gga atg atg ctg ccg tcg    48
Leu Pro Phe Trp Asn Trp Asp Ala Pro Gly Gly Met Met Leu Pro Ser

atc tac gcc gac cct tcg tcg ccc ctc tac gac aaa ctt cgc gac gcc    96
Ile Tyr Ala Asp Pro Ser Ser Pro Leu Tyr Asp Lys Leu Arg Asp Ala

aag cac caa cca cct gtc ctt gtc gac ctc gac tac aat gga acc gac   144
Lys His Gln Pro Pro Val Leu Val Asp Leu Asp Tyr Asn Gly Thr Asp

cca acc ttc ccc gac gac cag caa atc gat cac aac ctc aag atc atg   192
Pro Thr Phe Pro Asp Asp Gln Gln Ile Asp His Asn Leu Lys Ile Met

tac cgc caa gtc ttc tcc aac ggc aag acg ccg ttg ctg ttc tta ggc   240
Tyr Arg Gln Val Phe Ser Asn Gly Lys Thr Pro Leu Leu Phe Leu Gly

tca gct tac cgt gcc ggt gac cag cct aac ccc ggc gcg gga tcc atc   288
Ser Ala Tyr Arg Ala Gly Asp Gln Pro Asn Pro Gly Ala Gly Ser Ile
```

FIG. 20A

```
gag aac atg ccg cac aac aac atg cac ttg tgg acc ggc gac cgc acc    336
Glu Asn Met Pro His Asn Asn Met His Leu Trp Thr Gly Asp Arg Thr

cag ccc aac ttc gag aac atg ggc acc ttc tac gcg gcg gcg cgc gac    384
Gln Pro Asn Phe Glu Asn Met Gly Thr Phe Tyr Ala Ala Ala Arg Asp

ccc atc ttc ttc gcc cac cac gcc aac atc gac cga atg tgg tac ctg    432
Pro Ile Phe Phe Ala His His Ala Asn Ile Asp Arg Met Trp Tyr Leu

tgg aag aag ctc agc agg aag cac cag gac ttc aat gac tcg gac tgg    480
Trp Lys Lys Leu Ser Arg Lys His Gln Asp Phe Asn Asp Ser Asp Trp

ctc aaa gct tcc ttc ctc ttc tat gac gaa aa                         512
Leu Lys Ala Ser Phe Leu Phe Tyr Asp Glu
```

FIG. 20B

```
ttg ccg tat tgg aat tgg gac gcg ccg gcc ggc atg tcg ttc ccg gcg    48
Leu Pro Tyr Trp Asn Trp Asp Ala Pro Ala Gly Met Ser Phe Pro Ala

atc tac gcc aac tgc agg ctg tcg tcg ctg tac gac cca agg cga aat    96
Ile Tyr Ala Asn Cys Arg Leu Ser Ser Leu Tyr Asp Pro Arg Arg Asn

cag gcg cac cag cca ccg ttc ccg ctc gac ctc aac tac agc gga acc   144
Gln Ala His Gln Pro Pro Phe Pro Leu Asp Leu Asn Tyr Ser Gly Thr

gac cca acc atc ccg gaa gat cag ctg atc gat cag aac ctc aag atc   192
Asp Pro Thr Ile Pro Glu Asp Gln Leu Ile Asp Gln Asn Leu Lys Ile

atg tac cgc cag gcc agt aat cac ata cac agt ttg aca caa act agg   240
Met Tyr Arg Gln Ala Ser Asn His Ile His Ser Leu Thr Gln Thr Arg

aat taattgaagt agctactgaa aaccgtagat agcaaactcc aaattaatta        293
Asn
```

FIG. 21A

```
gtcgacttta aattggatcg cgtgtctaat atgaacagta taa ttt atg atg tat   348
                                                Phe Met Met Tyr

cag atg att tcg ggg gct agg aag aaa gag ctg ttc atg gga cat ccg   396
Gln Met Ile Ser Gly Ala Arg Lys Lys Glu Leu Phe Met Gly His Pro

tac agc gcc ggc gac cag ccg aaa ccg ggg gcg ggc acc gtc gag ttc   444
Tyr Ser Ala Gly Asp Gln Pro Lys Pro Gly Ala Gly Thr Val Glu Phe

gtg ccg cac aac acc gtc cac aac tgg acc ggc gac ccg agg cag ccg   492
Val Pro His Asn Thr Val His Asn Trp Thr Gly Asp Pro Arg Gln Pro

aac ggc gag gac atg ggc atg ttc tac tcg gcg gcg cgc gac ccg gtg   540
Asn Gly Glu Asp Met Gly Met Phe Tyr Ser Ala Ala Arg Asp Pro Val

ttc ttc gcg cac cac ggc aac gtc gac cgc atg tgg tac att cgc cac   588
Phe Phe Ala His His Gly Asn Val Asp Arg Met Trp Tyr Ile Arg His

ggc ctc ttc ccc cgc gac acc gac ttc gcc gac ccc gac tgg ctc gac   636
Gly Leu Phe Pro Arg Asp Thr Asp Phe Ala Asp Pro Asp Trp Leu Asp

gcg acc ttc ctg ttg tac gac gaa aa                                662
Ala Thr Phe Leu Leu Tyr Asp Glu
```

FIG. 21B

```
ttg ccg ttt tgg aac tgg gat gca ccg gac gcg atg agc atg ccg gcg    48
Leu Pro Phe Trp Asn Trp Asp Ala Pro Asp Ala Met Ser Met Pro Ala

atg tac acc gac cag tcc tcg ccg ttg ttc gat ccc cgg cgg aac ggg    96
Met Tyr Thr Asp Gln Ser Ser Pro Leu Phe Asp Pro Arg Arg Asn Gly

cgg cac gtg ccg ccg aag ctg atc gat ctg gac tac aat ggg agg gag   144
Arg His Val Pro Pro Lys Leu Ile Asp Leu Asp Tyr Asn Gly Arg Glu

cca cgg ttc acc gac aac caa cag gtt gat caa aac cta cgt gtc atg   192
Pro Arg Phe Thr Asp Asn Gln Gln Val Asp Gln Asn Leu Arg Val Met

tac cgt cag gta tat gtg caa tgc gtg cat cga tgc agc gcg ttc gtc   240
Tyr Arg Gln Val Tyr Val Gln Cys Val His Arg Cys Ser Ala Phe Val

tct acg aaa ttt acc cac gta cgt gac cag aaa atg tac tg            287
Ser Thr Lys Phe Thr His Val Arg Asp Gln Lys Met Tyr
```

FIG. 22A

```
                                                            aaa cgt      287
                                                            Lys Arg

gca tgt caa att ggt ttt cag atg atc tcg ctg agt ccg acg ccg tcg      335
Ala Cys Gln Ile Gly Phe Gln Met Ile Ser Leu Ser Pro Thr Pro Ser

ctc ttc ttc ggc agc ccg tac cgc gcc ggc gac gac ccg aac cag ggg      383
Leu Phe Phe Gly Ser Pro Tyr Arg Ala Gly Asp Asp Pro Asn Gln Gly

cca ggt ccc gtt gag aac atc ccg cac ggg ccg gtg cac atc tgg tgc      431
Pro Gly Pro Val Glu Asn Ile Pro His Gly Pro Val His Ile Trp Cys

ggc gac ccg gag cag ccg gcc ggc gag gac atg ggc aac ttc tac tcg      479
Gly Asp Pro Glu Gln Pro Ala Gly Glu Asp Met Gly Asn Phe Tyr Ser

gcc ggc cgc gac cct ctc ttt tac gcg cac cac gcc aac atc gac cgc      527
Ala Gly Arg Asp Pro Leu Phe Tyr Ala His His Ala Asn Ile Asp Arg

atg tgg gcc gtc tgg aag gga ctc gac ccg cgt cgc cac acc gac ctc      575
Met Trp Ala Val Trp Lys Gly Leu Asp Pro Arg Arg His Thr Asp Leu

acc gac cca gac tgg ctc gac gcc tcc ttc ctc ttc tat gac gaa aa       622
Thr Asp Pro Asp Trp Leu Asp Ala Ser Phe Leu Phe Tyr Asp Glu
```

FIG. 22B

```
gat ccg acg ttc gct ttg cca tat tgg aat tgg gac cat cca aag ggt    48
Asp Pro Thr Phe Ala Leu Pro Tyr Trp Asn Trp Asp His Pro Lys Gly

atg cgt tta cct ccc atg ttc gat cgt gaa att act ccc ctt tat gat    96
Met Arg Leu Pro Pro Met Phe Asp Arg Glu Ile Thr Pro Leu Tyr Asp

gaa aga cgt aat cca cac gtc cgt aat gga acc ata atc gat ttt agt   144
Glu Arg Arg Asn Pro His Val Arg Asn Gly Thr Ile Ile Asp Phe Ser

tct tct aaa gac gaa gtt cct act gat gtt aaa cag acg gtg act aac   192
Ser Ser Lys Asp Glu Val Pro Thr Asp Val Lys Gln Thr Val Thr Asn

aac tta act gta atg tac cgt caa atg ata act aat gct gca tgc cct   240
Asn Leu Thr Val Met Tyr Arg Gln Met Ile Thr Asn Ala Ala Cys Pro

ttg cag ttc ttc ggt gct cgt tac gtt ctt ggg aat aat aat atg aat   288
Leu Gln Phe Phe Gly Ala Arg Tyr Val Leu Gly Asn Asn Asn Met Asn
```

FIG. 23A

```
gat cgg gga act att gaa aac agc cct cat act ccg gtc cac att tgg    336
Asp Arg Gly Thr Ile Glu Asn Ser Pro His Thr Pro Val His Ile Trp

gct ggt aca gaa caa ggt tca act ttt cct aat ggt gat acg tca tac    384
Ala Gly Thr Glu Gln Gly Ser Thr Phe Pro Asn Gly Asp Thr Ser Tyr

ggt gag gat atg ggc aat ttc tac tca gcc gct tta gac ccg gtt ttc    432
Gly Glu Asp Met Gly Asn Phe Tyr Ser Ala Ala Leu Asp Pro Val Phe

tat agc cac cac gcc aat gta gac cgt atg tgg aat ata tgg aaa gga    480
Tyr Ser His His Ala Asn Val Asp Arg Met Trp Asn Ile Trp Lys Gly

tta ggc ggg aaa aaa aag gat atc aca gac aca gat tgg ttg aac tcc    528
Leu Gly Gly Lys Lys Lys Asp Ile Thr Asp Thr Asp Trp Leu Asn Ser

gaa ttc ttt ttc tac gac gaa aa                                     551
Glu Phe Phe Phe Tyr Asp Glu
```

FIG. 23B

```
tg cac tgt gcg tat tgt aac ggt gct tat aga att ggt ggc aaa gag     47
His Cys Ala Tyr Cys Asn Gly Ala Tyr Arg Ile Gly Gly Lys Glu

tta caa gtt cat aat tct tgg ctt ttc ttc ccg ttc cat aga tgg tac    95
Leu Gln Val His Asn Ser Trp Leu Phe Phe Pro Phe His Arg Trp Tyr

ttg tac ttc cac gag aga atc gtg gga aaa ttc att gat gat cca act    143
Leu Tyr Phe His Glu Arg Ile Val Gly Lys Phe Ile Asp Asp Pro Thr

ttc gct tta cca tat tgg aat tgg gac cat cca aaa ggt atg cgt ttt    191
Phe Ala Leu Pro Tyr Trp Asn Trp Asp His Pro Lys Gly Met Arg Phe

cct gcc atg tat gat cgt gaa ggg act tcc ctt ttc gat gta aca cgt    239
Pro Ala Met Tyr Asp Arg Glu Gly Thr Ser Leu Phe Asp Val Thr Arg

gac caa agt cac cga aat gga gca gta atc gat ctt ggt ttt ttc ggc    287
Asp Gln Ser His Arg Asn Gly Ala Val Ile Asp Leu Gly Phe Phe Gly

aat gaa gtt gaa aca act caa ctc cag ttg atg agc aat aat tta aca    335
Asn Glu Val Glu Thr Thr Gln Leu Gln Leu Met Ser Asn Asn Leu Thr
```

FIG. 24A

```
cta atg tac cgt caa atg gta act aat gct cca tgt cct cgg atg ttc    383
Leu Met Tyr Arg Gln Met Val Thr Asn Ala Pro Cys Pro Arg Met Phe

ttt ggc ggg cct tat gat ctc ggg gtt aac act gaa ctc ccg gga act    431
Phe Gly Gly Pro Tyr Asp Leu Gly Val Asn Thr Glu Leu Pro Gly Thr

ata gaa aac atc cct cac ggt cct gtc cac atc tgg tct ggt aca gtg    479
Ile Glu Asn Ile Pro His Gly Pro Val His Ile Trp Ser Gly Thr Val

aga ggt tca act ttg ccc aat ggt gca ata tca aac ggt gag aat atg    527
Arg Gly Ser Thr Leu Pro Asn Gly Ala Ile Ser Asn Gly Glu Asn Met

ggt cat ttt tac tca gct ggt ttg gac ccg gtt ttc ttt tgc cat cac    575
Gly His Phe Tyr Ser Ala Gly Leu Asp Pro Val Phe Phe Cys His His

agc aat gtg gat cgg atg tgg agc gaa tgg aaa gcg aca gga ggg aaa    623
Ser Asn Val Asp Arg Met Trp Ser Glu Trp Lys Ala Thr Gly Gly Lys

aga acg gat atc aca cat aaa gat tgg ttg aac tcc gag ttc ttt ttc    671
Arg Thr Asp Ile Thr His Lys Asp Trp Leu Asn Ser Glu Phe Phe Phe

tat gac gaa aa                                                     682
Tyr Asp Glu
```

FIG. 24B

```
ttg ccg tat tgg aat tgg gac cat cca aaa ggt atg cgt tta cct ccc   48
Leu Pro Tyr Trp Asn Trp Asp His Pro Lys Gly Met Arg Leu Pro Pro

atg ttc gat cgt gaa act act ccc ctt tat gat gca aga cgt aat cca   96
Met Phe Asp Arg Glu Thr Thr Pro Leu Tyr Asp Ala Arg Arg Asn Pro

cat gtc cgt aat gga acc ata atc gat ttt agt tct cct aga gac gaa   144
His Val Arg Asn Gly Thr Ile Ile Asp Phe Ser Ser Pro Arg Asp Glu

gtt att act gat gtt gga caa acg gtg act aac aac tta act tta atg   192
Val Ile Thr Asp Val Gly Gln Thr Val Thr Asn Asn Leu Thr Leu Met

tac cgt tca atg ata act aat gct gca tgc cct ttg caa ttc ttt ggt   240
Tyr Arg Ser Met Ile Thr Asn Ala Ala Cys Pro Leu Gln Phe Phe Gly
```

FIG. 25A

```
gct cgt tac gtc ctt ggg aat aac gat tcc aaa ggt cag gga act att    288
Ala Arg Tyr Val Leu Gly Asn Asn Asp Ser Lys Gly Gln Gly Thr Ile

gaa aac atc cct cat act ccg gtc cac ata tgg gct ggt act gta aga    336
Glu Asn le Pro His Thr Pro Val His Ile Trp Ala Gly Thr Val Arg

aat acg gat ttg ggt ggt ggt aaa ctg tca tta ggt gaa gat atg ggt    384
Asn Thr Asp Leu Gly Gly Gly Lys Leu Ser Leu Gly Glu Asp Met Gly

aat ttc tac tca gcc gct tta gac ccg gtt ttc tat tgc cac cac gcc    432
Asn Phe Tyr Ser Ala Ala Leu Asp Pro Val Phe Tyr Cys His His Ala

aat gtg gac cga atg tgg aaa gta tgg aaa gga tta cgc ggg aaa aga    480
Asn Val Asp Arg Met Trp Lys Val Trp Lys Gly Leu Arg Gly Lys Arg

agg gat atc ata gat cca gat tgg ttg aac tct gaa ttc ttt ttc tac    528
Arg Asp Ile Ile Asp Pro Asp Trp Leu Asn Ser Glu Phe Phe Phe Tyr

gac gag aa                                                         536
Asp Glu
```

FIG. 25B

```
ttg ccg ttc tgg aat tgg gat cat cca aaa ggt atg cgt ata cct ccc    48
Leu Pro Phe Trp Asn Trp Asp His Pro Lys Gly Met Arg Ile Pro Pro

atg ttt gat cgt gag ggg tca tct ctt tac gat gat aaa cgt aac caa    96
Met Phe Asp Arg Glu Gly Ser Ser Leu Tyr Asp Asp Lys Arg Asn Gln

aac cat cgc aat gga act att att gat ctt ggt cat ttt ggt aag gaa    144
Asn His Arg Asn Gly Thr Ile Ile Asp Leu Gly His Phe Gly Lys Glu

gtt gac aca cct cag ctc cag ata atg act aat aat tta aca cta atg    192
Val Asp Thr Pro Gln Leu Gln Ile Met Thr Asn Asn Leu Thr Leu Met

tac cgt caa atg gtg act aat gct cct tgt ccg ccc caa ttc ttc ggt    240
Tyr Arg Gln Met Val Thr Asn Ala Pro Cys Pro Pro Gln Phe Phe Gly

gct gct tac cct ctg ggg act aaa cca agt ccg gga atg ggt act att    288
Ala Ala Tyr Pro Leu Gly Thr Lys Pro Ser Pro Gly Met Gly Thr Ile
```

FIG. 26A

```
gag aac atc cct cat acc ccg gtt cac atc tgg acc ggt gat aca cct    336
Glu Asn Ile Pro His Thr Pro Val His Ile Trp Thr Gly Asp Thr Pro

aga caa aaa aac ggt gaa aac atg ggt aat ttc tat tca gcc ggt tta    384
Arg Gln Lys Asn Gly Glu Asn Met Gly Asn Phe Tyr Ser Ala Gly Leu

gac ccg att ttt tac tgt cac cac gca aat gtg gac cgg atg tgg gat    432
Asp Pro Ile Phe Tyr Cys His His Ala Asn Val Asp Arg Met Trp Asp

gaa tgg aaa tta att ggc ggg aaa aga agg gat cta tca aat aaa gat    480
Glu Trp Lys Leu Ile Gly Gly Lys Arg Arg Asp Leu Ser Asn Lys Asp

tgg ttg aac tca gaa ttc ttt ttc tat gac gag aa                     515
Trp Leu Asn Ser Glu Phe Phe Phe Tyr Asp Glu
```

FIG. 26B

GENOMIC POLYPHENOL OXIDASE GENE FRAGMENTS OF PLANTS

CROSS REFERENCE TO RELATED APPLICATIONS

The present application is a continuation of International Patent Application No. PCT/AU97/00041 filed on Jan. 24, 1997 and designating United States, which claims Paris Convention priority from Australian Patent Application No. PO 7856 filed on Feb. 5, 1996, and from Australian Patent Application No. PO 2361 filed on Sep. 16, 1996.

STATEMENT REGARDING FEDERALLY SPONSORED RESEARCH OR DEVELOPMENT

Not Applicable

BACKGROUND OF THE INVENTION

1. Field of the invention

The present invention relates to the isolation of genes encoding polyphenol oxidase (PPO) from plants. More particularly, the present invention provides methods for obtaining genomic DNA encoding PPO enzymes and fragments of a wide range of plants, such as, for example, strawberry, tobacco, apricot, avocado, cherry, peach, pear, coffee, apple, lettuce, French bean, banana, rice, and potato. The present invention clearly extends to the isolated genomic DNAs encoding said PPO enzymes and fragments.

Browning of plant tissues often occurs following injury or damage and this generally results in spoilage of fruit and vegetables. Undesirable browning also occurs during processing of plant materials to produce food or other products. Steps are taken during transport, storage, and processing to prevent these browning reactions. Often this involves the use of chemicals such as sulphur dioxide but the use of these substances is likely to be restricted in the future due to concerns about their safety and consumer acceptance. For example, the US Food and Drug Administration banned the use of sulphite for most fresh fruit and vegetables in 1986. The production of fruit and vegetable varieties with an inherently low susceptibility to brown would remove the need for these chemical treatments.

It will be understood that browning in plants is predominantly catalysed by the enzyme PPO. PPO is localised in the plastids of plant cells whereas the phenolic substrates of the enzyme are stored in the plant cell vacuole. This compartmentation prevents the browning reaction from occurring unless the plant cells are damaged and the enzyme and its substrates are mixed.

It will be apparent from the preceding discussion that there is a need to develop methods for reducing the level of browning of plant tissues. One approach is to modulate the level of expression of PPO genes in plants. A prerequisite to achieving this objective by molecular means is the isolation of nucleic acid encoding PPO genes from a variety of plant sources.

2. Description of Related Art

The prior art includes International Application PCT/AU92/00356 to the present applicant which describes the cloning of PPO genes from grapevine, broad bean leaf, apple fruit and potato tuber. This application recognises that PPO levels in plants may be manipulated by increasing or decreasing expression of PPO gene. The application also identifies two conserved copper binding sites in PPO genes, designated CuA and CuB, and predicts that these regions are suitable for design of probes and primers to obtain other plant PPO genes. However, the method described in PCT/AU92/00356 suffers from the disadvantages that it is necessary to identify the appropriate stage of development of the target tissue, isolate mRNA or total RNA and synthesize cDNA. This in turn requires a relatively large amount of plant material.

SUMMARY OF THE INVENTION

This application is derived from International Patent Application No. PCT/AU97/00041 filed on Jan. 24, 1997, which claims Paris Convention priority from Australian Patent Application No. PO 7856 filed on Feb. 5, 1996, and from Australian Patent Application No. PO 2361 filed on Sep. 16, 1996, the entire contents of which are incorporated herein by way of reference.

Bibliographic details of the publications referred to in this specification by author are collected at the end of the description.

Sequence Identity Numbers (SEQ ID NOs.) for the nucleotide and amino acid sequences referred to in the specification appear after the claims.

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In work leading up to the present invention, the inventors sought to produce improved methods for isolating PPO-encoding nucleic acid molecules which are susceptible for use in modifying the expression of endogenous PPO genes in plants, to reduce browning and modify ripening and storage characteristics of plant tissues and organs.

It is an object of the present invention to overcome or at least alleviate one or more of the difficulties related to the prior art.

The inventors have cloned several PPO-encoding genomic DNAs from strawberry, tobacco, apricot, avocado, cherry, peach, pear, coffee, apple, lettuce, French bean, banana, rice, and potato and produced recombinant gene constructs comprising same for the expression of recombinant PPO polypeptides and nucleic acids capable of modifying the PPO content of plant tissues and cells when expressed therein.

Accordingly, a first aspect of the present invention provides a method for preparing nucleic acid encoding PPO, fragments and derivatives thereof, which method includes the steps of:

(a) providing:

(i) a sample of plant tissue, (ii) a first primer in sense orientation having a sequence corresponding to a conserved region of a PPO gene, (iii) a second primer in antisense orientation having a sequence corresponding to a conserved region of a PPO gene;

(b) isolating genomic DNA from said plant tissue; and (c) amplifying the genomic DNA using the first and second primers.

Preferably, the conserved region of a PPO gene is contained within or is in close proximity to a nucleotide sequence of a PPO gene that encodes the CuA or CuB region of a PPO polypeptide.

In a further aspect of the present invention, there is provided isolated nucleic acid comprising a nucleotide sequence which encodes PPO or a complementary nucleotide sequence thereto, or a fragment or derivative of said nucleic acid, wherein said nucleic acid os derived from a plant selected from the group consisting of strawberrry, tobacco, apricot, avocado, cherry, peach, pear, pineapple, tea, coffee, apple, lettuce, French bean, banana, rice, potato, parsnip, and wheat. This aspect of the invention clearly extends to any nucleic acid isolated using the inventive method described herein. Preferably, the nucleic acid comprises genomic DNA or an equivalent thereof which lacks introns.

A further aspect of the present invention provides a method for preparing a recombinant vector which includes nucleic acid comprising a nucleotide sequence encoding PPO or complementary thereto, or a fragment or derivative of said nucleic acid, wherein said nucleic acid is derived from a plant selected from the group consisting of strawberry, tobacco, apricot, avocado, cherry, peach, pear, pineapple, tea, coffee, apple, lettuce, French bean, banana, rice, potato, parsnip and wheat, and wherein said method includes:

(i) providing said nucleic acid and a vector; and (ii) reacting said nucleic acid and said vector to deploy the nucleic acid within the vector.

A further aspect of the present invention provides a recombinant vector capable of being replicated, transcribed and translated in a unicellular organism or a plant, wherein said vector includes isolated nucleic acid comprising a nucleotide sequence encoding PPO or a complementary nucleotide sequence thereto, or a fragment or derivative of said nucleic acid, wherein said nucleic acid is derived from a plant selected from the group consisting of strawberry, tobacco, apricot, avocado, cherry, peach, pear, pineapple, tea, coffee, apple, lettuce, French bean, banana, rice, potato, parsnip and wheat.

A further aspect of the present invention provides a method of decreasing the level of PPO activity in a plant tissue, which method includes:

(a) providing:

(i) nucleic acid encoding PPO of strawberry, tobacco, apricot, avocado, cherry, peach, pear, pineapple, tea, coffee, apple, lettuce, French bean, banana, rice, potato, parsnip or wheat, or nucleic acid antisense to said nucleic acid; and (ii) a plant sample; and (b) introducing said nucleic acid into said plant sample to produce a transgenic plant.

In a further aspect of the present invention there is provided a method of increasing the level of PPO activity in a plant tissue, which method includes:

(a) providing:

(i) nucleic acid encoding PPO of strawberry, tobacco, apricot, avocado, cherry, peach, pear, pineapple, tea, coffee, apple, lettuce, French bean, banana, rice, potato, parsnip or wheat, or a fragment of said nucleic acid; and a plant sample; and (b) introducing said nucleic acid into said plant sample to produce a transgenic plant.

In a further aspect of the present invention there is provided a transgenic plant, which plant contains nucleic acid capable of modifying expression of the normal PPO gene, such as, for example, nucleic acid encoding PPO or antisense thereto, wherein said nucleic acid is derived from a plant selected from the group consisting of strawberry, tobacco, apricot, avocado, cherry, peach, pear, pineapple, tea, coffee, apple, lettuce, French bean, banana, rice, potato, parsnip and wheat.

BRIEF DESCRIPTION OF THE DRAWINGS

FIGS. 1A–1B are a representation showing the nucleotide sequence of genomic DNA encoding PPO of strawberry contained in clone GSPO2 (above), and the derived protein sequence therefor (below), as set forth in SEQ ID NOS. 1 and 2, repectively.

FIGS. 2A–2B are a representation showing the nucleotide sequence of genomic DNA of strawberry contained in clone GSPO6 (above), and the derived protein sequence therefor (below), as set forth in SEQ ID NOS. 3 and 4, respectively.

FIGS. 3A–3B are a representation showing the nucleotide sequence of genomic DNA of tobacco contained in clone GTPO1 (above), and the derived protein sequence therefor (below), as set forth in SEQ ID NOS. 5 and 6, respectively.

FIGS. 4A–4B are a representation showing the nucleotide sequence of genomic DNA encoding PPO of tobacco contained in clone GTP03 (above), and the derived protein sequence therefor (below), as set forth in SEQ ID NOS. 7 and 8, respectively.

FIGS. 5A–5B are a representation showing the nucleotide sequence of genomic DNA encoding PPO of apricot contained in clone GAP03 (above), and the derived protein sequence therefor (below), as set forth in SEQ ID NOS. 9 and 10, respectively.

FIGS. 6A–6B are a representation showing the nucleotide sequence of genomic DNA encoding PPO of avocado contained in clone GAVPO1 (above), and the derived protein sequence therefor (below), as set forth in SEQ ID NOS. 11 and 12, respectively.

FIGS. 7A–7B are a representation showing the nucleotide sequence of genomic DNA encoding PPO of cherry contained in clone (above), and the derived protein sequence therefor (below), as set forth in SEQ ID NOS. 13 and 14, respectively.

FIG. 8 is a representation showing the nucleotide sequence of genomic DNA encoding PPO of cherry contained in clone (above), and the derived protein sequence therefor (below), as set forth in SEQ ID NOS. 15 and 16, respectively.

FIGS. 9A–9B are a representation showing the nucleotide sequence of genomic DNA encoding PPO of peach contained in clone GPCPO2 (above), and the derived protein sequence therefor (below), as set forth in SEQ ID NOS. 17 and 18, respectively.

FIGS. 10A–10B are a representation showing the nucleotide sequence of genomic DNA encoding PPO of pears contained in clone GPEPPO1 (above), and the derived protein sequence therefor (below), as set forth in SEQ ID NOS. 19 and 20, respectively.

FIGS. 11A–11B are a representation showing the nucleotide sequence of genomic DNA encoding PPO of pears contained in clone GPEPP02 (above), and the derived protein sequence therefor (below), as set forth in SEQ ID NOS. 21 and 22, respectively.

FIGS. 12A–12B are a representation showing the nucleotide sequence of genomic DNA encoding PPO of coffee contained in clone GCOP03 (above), and the derived protein sequence therefor (below), as set forth in SEQ ID NOS. 23 and 24, respectively.

FIGS. 13A–13B are a representation showing the nucleotide sequence of genomic DNA encoding PPO of coffee contained in clone GCOP04 (above), and the derived protein sequence therefor (below), as set forth in SEQ ID NOS. 25 and 26, respectively.

FIGS. 14A–14B are a representation showing the nucleotide sequence of genomic DNA encoding PPO of apple contained in clone GALP03 (above), and the derived protein sequence therefor (below), as set forth in SEQ ID NOS. 27 and 28, respectively.

FIGS. 15A–15B are a representation showing the nucleotide sequence of genomic DNA encoding PPO of lettuce contained in clone GLEP01 (above), and the derived protein sequence therefor (below), as set forth in SEQ ID NOS. 29 and 30, respectively.

FIGS. 16A–16B are a representation showing the nucleotide sequence of genomic DNA encoding PPO of French bean contained in clone GFP02 (above), and the derived protein sequence therefor (below), as set forth in SEQ ID NOS. 31 and 32, respectively.

FIGS. 17A–17B are a representation showing the nucleotide sequence of genomic DNA encoding PPO of French bean contained in clone GFP03 (above), and the derived protein sequence therefor (below), as set forth in SEQ ID NOS. 33 and 34, respectively.

FIGS. 18A–18B are a representation showing the nucleotide sequence of genomic DNA encoding PPO of French bean contained in clone GFP04 (above), and the derived protein sequence therefor (below), as set forth in SEQ ID NOS. 35 and 36, respectively.

FIG. 19 is a representation showing the nucleotide sequence of genomic DNA encoding PPO of banana contained in clone GBP02 (above), and the derived protein sequence therefor (below), as set forth in SEQ ID NOS. 37 and 38, respectively.

FIGS. 20A–20B are a representation showing the nucleotide sequence of genomic DNA encoding PPO of banana contained in clone GBP06 (above), and the derived protein sequence therefor (below), as set forth in SEQ ID NOS. 39 and 40, respectively.

FIGS. 21A–21B are a representation showing the nucleotide sequence of genomic DNA encoding PPO of rice contained in clone GRP05 (above: SEQ ID NO: 41), and the derived protein sequence therefor (below: SEQ ID NOS. 42, 43, and 44).

FIGS. 22A–22B are a representation showing the nucleotide sequence of genomic DNA encoding PPO of rice contained in clone GRP06 (above: SEQ ID NO: 45), and the derived protein sequence therefor (below: SEQ ID NOS. 46, 47, and 48).

FIGS. 23A–23B are a representation showing the nucleotide sequence of genomic DNA encoding PPO of potato contained in clone GPOT2 (above), and the derived protein sequence therefor (below), as set forth in SEQ ID NOS. 49 and 50, respectively.

FIGS. 24A–24B are a representation showing the nucleotide sequence of genomic DNA encoding PPO of potato contained in clone GPOT6 (above), and the derived protein sequence therefor (below), as set forth in SEQ ID NOS. 51 and 52, respectively.

FIGS. 25A–25B are a representation showing the nucleotide sequence of genomic DNA encoding PPO of potato contained in clone GPOT8 (above), and the derived protein sequence therefor (below), as set forth in SEQ ID NOS. 53 and 54, respectively.

FIGS. 26A–26B are a representation showing the nucleotide sequence of genomic DNA encoding PPO of potato contained in clone GPOT10 (above), and the derived protein sequence therefor (below), as set forth in SEQ ID NOS. 55 and 56, respectively.

DETAILED DESCRIPTION OF THE INVENTION

In a first aspect of the present invention there is provided a method for preparing nucleic acid encoding PPO, fragments and derivatives thereof, which method includes providing a sample of plant tissue, a first primer in sense orientation having a sequence corresponding to a conserved region of a PPO gene, a second primer in antisense orientation having a sequence corresponding to a conserved region of a PPO gene;

isolating genomic DNA from said plant tissue; and amplifying the genomic DNA using the first and second primers.

Surprisingly, the applicant has found that PPO genes in plants lack introns and, therefore, fragments of PPO genes may be amplified directly from genomic DNA of a range of plants. The lack of introns means that the size of the fragments can be predicted and bands of the appropriate size can be selected for cloning.

An advantage of the method of the present invention is that difficult steps of previous technologies (for example, identification of the appropriate stage of development of the target tissue, isolation of total and mRNA, first strand cDNA synthesis) are not required and genomic DNA encoding PPO or fragments thereof is readily isolated from a wide range of plants using relatively small amounts of tissue.

Since the sequences are derived from genomic DNA it is not possible to predict their temporal and spatial patterns of expression in the plant. Nevertheless, if a done expressed in a particular tissue, such as the fruit, is required such a clone may be identified by determining the expression pattern of each genomic done using northern analysis. Alternatively, the genomic clones may be used to obtain cDNA clones from the target tissue.

Applicant has found that some of the genomic clones obtained using the method of the present invention have the same or a very similar nucleotide sequence to previously obtained cDNA clones which are described in, for example, International Patent Applications PCT/AU92/00356 and PCT/AU96/0031 0 to the present applicant. This provides a validation of the method of the present invention and demonstrates that it can be used to obtain sequence of PPO genes which are known to be expressed in the target plants.

The terms "nucleic acid encoding strawberry, tobacco, apricot, avocado, cherry, peach, pear, pineapple, tea, coffee, apple, lettuce, French bean, banana, rice, potato, parsnip or wheat PPO" and "strawberry, tobacco, apricot, avocado, cherry, peach, pear, pineapple, tea, coffee, apple, lettuce, French bean, banana, rice, potato, parsnip or wheat PPO gene" as used herein should be understood to refer to the strawberry, tobacco, apricot, avocado, cherry, peach, pear, pineapple, tea, coffee, apple, lettuce, French bean, banana, rice, potato, parsnip or wheat PPO gene, respectively, or a sequence substantially homologous therewith, and may include presequences such as chloroplast transit sequence as well as sequences encoding mature PPO protein. For example, sequences which because of the degeneracy of the genetic code encode the same sequence of amino acids are encompassed by these terms.

The term "derivative' as used herein includes nucleic acids incorporating a catalytic cleavage site.

The plant tissue may be of any suitable type. Preferably, the plant tissue is leaf tissue, more preferably young leaf tissue. Preferably, the plant is strawberry, tobacco, apricot, avocado, cherry, peach, pear, pineapple, tea, coffee, apple, lettuce, French bean, banana, rice, potato, parsnip or wheat.

The genomic DNA may be isolated by any suitable method including extraction for example with a detergent such as CTAB. Methods for isolating genomic DNA from plants are well known to those skilled in the art and are described in, for example, Maniatis et al. "Molecular Cloning: A Laboratory Manual" Second Edition, Cold Spring Harbor Laboratory Press, 1989, the entire disclosure of which is incorporated herein by reference.

The first and second primers have sequences corresponding to conserved regions of PPO genes. These are identified by analysis of a number of known PPO genes.

The first primer may correspond to at least a portion of a first copper (Cu) binding site of PPO. Preferably, the first primer corresponds to at least a portion of one of the CuA or CuB binding sites of PPO, which are described in International Application PCT/AU92/00356, the entire disclosure of which is incorporated. herein by reference. The second primer may correspond to at least a portion of a second Cu binding site of PPO. Preferably, the second primer corresponds to at least a portion of the other of the CuA or CuB binding sites of PPO.

The first and second primers may be degenerate. The first primer may include one or more of the following sequences or parts thereof:

5'-GCGAATTCTT[TC][TC]TICCITT[TC]CA[TC][AC]G-3' (SEQ ID NO. 57)

5'-GCGAATTCGA[AG]GA[TC]ATGGGIAA[C]TT[TC]TA-3' (SEQ ID NO. 58)

5'-GCGAATTCAA[TC]GTIGA[TC][AC]GIATGTGG-3' (SEQ ID NO. 59)

5'-GCGAATTCGATCCIACITT[TC]GC[GT]TTlICC-3' (SEQ ID NO. 60)

5'-GCGAATTCTICA[TC]TG[TC]GCITA[TC]TG-3' (SEQ ID NO. 61)

5'-GCGAATTCTTICCIT[TA][TC]TGGAA[TC]TGGG-3' (SEQ ID NO. 62)

The second primer may include one or more of the following sequences or parts thereof:

5'-GCCTGCAGCCACATIC[TG][AG]TCIAC[AG]TT-3' (SEQ ID NO. 63)

5'-GCCTGCAGTT[TC]TC[AG]TC[AG]TAGAA-3' (SEQ ID NO. 64)

5'-GCCTGCAGA[TC]A[GA]CTICCI GCAAACTC-3' (SEQ ID NO. 65)

5'-GCCTGCAGTC[TC]TCIA[AG]IA[AG]ITCIG-3' (SEQ ID NO. 66)

The genomic DNA may be amplified using the polymerase chain reaction (PCR). Preferably the concentration of genomic DNA in the amplification mixture is approximately 0.4 to 4 ng/$\mu$l, more preferably approximately 1 to 3 ng/$\mu$l, most preferably approximately 2 ng/$\mu$l.

Preferably the concentration of each of the primers in the amplification mixture is approximately 0.1 to 10 $\mu$M, more preferably approximately 0.5 to 2 $\mu$M, most preferably approximately 1 $\mu$M.

Preferably the amplification involves an initial denaturation at approximately 94° C. for approximately 3 min, followed by approximately two cycles with denaturation at approximately 94° C. for approximately 1 min, annealing at approximately 37° C. for approximately 2 min, a slow ramp to approximately 72° C. over approximately 2 min and elongation at approximately 72° C. for approximately 3 min, followed by approximately 25 cycles of denaturation at approximately 94° C. for approximately 1 min, annealing at approximately 55° C. for approximately 1 min, and elongation at approximately 72° C. for approximately 3 min.

Those skilled in the art will appreciate that if the conserved regions are internal, the nucleic acid isolated will be a fragment of the PPO gene lacking 3' and 5' termini. However, using methods known to those skilled in the art, including the methods described in International Patent Application PCT/AU96/00310 to the present applicant, the entire disclosure of which is incorporated herein by reference, it is possible to determine the complete nucleic acid sequence of the PPO gene and to prepare or isolate nucleic acid encoding such PPO or antisense to such PPO.

In a further aspect of the present invention, there is provided a nucleic acid encoding strawberry PPO or antisense to strawberry PPO, fragments and derivatives thereof. Preferably the nucleic acid has the sequence shown in FIGS. 1 or 2 or an homologous sequence.

In a further aspect of the present invention, there is provided a nucleic acid encoding tobacco PPO or antisense to tobacco PPO, fragments and derivatives thereof. Preferably the nucleic acid has the sequence shown in FIGS. 3 or 4 or an homologous sequence.

In a further aspect of the present invention, there is provided a nucleic acid encoding apricot PPO or antisense to apricot PPO, fragments and derivatives thereof. Preferably the nucleic acid has the sequence shown in FIG. 5 or an homologous sequence.

In a further aspect of the present invention, there is provided a nucleic acid encoding avocado PPO or antisense to avocado PPO, fragments and derivatives thereof. Preferably the nucleic acid has the sequence shown in FIG. 6 or an homologous sequence.

In a further aspect of the present invention, there is provided a nucleic acid encoding cherry PPO or antisense to cherry PPO, fragments and derivatives thereof. Preferably the nucleic acid has the sequence shown in FIGS. 7 or 8 or an homologous sequence.

In a further aspect of the present invention, there is provided a nucleic acid encoding peach PPO or antisense to peach PPO, fragments and derivatives thereof. Preferably the nucleic acid has the sequence shown in FIG. 9 or an homologous sequence.

In a further aspect of the present invention, there is provided a nucleic acid encoding pear PPO or antisense to pear PPO, fragments and derivatives thereof. Preferably the nucleic acid has the sequence shown in FIGS. 10 or 11 or an homologous sequence.

In a further aspect of the present invention, there is provided a nucleic acid encoding pineapple PPO or antisense to pineapple PPO, fragments and derivatives thereof.

In a further aspect of the present invention, there is provided a nucleic acid encoding tea PPO or antisense to tea PPO, fragments and derivatives thereof.

In a further aspect of the present invention, there is provided a nucleic acid encoding coffee PPO or antisense to coffee PPO, fragments and derivatives thereof. Preferably the nucleic acid has the sequence shown in FIGS. 12 or 13 or an homologous sequence.

In a further aspect of the present invention, there is provided a nucleic acid encoding apple PPO or antisense to apple PPO, fragments and derivatives thereof. Preferably the nucleic acid has the sequence shown in FIG. 14 or an homologous sequence.

In a further aspect of the present invention, there is provided a nucleic acid encoding lettuce PPO or antisense to lettuce PPO, fragments and derivatives thereof. Preferably the nucleic acid has the sequence shown in FIG. 15 or an homologous sequence.

In a further aspect of the present invention, there is provided a nucleic acid encoding French bean PPO or antisense to French be an PPO, fragments and derivatives thereof. Preferably the nucleic acid has the sequence shown in FIGS. 16, 17 or 18 or an homologous sequence.

In a further aspect of the present invention, there is provided a nucleic acid encoding banana PPO or antisense to banana PPO, fragments and derivatives thereof. Preferably the nucleic acid has the sequence shown in FIGS. 19 or 20 or an homologous sequence.

In a further aspect of the present invention, there is provided a nucleic acid encoding rice. PPO or antisense to rice PPO, fragments and derivatives thereof. Preferably the nucleic acid has the sequence shown in FIGS. 21 or 22 or an homologous sequence.

In a further aspect of the present invention, there is provided a nucleic acid encoding potato PPO or antisense to potato PPO, fragments and derivatives thereof. Preferably the nucleic acid has the sequence shown in FIGS. 23, 24, 25 or 26 or an homologous sequence.

In a further aspect of the present invention, there is provided a nucleic acid encoding parsnip PPO or antisense to parsnip PPO, fragments and derivatives thereof.

In a further aspect of the present invention, there is provided a nucleic acid encoding wheat PPO or antisense to wheat PPO, fragments and derivatives thereof.

The nucleic acid may be provided in an isolated and/or purified form.

Fragments of the nucleic acid sequence are preferably functionally active i.e. they encode a polypeptide that possesses the relevant PPO activity or they encode a relevant epitope.

The nucleic acid may be prepared by a method as hereinbefore described. The nucleic acid may be modified, for example by inclusion of a catalytic cleavage site.

In a further aspect of the present invention there is provided a method for preparing a recombinant vector including a nucleic acid encoding strawberry, tobacco, apricot, avocado, cherry, peach, pear, pineapple, tea, coffee, apple, lettuce, French bean, banana, rice, potato, parsnip or wheat PPO or antisense to such PPO, fragments and derivatives thereof, which method includes providing nucleic acid encoding strawberry, tobacco, apricot, avocado, cherry, peach, pear, pineapple, tea, coffee, apple, lettuce, French bean, banana, rice, potato, parsnip or wheat PPO or antisense to such PPO, fragments and derivatives thereof; and a vector; and reacting the nucleic acid and the vector to deploy the nucleic acid within the vector.

The nucleic acid may be prepared by a method as hereinbefore described.

The nucleic acid may be modified, for example by inclusion of a catalytic cleavage site.

The vector may be a plasmid expression vector. For example Bluescript SK$^+$ has been found to be suitable. Alternatively, the vector may be a binary vector. The recombinant vector may contain a promoter, preferably a constitutive promoter upstream of the nucleic acid.

The cloning step may take any suitable form. A preferred form may include fractionating the cDNA, for example on a column or a gel; isolating a fragment of the expected size, for example from the column or gel; and ligation said fragment into a suitable restriction enzyme site, for example the EcoRV site of a Bluescript SK$^+$ vector.

In order to test the clones so formed, a suitable microorganism may be transformed with the vector, for example by electroporation, the microorganism cultured and the polypeptide encoded therein expressed. The microorganism may be a strain of *Escherichia coli*, for example *E. coli* DH5 has been found to be suitable. Alternatively, appropriate vectors may be used to transform plants.

In a further aspect of the present invention there is provided a recombinant vector including a nucleic acid encoding strawberry, tobacco, apricot, avocado, cherry, peach, pear, pineapple, tea, coffee, apple, lettuce, French bean, banana, rice, potato, parsnip or wheat PPO or antisense to such PPO, fragments and derivatives thereof, which vector is capable of being replicated, transcribed and translated in a unicellular organism or alternatively in a plant.

The nucleic acid may be prepared by a method as hereinbefore described.

The nucleic acid may be modified, for example by inclusion of a catalytic cleavage site.

The vector may be a plasmid expression vector. For example Bluescript SK$^+$ has been found to be suitable. Alternatively, the vector may be a binary vector. The recombinant vector may contain a promoter, preferably a constitutive promoter upstream of the nucleic acid encoding strawberry, tobacco, apricot, avocado, cherry, peach, pear, pineapple, tea, coffee, apple, lettuce, French bean, banana, rice, potato, parsnip or wheat PPO or antisense to such PPO, fragments and derivatives thereof.

The microorganism may be a strain of *Escherichia coli*, for example *E. coli* DH5 has been found to be suitable.

In a further aspect of the present invention there is provided a method of decreasing the level of PPO activity in a plant tissue, which method includes providing a nucleic acid encoding strawberry, tobacco, apricot, avocado, cherry, peach, pear, pineapple, tea, coffee, apple, lettuce, French bean, banana, rice, potato, parsnip or wheat PPO, a modified nucleic acid encoding such PPO, or a nucleic acid antisense to strawberry, tobacco, apricot, avocado, cherry, peach, pear, pineapple, tea, coffee, apple, lettuce, French bean, banana, rice, potato, parsnip or wheat PPO, fragments and derivatives thereof; and a plant sample; and introducing said nucleic acid into said plant sample to produce a transgenic plant.

PPO activity may be decreased by the use of sense constructs (cosuppression). Alternatively the nucleic acid may include a sequence encoding antisense mRNA to strawberry, tobacco, apricot, avocado, cherry, peach, pear, pineapple, tea, coffee, apple, lettuce, French bean, banana, rice, potato, parsnip or wheat PPO or a fragment thereof. Alternatively the nucleic acid may encode strawberry, tobacco, apricot, avocado, cherry, peach, pear, pineapple, tea, coffee, apple, lettuce, French bean, banana, rice, potato, parsnip or wheat PPO or fragment thereof and incorporate a catalytic cleavage site (ribozyme). The nucleic acid may be included in a recombinant vector as hereinbefore described. In a preferred aspect, the nucleic acid may be included in a binary vector. In a further preferred aspect, the introduction of a binary vector into the plant may be by infection of the plant with an Agrobacterium containing the binary vector or by bombardment with nucleic acid coated micro projectiles. Methods for transforming plants with Agrobacterium are known to those skilled in the art and are described in, for example, May et al., Biotechnology (1995) 13:486492, the entire disclosure of which is incorporated herein by reference. Methods for transforming plants by bombardment with DNA coated microprojectiles are known to those skilled in the art and are described in, for example, Sagi et al., Biotechnology (1995) 13:481–485, the entire disclosure of which is incorporated herein by reference.

In a further aspect of the present invention there is provided a method of increasing the level of PPO activity in a plant tissue, which method includes providing a nucleic acid encoding strawberry, tobacco, apricot, avocado, cherry, peach, pear, pineapple, tea, coffee, apple, lettuce, French bean, banana, rice, potato, parsnip or wheat PPO or a fragment thereof; and a plant sample; and introducing said nucleic acid into said plant sample to produce a transgenic plant.

The nucleic acid may be included in a recombinant vector as hereinbefore described. In a preferred aspect, the nucleic acid may be included in a binary vector. In a further preferred aspect, the introduction of the binary vector into the plant may be by infection of the plant with an Agrobacterium containing the binary vector. or by bombardment with nucleic acid coated microprojectiles.

The plant may be of any suitable type. However the method is particularly applicable to strawberry, tobacco, apricot, avocado, cherry, peach, pear, pineapple, tea, coffee, apple, lettuce, French bean, banana, rice, potato, parsnip or wheat, respectively.

In a further aspect of the present invention there is provided a transgenic plant, which plant contains nucleic acid capable of modifying expression of the normal PPO gene.

The plant may be of any suitable type. Preferably, the plant is strawberry, tobacco, apricot,, avocado, cherry, peach, pear, pineapple, tea, coffee, apple, lettuce, French bean, banana, rice, potato, parsnip or wheat.

The nucleic acid may be as hereinbefore described.

In a still further aspect of the present invention there is provided a plant vaccine including nucleic acid encoding strawberry, tobacco, apricot, avocado, cherry, peach, pear, pineapple, tea, coffee, apple, lettuce, French bean, banana, rice, potato, parsnip or wheat PPO or antisense to such PPO, fragments and derivatives thereof.

The present invention will now be more fully described with reference to the accompanying Example. It should be understood, however, that the description following is illustrative only and should not be taken in any way as a restriction on the generality of the invention described above. The present invention is further described with references tot the following non-limiting examples.

EXAMPLE 1

Isolating Genomic PPO Clones

Genomic DNA was isolated from young leaf tissue of a range of different plants using the hot CTAB method described by Stewart, CN and Via, LE (1993) "A rapid CTAB DNA isolation technique useful for RAPD fingerprinting and other PCR applications" BioTechniques 14:748–750, the entire disclosure of which is incorporated herein by reference. Based on known plant PPO DNA sequences, oligonucleotide primers were designed in the conserved regions of the gene, particularly in the regions which encode the two copper binding sites, CuA and CuB (Dry, IB and Robinson, SP (1994) "Molecular cloning and characterisation of grape berry polyphenol oxidase" Plant Molecular Biology 26:495–502; Thygesen, PW, Dry, IB and Robinson, SP (1995) "Polyphenol oxidase in potato. A multigene family that exhibits differential expression patterns" Plant physiology 109:525–531, the entire disclosures of which are incorporated herein by reference).

A number of forward primers (GEN34 and GEN7–10) and reverse primers (R 1–4) were synthesised, as follows:

GEN3 (SEQ ID NO:57): (5'-GCGMTTCTT[TC][TC]TICCITT[TC]CA[TC][AC]G-3')

GEN4 (SEQ ID NO:58): (5'-GCGMTTCGA[AG]GA[TC]ATGGGIAA[TC]TT[TC]TA-3')

GEN7 (SEQ ID NO:59): (5'-GCGMTTCM[TC]GTIGA[TC][AC]GIATGTGG-3')

GEN8 (SEQ ID NO:60): (5'-GCGMTTCGATCCIACITT[TC]GC[GT]TTICC-3')

GEN9 (SEQ ID NO:61): (5'-GCGMTTCTICA[TC]TG[TC]GCITA[TC]TG-3')

GEN10 (SEQ ID NO:62): (5'-GCGMTTCTTICCIT[TA][TC]TGGAA[TC]TGGG-3')

REV1 (SEQ ID NO:63): (5'-GCCTGCAGCCACATIC[TG][AG]TCIAC[AG]TT-3')

REV2 (SEQ ID NO:64): (5'-GCCTGCAGTT[TC]TC[AG]TC[AG]TAGAA-3')

REV3 (SEQ ID NO:65): (5'-GCCTGCAGA[TC]A[GA]CTICCIGCAAACTC-3')

REV4 (SEQ ID NO:66): (5'-GCCTGCAGTC[TC]TCIA[AG]IA[AG] ITCIG-3')

The genomic DNA (50 ng) was amplified by PCR in a 25 $\mu$l reaction using combinations of the GEN and REV primers (see Table 1), each at a final concentration of 1 $\mu$M.

TABLE 1

PPO Genomic Clones

| Plant | Clone # | Fig # | Size | 5'-Primer | 3'-Primer | Comments |
|---|---|---|---|---|---|---|
| Strawberry | GSP02 | 1 | 590 | GEN3 | REV2 | |
| Strawberry | GSP04 | | 440 | GEN8 | REV1 | 76% same as GSP02 |
| Strawberry | GSP05 | | 527 | GEN8 | REV2 | 96% same as GSP02 |
| Strawberry | GSP06 | 2 | 527 | GEN8 | REV2 | 98% same as GSP04 |
| Tobacco | GTP01 | 3 | 465 | GEN8 | REV1 | |
| Tobacco | GTIDO2 | | 459 | GEN8 | REV1 | 97% same as GTP03 |
| Tobacco | GTP03 | 4 | 545 | GEN8 | REV2 | 69% same as GTP01 |
| Apricot | GAP01 | | 465 | GEN8 | REV1 | |
| Apricot | GAP02 | | 465 | GEN8 | REV1 | same as GAP01 |
| Apricot | GAP03 | 5 | 548 | GEN8 | REV2 | same as GAP01 |

TABLE 1-continued

PPO Genomic Clones

| Plant | Clone # | Fig # | Size | 5'-Primer | 3'-Primer | Comments |
|---|---|---|---|---|---|---|
| Avocado | GAVP01 | 6 | 590 | GEN3 | REV2 | |
| Avocado | GAVP02 | | 590 | GEN3 | REV2 | 95% same as GAVP01 |
| Cherry | GCP01 | 7 | 590 | GEN3 | REV2 | |
| Ch | GCP02 | 8 | 442 | GEN8 | REV1 | 67% same as GCP01 |
| Peach | GPCP01 | | 465 | GEN8 | REV1 | |
| Peach | GPCP02 | 9 | 548 | GEN8 | REV2 | 98% same as GPCP01 |
| Pear | GPEPP01 | 10 | 465 | GEN8 | REV1 | |
| Pear | GPEPP02 | 11 | 527 | GEN8 | REV2 | 56% same as GPEPP01 |
| Pear | GPEPP03 | | 548 | GEN8 | REV2 | same as GPEPP01 |
| Coffee | GCOP03 | 12 | 674 | GEN9 | REV2 | |
| Coffee | GCOP04 | 13 | 667 | GEN9 | REV2 | 94% same as GCOP03 |
| Apple | GALP03 | 14 | 588 | GEN9 | REV1 | |
| Lettuce | GLEP01 | 15 | 671 | GEN9 | REV2 | 70% same as LP01 |
| French bean | GFP02 | 16 | 668 | GEN9 | REV2 | |
| French bean | GFP03 | 17 | 689 | GEN9 | REV2 | 63% same as GFP02 |
| French bean | GFP04 | 18 | 662 | GEN9 | REV2 | 65% same as GFP02 |
| Banana | GBP02 | 19 | 426 | GEN10 | REV1 | =BANPP01 (cDNA) |
| Banana | GBP06 | 20 | 512 | GEN10 | REV2 | 53% same as GBP02 |
| Rice | GRP05 | 21 | 662 | GEN10 | REV2 | (contains an intron!) |
| Rice | GRP06 | 22 | 622 | GEN10 | REV2 | 64% same as GRP06 |
| Potato | GPOT2 | 23 | 551 | GEN8 | REV2 | 75% same as POT33 |
| Potato | GPOT6 | 24 | 682 | GEN9 | REV2 | Same as POT32 (cDNA) |
| Potato | GPOTB | 25 | 536 | GEN10 | REV2 | 71% same as POT33 |
| Potato | GPOT10 | 26 | 515 | GEN10 | REV2 | 979 same as P1 & P2 (cDNA) |

Amplification involved an initial denaturation at 94° C. for 3 min, followed by two cycles with 40 denaturation at 94° C. for 1 min, annealing at 370 C for 2 min, a slow ramp to 72° C. over 2 min and elongation at 72° C. for 3 min, followed by 25 cycles of denaturation at 94° C. for 1 min, annealing at 55° C. for 1 min, and elongation at 72° C. for 3 min. A sample of the amplified DNA was run on an agarose gel and stained with ethidium bromide to determine the size of the PCR products. Where bands of the predicted size were identified, the remainder of the DNA was purified and concentrated using PCR Wizard Prep columns (Promega Corporation) or a QlAquick Spin PCR Purification Kit (QIAGEN Inc).

The purified DNA was electrophoresed on a 2% Nusieve agarose gel and bands of the appropriate size were excised and ligated into Eco RV-cut Bluescript $SK^+$ vector (Stratagene) which had been T-tailed with Taq Polymerase. The ligated DNA was introduced into *E. coli* DH5a by electroporation. Recombinant clones which had an insert of the predicted size were selected and their DNA sequence was determined by automated sequencing. Identity of PPO clones was established by homology with known plant PPO gene sequences.

Finally, it is to be understood that various other modifications and/or alterations may be made without departing from the spirit of the present invention as outlined herein.

What is claimed is:

1. An isolated plant polyphenol oxidase (PPO) gene fragment consisting of a nucleotide sequence selected from the group consisting of SEO ID NOs: 1, 3, 5, 7, 9, 11, 13, 15, 17, 19, 21, 23, 25, 27, 29, 31, 33, 35, 37, 39, 41, 46, 49, 51, 53, and 55 wherein said nucleotide sequence encodes a plant PPO polypeptide fragment that includes one or more conserved copper-binding sites of plant PPO polypeptides, and wherein said PPO gene fragment is prepared by a process comprising:

(i) providing:
 (a) a tissue sample from a plant;
 (b) a first primer comprising a nucleotide sequence selected from the group consisting of SEQ ID NOs: 57, 58, 59, 60, 61, and 62; and
 (c) a second primer comprising a nucleotide sequence selected from the group consisting of SEQ ID NOs: 63, 64, 65, and 66;

(ii) isolating genomic DNA from said tissue sample;

(iii) performing a polymerase chain reaction on said genomic DNA using the first primer and the second primer to amplify said PPO gene fragment from said genomic DNA; and (iv) isolating the amplified PPO gene fragment.

2. The isolated plant PPO gene fragment according to claim 1 wherein the plant is selected from the group consisting of: strawberry, tobacco, apricot, avocado, cherry, peach, pear, coffee, apple, lettuce, French bean, banana, rice, and potato.

3. An isolated strawberry PPO gene fragment consisting of a nucleotide sequence selected from the group consisting of:

(i) the nucleotide sequence set forth in SEQ ID NO: 1 or 3;

(ii) a nucleotide sequence which encodes the amino acid sequence set forth in SEQ ID NO: 2 or 4; and (iii) a nucleotide sequence complementary to (i) or (ii).

4. An isolated tobacco PPO gene fragment consisting of a nucleotide sequence selected from the group consisting of:

(i) the nucleotide sequence set forth in SEQ ID NO: 5 or 7;

(ii) a nucleotide sequence which encodes the amino acid sequence set forth in SEQ ID NO: 6 or 8; and (iii) a nucleotide sequence complementary to (i) or (ii).

5. An isolated apricot PPO gene fragment consisting of a nucleotide sequence selected from the group consisting of:

(i) the nucleotide sequence set forth in SEQ ID NO: 9;

(ii) a nucleotide sequence which encodes the amino acid sequence set forth in SEQ ID NO: 10; and (iii) a nucleotide sequence complementary to (i) or (ii).

6. An isolated avocado PPO gene fragment consisting of a nucleotide sequence selected from the group consisting of:

(i) the nucleotide sequence set forth in SEQ ID NO: 11;

(ii) a nucleotide sequence which encodes the amino acid sequence set forth in SEQ ID NO: 12; and (iii) a nucleotide sequence complementary to (i) or (ii).

7. An isolated cherry PPO gene fragment consisting of a nucleotide sequence selected from the group consisting of:

(i) the nucleotide sequence set forth in SEQ ID NO: 13 or 15;

(ii) a nucleotide sequence which encodes the amino acid sequence set forth in SEQ ID NO: 14 or 16; and (iii) a nucleotide sequence complementary to (i) or (ii).

8. An isolated peach PPO gene fragment consisting of a nucleotide sequence selected from the group consisting of:

(i) the nucleotide sequence set forth in SEQ ID NO: 17;

(ii) a nucleotide sequence which encodes the amino acid sequence set forth in SEQ ID NO: 18; and (iii) a nucleotide sequence complementary to (i) or (ii).

9. An isolated pear PPO gene fragment consisting of a nucleotide sequence selected from the group consisting of:

(i) the nucleotide sequence set forth in SEQ ID NO: 19 or 21;

(ii) a nucleotide sequence which encodes the amino acid sequence set forth in SEQ ID NO: 20 or 22; and (iii) a nucleotide sequence complementary to (i) or (ii).

10. An isolated coffee PPO gene fragment consisting of a nucleotide sequence selected from the group consisting of:

(i) the nucleotide sequence set forth in SEQ ID NO: 23 or 25;

(ii) a nucleotide sequence which encodes the amino acid sequence set forth in SEQ ID NO: 26 or 28; and (iii) a nucleotide sequence complementary to (i) or (ii).

11. An isolated apple PPO gene fragment consisting of a nucleotide sequence selected from the group consisting of:

(i) the nucleotide sequence set forth in SEQ ID NO: 27;

(ii) a nucleotide sequence which encodes the amino acid sequence set forth in SEQ ID NO: 28; and (iii) a nucleotide sequence complementary to (i) or (ii).

12. An isolated lettuce PPO gene fragment consisting of a nucleotide sequence selected from the group consisting of:

(i) the nucleotide sequence set forth in SEQ ID NO: 29;

(ii) a nucleotide sequence which encodes the amino acid sequence set forth in SEQ ID NO: 30; and (iii) a nucleotide sequence complementary to (i) or (ii).

13. An isolated French bean PPO gene fragment consisting of a nucleotide sequence selected from the group consisting of:

(i) a nucleotide sequence selected from the group consisting of SEQ ID NO: 31, SEQ ID NO: 33 and SEQ ID NO: 35;

(ii) a nucleotide sequence which encodes an amino acid sequence selected from the group consisting of SEQ ID NO: 32, SEQ ID NO: 34 and SEQ ID NO: 36; and (iii) a nucleotide sequence complementary to (i) or (ii).

14. An isolated banana PPO gene fragment consisting of a nucleotide sequence selected from the group consisting of:

(i) the nucleotide sequence set forth in SEQ ID NO: 37 or 39;

(ii) a nucleotide sequence which encodes the amino acid sequence set forth in SEQ ID NO: 38 or 40; and (iii) a nucleotide sequence complementary to (i) or (ii).

15. An isolated rice PPO gene fragment consisting of a nucleotide sequence selected from the group consisting of:

(i) the nucleotide sequence set forth in SEQ ID NO: 41 or 46;

(ii) a nucleotide sequence which encodes an amino acid sequence selected from the group consisting of SEQ ID NO: 42, SEQ ID NO: 43,SEQ ID NO: 44, SEQ ID NO: 45, SEQ ID NO: 47, and SEQ ID NO: 48; and (iii) a nucleotide sequence complementary to (i) or (ii).

16. An isolated potato PPO gene fragment consisting of a nucleotide sequence selected from the group consisting of:

(i) a nucleotide sequence selected from the group consisting of SEQ ID NO: 49, SEQ ID NO: 51, SEQ ID NO: 53 and SEQ ID NO: 55;

(ii) a nucleotide sequence which encodes an amino acid sequence selected from the group consisting of SEQ ID NO: 50, SEQ ID NO: 51, SEQ ID NO: 54 and SEQ ID NO: 56; and (iii) a nucleotide sequence complementary to (i) or (ii).

17. A method for preparing a recombinant vector comprising a plant polyphenol oxidase (PPO ) gene fragment consisting of a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 46, 49, 51, 53, and 55 wherein said nucleotide sequence encodes a fragment of a plant PPO polypeptide that includes one or more conserved copper-binding sites of plant PPO polypeptides, said method comprising:

(i) providing:

(a) an isolated PPO gene fragment having a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 46, 49, 51, 53, and 55, or having a sequence which encodes the same amino acid sequence as said nucleotide sequence or having a sequence complementary to said nucleotide sequence; and (b) a vector; and (ii) ligating said nucleic acid within said vector.

18. The method according to claim 17 wherein the PPO gene fragment is prepared by a process comprising:

(i) providing:

(a) a tissue sample from a plant selected from the group consisting of strawberry, tobacco, apricot, avocado, cherry, peach, pear, coffee, apple, lettuce, French bean, banana, rice and potato;

(b) a first primer having a sequence encoding a conserved copper-binding site of plant PPO polypeptides wherein said primer anneals to a first DNA strand of a PPO gene of said plant;

(c) a second primer having a sequence complementary to a sequence encoding a conserved copper-binding site of plant PPO polypeptides wherein said primer anneals to a second DNA strand of a PPO gene of said plant and wherein said second primer is not complementary to said first primer;

(ii) isolating genomic DNA from said tissue sample;

(iii) performing a polymerase chain reaction on said genomic DNA using the first primer and the second primer to amplify a PPO gene fragment from said genomic DNA; and (iv) isolating the PPO gene fragment.

19. The method according to claim 17 wherein the vector is a plasmid expression vector selected from the group consisting of Bluescript $SK^+$, a binary vector and a vector containing a promoter sequence.

20. A recombinant vector comprising in operable linkage a plant polyphenol oxidase (PPO) gene fragment which encodes a PPO polypeptide fragment including one or more conserved copper-binding sites of plant PPO polypeptides and a promoter sequence, wherein said PPO gene fragment consists of a nucleotide sequence selected from the group consisting of:

(i) a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 46, 49, 51, 53, and 55;

(ii) a nucleotide sequence that encodes an amino acid sequence selected from the group consisting of SEQ ID NOs: 2, 4, 6, 8, 10, 12, 14, 16, 18, 20, 22, 24, 26, 28, 30, 32, 34, 36, 38, 40, 42, 43, 44, 45, 47, 48, 50, 52, 54, and 56; and (iii) a nucleotide sequence that is complementary to (i) or (ii).

21. The recombinant vector according to claim 20 wherein the plant PPO gene fragment is prepared by a process comprising:

(i) providing:

(a) a tissue sample from a plant selected from the group consisting of strawberry, tobacco, apricot, avocado, cherry, peach, pear, coffee, apple, lettuce, French bean, banana, rice and potato;

(b) a first primer comprising a nucleotide sequence selected from the group consisting of SEQ ID NOs: 57, 58, 59, 60, 61, and 62; and (d) a second primer comprising a nucleotide sequence selected from the group consisting of SEQ ID NOs: 63, 64, 65, and 66;

(ii) isolating genomic DNA from said tissue sample;

(iii) performing a polymerase chain reaction on said genomic DNA using the first primer and the second primer to amplify a PPO gene fragment from said genomic DNA; and (iv) isolating the PPO gene fragment.

* * * * *

SEQUENCE LISTING

```
<160> NUMBER OF SEQ ID NOS: 66

<210> SEQ ID NO 1
<211> LENGTH: 590
<212> TYPE: DNA
<213> ORGANISM: STRAWBERRY
<220> FEATURE:
<221> NAME/KEY: CDS
<222> LOCATION: (1)..(588)

<400> SEQUENCE: 1

ttt ctg gcg ttc cac aga tac tac ttg tac ttc tat gag aga atc ctg        48
Phe Leu Ala Phe His Arg Tyr Tyr Leu Tyr Phe Tyr Glu Arg Ile Leu
  1               5                  10                  15

gga aaa ttg atc aac gac ccg tcg ctc gcc tcg act ttc tgg aac tgg        96
Gly Lys Leu Ile Asn Asp Pro Ser Leu Ala Ser Thr Phe Trp Asn Trp
             20                  25                  30

gat gct ccg gct ggc atg caa ctc cca ggc atg ttt gcc aat cct aag       144
Asp Ala Pro Ala Gly Met Gln Leu Pro Gly Met Phe Ala Asn Pro Lys
         35                  40                  45
```

-continued

```
tcg ccg ctc tac gac aag ttc cga aac gcc aac cat cag tcg ccg aag      192
Ser Pro Leu Tyr Asp Lys Phe Arg Asn Ala Asn His Gln Ser Pro Lys
     50                  55                  60

ctc att gac ctc aat tac aat ctc aag gat gaa aac gtc tcc gac gaa      240
Leu Ile Asp Leu Asn Tyr Asn Leu Lys Asp Glu Asn Val Ser Asp Glu
 65                  70                  75                  80

act caa ata aac acc aac ctc aag atc atg tac agg caa atg gtg tcc      288
Thr Gln Ile Asn Thr Asn Leu Lys Ile Met Tyr Arg Gln Met Val Ser
                 85                  90                  95

aac gcc aag aac cct aag ctg ttc ttt gga aac cct tat agg gct ggg      336
Asn Ala Lys Asn Pro Lys Leu Phe Phe Gly Asn Pro Tyr Arg Ala Gly
            100                 105                 110

gac gag cct agc ccc gga ggc gga gca ata gag act act cca cat gga      384
Asp Glu Pro Ser Pro Gly Gly Gly Ala Ile Glu Thr Thr Pro His Gly
        115                 120                 125

ccg gtc cac att tgg acc ggt gac aac ata cag ccg aat ctt gag gac      432
Pro Val His Ile Trp Thr Gly Asp Asn Ile Gln Pro Asn Leu Glu Asp
    130                 135                 140

atg gga aac ttc tac tct gct ggt aga gac cct ata ttt ttc tct cat      480
Met Gly Asn Phe Tyr Ser Ala Gly Arg Asp Pro Ile Phe Phe Ser His
145                 150                 155                 160

cac tct aac gtt gac cgt ttg tgg agt gtg tgg aaa acc cta gga ggc      528
His Ser Asn Val Asp Arg Leu Trp Ser Val Trp Lys Thr Leu Gly Gly
                165                 170                 175

aag aga gcg gat ttc act gac tct gat tgg ttg gat tcg ggg ttt ttg      576
Lys Arg Ala Asp Phe Thr Asp Ser Asp Trp Leu Asp Ser Gly Phe Leu
            180                 185                 190

ttc tac gat gaa aa                                                   590
Phe Tyr Asp Glu
        195
```

```
<210> SEQ ID NO 2
<211> LENGTH: 196
<212> TYPE: PRT
<213> ORGANISM: STRAWBERRY

<400> SEQUENCE: 2

Phe Leu Ala Phe His Arg Tyr Tyr Leu Tyr Phe Tyr Glu Arg Ile Leu
  1               5                  10                  15

Gly Lys Leu Ile Asn Asp Pro Ser Leu Ala Ser Thr Phe Trp Asn Trp
            20                  25                  30

Asp Ala Pro Ala Gly Met Gln Leu Pro Gly Met Phe Ala Asn Pro Lys
        35                  40                  45

Ser Pro Leu Tyr Asp Lys Phe Arg Asn Ala Asn His Gln Ser Pro Lys
     50                  55                  60

Leu Ile Asp Leu Asn Tyr Asn Leu Lys Asp Glu Asn Val Ser Asp Glu
 65                  70                  75                  80

Thr Gln Ile Asn Thr Asn Leu Lys Ile Met Tyr Arg Gln Met Val Ser
                 85                  90                  95

Asn Ala Lys Asn Pro Lys Leu Phe Phe Gly Asn Pro Tyr Arg Ala Gly
            100                 105                 110

Asp Glu Pro Ser Pro Gly Gly Gly Ala Ile Glu Thr Thr Pro His Gly
        115                 120                 125

Pro Val His Ile Trp Thr Gly Asp Asn Ile Gln Pro Asn Leu Glu Asp
    130                 135                 140

Met Gly Asn Phe Tyr Ser Ala Gly Arg Asp Pro Ile Phe Phe Ser His
145                 150                 155                 160
```

-continued

```
His Ser Asn Val Asp Arg Leu Trp Ser Val Trp Lys Thr Leu Gly Gly
                165                 170                 175

Lys Arg Ala Asp Phe Thr Asp Ser Asp Trp Leu Asp Ser Gly Phe Leu
            180                 185                 190

Phe Tyr Asp Glu
        195


<210> SEQ ID NO 3
<211> LENGTH: 527
<212> TYPE: DNA
<213> ORGANISM: STRAWBERRY
<220> FEATURE:
<221> NAME/KEY: CDS
<222> LOCATION: (1)..(525)

<400> SEQUENCE: 3

gat ccg acg ttt gcg ttg ccg ttt tgg aac tgg gac aac cct gct ggc       48
Asp Pro Thr Phe Ala Leu Pro Phe Trp Asn Trp Asp Asn Pro Ala Gly
  1               5                  10                  15

atg cag ctg cct gcc ttg ttc gcc aat cct aaa tca ccg ctt tac gac       96
Met Gln Leu Pro Ala Leu Phe Ala Asn Pro Lys Ser Pro Leu Tyr Asp
             20                  25                  30

cag ttc aga gcc gcc gct cat cag ccg ccg acc ctg atc gac ctc gat      144
Gln Phe Arg Ala Ala Ala His Gln Pro Pro Thr Leu Ile Asp Leu Asp
         35                  40                  45

ttc aac ggt acg gag gac aac aca tca aac aca aca caa atc aac agc      192
Phe Asn Gly Thr Glu Asp Asn Thr Ser Asn Thr Thr Gln Ile Asn Ser
     50                  55                  60

aac tta agc att atg tac cgt caa atg gta tct aac gcc aag aat gct      240
Asn Leu Ser Ile Met Tyr Arg Gln Met Val Ser Asn Ala Lys Asn Ala
 65                  70                  75                  80

cag ctc ttc ttc ggc aac cca tac cgg gct ggg gac gag cct gac ccc      288
Gln Leu Phe Phe Gly Asn Pro Tyr Arg Ala Gly Asp Glu Pro Asp Pro
                 85                  90                  95

ggt ggt ggc tcc att gag gga act cca cac ggg ccg gtt cac ttg tgg      336
Gly Gly Gly Ser Ile Glu Gly Thr Pro His Gly Pro Val His Leu Trp
            100                 105                 110

acc ggt gac aat acg cag cct aac ttt gag gac atg gga aac ttc tac      384
Thr Gly Asp Asn Thr Gln Pro Asn Phe Glu Asp Met Gly Asn Phe Tyr
        115                 120                 125

tcc gcc gga aga gat cct att ttc ttc tcg cac cac tcc aat gtt gat      432
Ser Ala Gly Arg Asp Pro Ile Phe Phe Ser His His Ser Asn Val Asp
    130                 135                 140

agg atg tgg agt att tgg aag acc cta gct ccc aaa aac aaa gac atc      480
Arg Met Trp Ser Ile Trp Lys Thr Leu Ala Pro Lys Asn Lys Asp Ile
145                 150                 155                 160

acc gac tcc gat tgg tta gac tcc ggc ttc ctg ttc tac gac gaa aa       527
Thr Asp Ser Asp Trp Leu Asp Ser Gly Phe Leu Phe Tyr Asp Glu
                165                 170                 175


<210> SEQ ID NO 4
<211> LENGTH: 175
<212> TYPE: PRT
<213> ORGANISM: STRAWBERRY

<400> SEQUENCE: 4

Asp Pro Thr Phe Ala Leu Pro Phe Trp Asn Trp Asp Asn Pro Ala Gly
  1               5                  10                  15

Met Gln Leu Pro Ala Leu Phe Ala Asn Pro Lys Ser Pro Leu Tyr Asp
             20                  25                  30

Gln Phe Arg Ala Ala Ala His Gln Pro Pro Thr Leu Ile Asp Leu Asp
```

-continued

```
        35                  40                  45

Phe Asn Gly Thr Glu Asp Asn Thr Ser Asn Thr Thr Gln Ile Asn Ser
     50                  55                  60

Asn Leu Ser Ile Met Tyr Arg Gln Met Val Ser Asn Ala Lys Asn Ala
 65                  70                  75                  80

Gln Leu Phe Phe Gly Asn Pro Tyr Arg Ala Gly Asp Glu Pro Asp Pro
                 85                  90                  95

Gly Gly Gly Ser Ile Glu Gly Thr Pro His Gly Pro Val His Leu Trp
            100                 105                 110

Thr Gly Asp Asn Thr Gln Pro Asn Phe Glu Asp Met Gly Asn Phe Tyr
        115                 120                 125

Ser Ala Gly Arg Asp Pro Ile Phe Phe Ser His His Ser Asn Val Asp
    130                 135                 140

Arg Met Trp Ser Ile Trp Lys Thr Leu Ala Pro Lys Asn Lys Asp Ile
145                 150                 155                 160

Thr Asp Ser Asp Trp Leu Asp Ser Gly Phe Leu Phe Tyr Asp Glu
                165                 170                 175


<210> SEQ ID NO 5
<211> LENGTH: 465
<212> TYPE: DNA
<213> ORGANISM: TOBACCO
<220> FEATURE:
<221> NAME/KEY: CDS
<222> LOCATION: (1)..(465)

<400> SEQUENCE: 5

gat ccg acg ttt gcg ttg cca tat tgg aac tgg gac aat cca agc ggc       48
Asp Pro Thr Phe Ala Leu Pro Tyr Trp Asn Trp Asp Asn Pro Ser Gly
  1               5                  10                  15

atg cgt ttg gct tat atg ttc gat gtc gaa ggt tct tcc ttg tac gat       96
Met Arg Leu Ala Tyr Met Phe Asp Val Glu Gly Ser Ser Leu Tyr Asp
             20                  25                  30

gca aga cgt aat cca cat gtc cgt aat gga acc ata atc gat ctt ggt      144
Ala Arg Arg Asn Pro His Val Arg Asn Gly Thr Ile Ile Asp Leu Gly
        35                  40                  45

ttt ttc ggt gat gaa gtc aaa act aat gaa cta cag atg ata act aac      192
Phe Phe Gly Asp Glu Val Lys Thr Asn Glu Leu Gln Met Ile Thr Asn
     50                  55                  60

aac tta att tta atg tat cgt caa atg ata act aac gct cca tgc ccg      240
Asn Leu Ile Leu Met Tyr Arg Gln Met Ile Thr Asn Ala Pro Cys Pro
 65                  70                  75                  80

ctg ttg ttc ttc gga gag cct tat aga ttc gga tct aat ccc gaa cct      288
Leu Leu Phe Phe Gly Glu Pro Tyr Arg Phe Gly Ser Asn Pro Glu Pro
                 85                  90                  95

ggg atg gga acc att gaa aac atc cct cac aat ccg gtc cac att tgg      336
Gly Met Gly Thr Ile Glu Asn Ile Pro His Asn Pro Val His Ile Trp
            100                 105                 110

act ggt act gtg cgg ggg acg gat ttg ggt aat ggt gcg aaa tca tac      384
Thr Gly Thr Val Arg Gly Thr Asp Leu Gly Asn Gly Ala Lys Ser Tyr
        115                 120                 125

ggt gag gat atg ggt aat ttc tac tca act gct tta gac cca gtt ttt      432
Gly Glu Asp Met Gly Asn Phe Tyr Ser Thr Ala Leu Asp Pro Val Phe
    130                 135                 140

ttc tgc cac cac gcc aat gtc gat cgc atg tgg                          465
Phe Cys His His Ala Asn Val Asp Arg Met Trp
145                 150                 155


<210> SEQ ID NO 6
```

-continued

<211> LENGTH: 155
<212> TYPE: PRT
<213> ORGANISM: TOBACCO

<400> SEQUENCE: 6

Asp Pro Thr Phe Ala Leu Pro Tyr Trp Asn Trp Asp Asn Pro Ser Gly
1 5 10 15

Met Arg Leu Ala Tyr Met Phe Asp Val Glu Gly Ser Ser Leu Tyr Asp
20 25 30

Ala Arg Arg Asn Pro His Val Arg Asn Gly Thr Ile Ile Asp Leu Gly
35 40 45

Phe Phe Gly Asp Glu Val Lys Thr Asn Glu Leu Gln Met Ile Thr Asn
50 55 60

Asn Leu Ile Leu Met Tyr Arg Gln Met Ile Thr Asn Ala Pro Cys Pro
65 70 75 80

Leu Leu Phe Phe Gly Glu Pro Tyr Arg Phe Gly Ser Asn Pro Glu Pro
85 90 95

Gly Met Gly Thr Ile Glu Asn Ile Pro His Asn Pro Val His Ile Trp
100 105 110

Thr Gly Thr Val Arg Gly Thr Asp Leu Gly Asn Gly Ala Lys Ser Tyr
115 120 125

Gly Glu Asp Met Gly Asn Phe Tyr Ser Thr Ala Leu Asp Pro Val Phe
130 135 140

Phe Cys His His Ala Asn Val Asp Arg Met Trp
145 150 155

<210> SEQ ID NO 7
<211> LENGTH: 545
<212> TYPE: DNA
<213> ORGANISM: TOBACCO
<220> FEATURE:
<221> NAME/KEY: CDS
<222> LOCATION: (1)..(543)

<400> SEQUENCE: 7 gat ccg acg ttt ggt ttg cca tat tgg aac tgg gat cat cca aag ggc 48
Asp Pro Thr Phe Gly Leu Pro Tyr Trp Asn Trp Asp His Pro Lys Gly
1 5 10 15 atg cgt ttg cca cac atg ttt gat caa cca aat gtg tac cct gat ctt 96
Met Arg Leu Pro His Met Phe Asp Gln Pro Asn Val Tyr Pro Asp Leu
20 25 30 tac gat cca aga cgt aac caa gag cac cgc ggt tcg gta atc atg gac 144
Tyr Asp Pro Arg Arg Asn Gln Glu His Arg Gly Ser Val Ile Met Asp
35 40 45 ctt ggt cat ttt ggt caa gac gtg aaa gga act gac tta caa atg atg 192
Leu Gly His Phe Gly Gln Asp Val Lys Gly Thr Asp Leu Gln Met Met
50 55 60 agc aat aac ctt act cta atg tat cgt caa atg att acc aat tca ccg 240
Ser Asn Asn Leu Thr Leu Met Tyr Arg Gln Met Ile Thr Asn Ser Pro
65 70 75 80 tgt cca caa ctg ttt ttt ggt aag cca tat tgt acg gaa gtt gga ccc 288
Cys Pro Gln Leu Phe Phe Gly Lys Pro Tyr Cys Thr Glu Val Gly Pro
85 90 95 aaa cca ggg cag gga gct att gaa aac atc cct cat act cct gtc cac 336
Lys Pro Gly Gln Gly Ala Ile Glu Asn Ile Pro His Thr Pro Val His
100 105 110 att tgg gtt ggt agt aag cct aat gag aat aac tgt aaa aac ggt gaa 384
Ile Trp Val Gly Ser Lys Pro Asn Glu Asn Asn Cys Lys Asn Gly Glu
115 120 125

-continued

```
gat atg ggg aat ttc tat tca gct ggt aag gat cct gct ttc tat agt       432
Asp Met Gly Asn Phe Tyr Ser Ala Gly Lys Asp Pro Ala Phe Tyr Ser
    130                 135                 140

cac cat cca aat gta gat cgc atg tgg aca ata tgg aag aca tta gga       480
His His Pro Asn Val Asp Arg Met Trp Thr Ile Trp Lys Thr Leu Gly
145                 150                 155                 160

ggg aaa cgc gag gac atc aac aag cca gat tat ttg aac agt gag ttc       528
Gly Lys Arg Glu Asp Ile Asn Lys Pro Asp Tyr Leu Asn Ser Glu Phe
                165                 170                 175

ttc ttc tat gac gaa aa                                                545
Phe Phe Tyr Asp Glu
            180


<210> SEQ ID NO 8
<211> LENGTH: 181
<212> TYPE: PRT
<213> ORGANISM: TOBACCO

<400> SEQUENCE: 8

Asp Pro Thr Phe Gly Leu Pro Tyr Trp Asn Trp Asp His Pro Lys Gly
  1               5                  10                  15

Met Arg Leu Pro His Met Phe Asp Gln Pro Asn Val Tyr Pro Asp Leu
             20                  25                  30

Tyr Asp Pro Arg Arg Asn Gln Glu His Arg Gly Ser Val Ile Met Asp
        35                  40                  45

Leu Gly His Phe Gly Gln Asp Val Lys Gly Thr Asp Leu Gln Met Met
     50                  55                  60

Ser Asn Asn Leu Thr Leu Met Tyr Arg Gln Met Ile Thr Asn Ser Pro
 65                  70                  75                  80

Cys Pro Gln Leu Phe Phe Gly Lys Pro Tyr Cys Thr Glu Val Gly Pro
                 85                  90                  95

Lys Pro Gly Gln Gly Ala Ile Glu Asn Ile Pro His Thr Pro Val His
            100                 105                 110

Ile Trp Val Gly Ser Lys Pro Asn Glu Asn Asn Cys Lys Asn Gly Glu
        115                 120                 125

Asp Met Gly Asn Phe Tyr Ser Ala Gly Lys Asp Pro Ala Phe Tyr Ser
    130                 135                 140

His His Pro Asn Val Asp Arg Met Trp Thr Ile Trp Lys Thr Leu Gly
145                 150                 155                 160

Gly Lys Arg Glu Asp Ile Asn Lys Pro Asp Tyr Leu Asn Ser Glu Phe
                165                 170                 175

Phe Phe Tyr Asp Glu
            180


<210> SEQ ID NO 9
<211> LENGTH: 548
<212> TYPE: DNA
<213> ORGANISM: APRICOT
<220> FEATURE:
<221> NAME/KEY: CDS
<222> LOCATION: (1)..(546)

<400> SEQUENCE: 9

gat ccg acg ttc gcg ttg ccc ttc tgg aac tgg gac gct ccg gac ggc        48
Asp Pro Thr Phe Ala Leu Pro Phe Trp Asn Trp Asp Ala Pro Asp Gly
  1               5                  10                  15

atg tac atg cca gcc att ttc gag gac gac ccc gta ata aac cct ctc        96
Met Tyr Met Pro Ala Ile Phe Glu Asp Asp Pro Val Ile Asn Pro Leu
             20                  25                  30
```

-continued

```
tac gat gcc aac cga aac gcc aag cac cgc gtg ccg ggg acg gtt tta      144
Tyr Asp Ala Asn Arg Asn Ala Lys His Arg Val Pro Gly Thr Val Leu
        35                  40                  45

gac ctc aac tac cac ggc aag gac ggc aat acc aag gac gac aac aca      192
Asp Leu Asn Tyr His Gly Lys Asp Gly Asn Thr Lys Asp Asp Asn Thr
    50                  55                  60

ata atc aat gat aat ctc cgc acc atg aac tcg aaa atg ctg tct att      240
Ile Ile Asn Asp Asn Leu Arg Thr Met Asn Ser Lys Met Leu Ser Ile
 65                  70                  75                  80

tca agc aca gac tgg tgt tca ttc ttc ggt cac cct tac cgg gct gga      288
Ser Ser Thr Asp Trp Cys Ser Phe Phe Gly His Pro Tyr Arg Ala Gly
                85                  90                  95

tac caa cca aac ccc ggt gct ggc aat att gag agt atc cct cac aat      336
Tyr Gln Pro Asn Pro Gly Ala Gly Asn Ile Glu Ser Ile Pro His Asn
            100                 105                 110

acc gtc cac aat tgg gct ggt acg gac tca agc ttg cca cca tac act      384
Thr Val His Asn Trp Ala Gly Thr Asp Ser Ser Leu Pro Pro Tyr Thr
        115                 120                 125

ggg gag gac atg gga gtc ttc tac tct gcg ggt cga gat ccc atc ttc      432
Gly Glu Asp Met Gly Val Phe Tyr Ser Ala Gly Arg Asp Pro Ile Phe
    130                 135                 140

ttc gca cac cat gcc aac gtg gac cgc atg tgg tac ttg tgg aag aac      480
Phe Ala His His Ala Asn Val Asp Arg Met Trp Tyr Leu Trp Lys Asn
145                 150                 155                 160

aac ttt ggg gga cag gac ata gaa gac act gat tgg ttg gac agc tcg      528
Asn Phe Gly Gly Gln Asp Ile Glu Asp Thr Asp Trp Leu Asp Ser Ser
                165                 170                 175

ttt ctg ttc tat gac gaa aa                                           548
Phe Leu Phe Tyr Asp Glu
            180


<210> SEQ ID NO 10
<211> LENGTH: 182
<212> TYPE: PRT
<213> ORGANISM: APRICOT

<400> SEQUENCE: 10

Asp Pro Thr Phe Ala Leu Pro Phe Trp Asn Trp Asp Ala Pro Asp Gly
  1               5                  10                  15

Met Tyr Met Pro Ala Ile Phe Glu Asp Asp Pro Val Ile Asn Pro Leu
             20                  25                  30

Tyr Asp Ala Asn Arg Asn Ala Lys His Arg Val Pro Gly Thr Val Leu
        35                  40                  45

Asp Leu Asn Tyr His Gly Lys Asp Gly Asn Thr Lys Asp Asp Asn Thr
    50                  55                  60

Ile Ile Asn Asp Asn Leu Arg Thr Met Asn Ser Lys Met Leu Ser Ile
 65                  70                  75                  80

Ser Ser Thr Asp Trp Cys Ser Phe Phe Gly His Pro Tyr Arg Ala Gly
                85                  90                  95

Tyr Gln Pro Asn Pro Gly Ala Gly Asn Ile Glu Ser Ile Pro His Asn
            100                 105                 110

Thr Val His Asn Trp Ala Gly Thr Asp Ser Ser Leu Pro Pro Tyr Thr
        115                 120                 125

Gly Glu Asp Met Gly Val Phe Tyr Ser Ala Gly Arg Asp Pro Ile Phe
    130                 135                 140

Phe Ala His His Ala Asn Val Asp Arg Met Trp Tyr Leu Trp Lys Asn
145                 150                 155                 160

Asn Phe Gly Gly Gln Asp Ile Glu Asp Thr Asp Trp Leu Asp Ser Ser
```

-continued

```
                165                 170                 175

Phe Leu Phe Tyr Asp Glu
            180


<210> SEQ ID NO 11
<211> LENGTH: 590
<212> TYPE: DNA
<213> ORGANISM: AVOCADO
<220> FEATURE:
<221> NAME/KEY: CDS
<222> LOCATION: (1)..(588)

<400> SEQUENCE: 11

ttt ttg ccg ttc cat cgt tac tac ctc tac ttc tat gag aag atc ttg       48
Phe Leu Pro Phe His Arg Tyr Tyr Leu Tyr Phe Tyr Glu Lys Ile Leu
  1               5                  10                  15

ggc aag ttg att gga gat gag aca ttt gct ctc ccc ttc tgg aac tgg       96
Gly Lys Leu Ile Gly Asp Glu Thr Phe Ala Leu Pro Phe Trp Asn Trp
            20                  25                  30

gat gca ccg ggt gga atg cca atg ccg tcc atg tac gcc aaa cca tcg      144
Asp Ala Pro Gly Gly Met Pro Met Pro Ser Met Tyr Ala Lys Pro Ser
        35                  40                  45

tcg ccg ctc tac gac gag ctg aga gac gcc aag cac cag ccg ccg acg      192
Ser Pro Leu Tyr Asp Glu Leu Arg Asp Ala Lys His Gln Pro Pro Thr
    50                  55                  60

ctg gtg gat ctg gac tac aac ttc cag gat ccc acc aac acc gac aag      240
Leu Val Asp Leu Asp Tyr Asn Phe Gln Asp Pro Thr Asn Thr Asp Lys
 65                  70                  75                  80

cag cag ata gcc agc aac ctc tcc atc atg tac cgg cag gtg gtg tcg      288
Gln Gln Ile Ala Ser Asn Leu Ser Ile Met Tyr Arg Gln Val Val Ser
                 85                  90                  95

aat ggc aag acg gcg cag ttg ttc atg ggt gcg gcg tac cgg gcc ggc      336
Asn Gly Lys Thr Ala Gln Leu Phe Met Gly Ala Ala Tyr Arg Ala Gly
            100                 105                 110

ggg gag ccg gac ccc ggt gcc ggg tcg cta gag aac gtg ccg cat ggg      384
Gly Glu Pro Asp Pro Gly Ala Gly Ser Leu Glu Asn Val Pro His Gly
        115                 120                 125

ccg gtc cat atc tgg acc ggt gac cgg act cag ccc aac acg gag aac      432
Pro Val His Ile Trp Thr Gly Asp Arg Thr Gln Pro Asn Thr Glu Asn
    130                 135                 140

atg ggg aac ttc tac tcg gcg gca agg gac ccg atc ttc ttc gcc cac      480
Met Gly Asn Phe Tyr Ser Ala Ala Arg Asp Pro Ile Phe Phe Ala His
145                 150                 155                 160

cac tcg aac gtc gac cgg atg tgg agc gtg tgg aag acc ctg gga ggg      528
His Ser Asn Val Asp Arg Met Trp Ser Val Trp Lys Thr Leu Gly Gly
                165                 170                 175

aag agg aag gac ttc act gac cca gat tgg ctc aac tcg ggc ttc ctt      576
Lys Arg Lys Asp Phe Thr Asp Pro Asp Trp Leu Asn Ser Gly Phe Leu
            180                 185                 190

ttc tac gac gaa aa                                                   590
Phe Tyr Asp Glu
        195


<210> SEQ ID NO 12
<211> LENGTH: 196
<212> TYPE: PRT
<213> ORGANISM: AVOCADO

<400> SEQUENCE: 12

Phe Leu Pro Phe His Arg Tyr Tyr Leu Tyr Phe Tyr Glu Lys Ile Leu
  1               5                  10                  15
```

-continued

```
Gly Lys Leu Ile Gly Asp Glu Thr Phe Ala Leu Pro Phe Trp Asn Trp
            20                  25                  30

Asp Ala Pro Gly Gly Met Pro Met Pro Ser Met Tyr Ala Lys Pro Ser
        35                  40                  45

Ser Pro Leu Tyr Asp Glu Leu Arg Asp Ala Lys His Gln Pro Pro Thr
    50                  55                  60

Leu Val Asp Leu Asp Tyr Asn Phe Gln Asp Pro Thr Asn Thr Asp Lys
65                  70                  75                  80

Gln Gln Ile Ala Ser Asn Leu Ser Ile Met Tyr Arg Gln Val Val Ser
                85                  90                  95

Asn Gly Lys Thr Ala Gln Leu Phe Met Gly Ala Ala Tyr Arg Ala Gly
            100                 105                 110

Gly Glu Pro Asp Pro Gly Ala Gly Ser Leu Glu Asn Val Pro His Gly
        115                 120                 125

Pro Val His Ile Trp Thr Gly Asp Arg Thr Gln Pro Asn Thr Glu Asn
    130                 135                 140

Met Gly Asn Phe Tyr Ser Ala Ala Arg Asp Pro Ile Phe Phe Ala His
145                 150                 155                 160

His Ser Asn Val Asp Arg Met Trp Ser Val Trp Lys Thr Leu Gly Gly
                165                 170                 175

Lys Arg Lys Asp Phe Thr Asp Pro Asp Trp Leu Asn Ser Gly Phe Leu
            180                 185                 190

Phe Tyr Asp Glu
        195


<210> SEQ ID NO 13
<211> LENGTH: 590
<212> TYPE: DNA
<213> ORGANISM: CHERRY
<220> FEATURE:
<221> NAME/KEY: CDS
<222> LOCATION: (1)..(588)

<400> SEQUENCE: 13

ttc ctg ccg ttt cac cgt ttc tac ctc tac ttc tat gag aag atc ttg       48
Phe Leu Pro Phe His Arg Phe Tyr Leu Tyr Phe Tyr Glu Lys Ile Leu
  1               5                  10                  15

ggc aag ttg att gga gat gag aca ttt gct ctc ccc ttc tgg aac tgg       96
Gly Lys Leu Ile Gly Asp Glu Thr Phe Ala Leu Pro Phe Trp Asn Trp
            20                  25                  30

gac gca ccg gac gga atg cca atg ccg tcc atg tac gcc aat tct tcg      144
Asp Ala Pro Asp Gly Met Pro Met Pro Ser Met Tyr Ala Asn Ser Ser
        35                  40                  45

gcg ccg ttc tac gac aag ctg aga gat gcc aag cac cag ccg ccg acg      192
Ala Pro Phe Tyr Asp Lys Leu Arg Asp Ala Lys His Gln Pro Pro Thr
    50                  55                  60

ctt gtg gat ttg gac tac aac ttc caa gat ccc acc aac acc gat atg      240
Leu Val Asp Leu Asp Tyr Asn Phe Gln Asp Pro Thr Asn Thr Asp Met
 65                  70                  75                  80

cag cag ata tcc agc aac ctg tcc gtc atg tac cag cag gtg gtg tcg      288
Gln Gln Ile Ser Ser Asn Leu Ser Val Met Tyr Gln Gln Val Val Ser
                85                  90                  95

aat gcc aag acg gcg gag ttg ttc atg ggt gcg gcg tac cgg gcc gga      336
Asn Ala Lys Thr Ala Glu Leu Phe Met Gly Ala Ala Tyr Arg Ala Gly
            100                 105                 110

ggg gag ccg gac tcc ggt gcc ggg tcg cta gag aac gtg ccg cat ggg      384
Gly Glu Pro Asp Ser Gly Ala Gly Ser Leu Glu Asn Val Pro His Gly
        115                 120                 125
```

```
ccg atc cat atc tgg acc ggt gac cgg act caa ccc aac ccg gag aac      432
Pro Ile His Ile Trp Thr Gly Asp Arg Thr Gln Pro Asn Pro Glu Asn
    130                 135                 140

atg ggg aac ttc tac tcg gcg gga agg gac ccc atc ttc ttc gcc cac      480
Met Gly Asn Phe Tyr Ser Ala Gly Arg Asp Pro Ile Phe Phe Ala His
145                 150                 155                 160

cac tcg aac gtc gac cgg atg tgg gac gtg tgg aag acc ctg gga ggg      528
His Ser Asn Val Asp Arg Met Trp Asp Val Trp Lys Thr Leu Gly Gly
                165                 170                 175

aag agg aag gac ttc act gac gcg gat tgg ctc aac gcg ggc ttc ctc      576
Lys Arg Lys Asp Phe Thr Asp Ala Asp Trp Leu Asn Ala Gly Phe Leu
            180                 185                 190

ttc tac gat gag aa                                                   590
Phe Tyr Asp Glu
        195


<210> SEQ ID NO 14
<211> LENGTH: 196
<212> TYPE: PRT
<213> ORGANISM: CHERRY

<400> SEQUENCE: 14

Phe Leu Pro Phe His Arg Phe Tyr Leu Tyr Phe Tyr Glu Lys Ile Leu
  1               5                  10                  15

Gly Lys Leu Ile Gly Asp Glu Thr Phe Ala Leu Pro Phe Trp Asn Trp
            20                  25                  30

Asp Ala Pro Asp Gly Met Pro Met Pro Ser Met Tyr Ala Asn Ser Ser
        35                  40                  45

Ala Pro Phe Tyr Asp Lys Leu Arg Asp Ala Lys His Gln Pro Pro Thr
    50                  55                  60

Leu Val Asp Leu Asp Tyr Asn Phe Gln Asp Pro Thr Asn Thr Asp Met
 65                  70                  75                  80

Gln Gln Ile Ser Ser Asn Leu Ser Val Met Tyr Gln Gln Val Val Ser
                85                  90                  95

Asn Ala Lys Thr Ala Glu Leu Phe Met Gly Ala Ala Tyr Arg Ala Gly
            100                 105                 110

Gly Glu Pro Asp Ser Gly Ala Gly Ser Leu Glu Asn Val Pro His Gly
        115                 120                 125

Pro Ile His Ile Trp Thr Gly Asp Arg Thr Gln Pro Asn Pro Glu Asn
    130                 135                 140

Met Gly Asn Phe Tyr Ser Ala Gly Arg Asp Pro Ile Phe Phe Ala His
145                 150                 155                 160

His Ser Asn Val Asp Arg Met Trp Asp Val Trp Lys Thr Leu Gly Gly
                165                 170                 175

Lys Arg Lys Asp Phe Thr Asp Ala Asp Trp Leu Asn Ala Gly Phe Leu
            180                 185                 190

Phe Tyr Asp Glu
        195


<210> SEQ ID NO 15
<211> LENGTH: 441
<212> TYPE: DNA
<213> ORGANISM: CHERRY
<220> FEATURE:
<221> NAME/KEY: CDS
<222> LOCATION: (1)..(441)

<400> SEQUENCE: 15

gat ccg acg ttt gct ttg ccg ttc tgg aac tgg gac gcg ccg gcc ggc       48
```

-continued

```
Asp Pro Thr Phe Ala Leu Pro Phe Trp Asn Trp Asp Ala Pro Ala Gly
  1               5                  10                  15

atg caa ctg cct gcc ttg tac gcc aac ccg gac tct ccc ctc tac gac       96
Met Gln Leu Pro Ala Leu Tyr Ala Asn Pro Asp Ser Pro Leu Tyr Asp
             20                  25                  30

gag ctc cga gcc gcc acc cac cag ccg ccg gca ctc ctc gat ctc gaa      144
Glu Leu Arg Ala Ala Thr His Gln Pro Pro Ala Leu Leu Asp Leu Glu
         35                  40                  45

ttc aac ggc acg gac gag aaa gtc aac aga gaa gct caa gtc aac tcc      192
Phe Asn Gly Thr Asp Glu Lys Val Asn Arg Glu Ala Gln Val Asn Ser
     50                  55                  60

aat ctc aag atc atg tac agg cag atg gtg tcc aac gcc aag aaa ccg      240
Asn Leu Lys Ile Met Tyr Arg Gln Met Val Ser Asn Ala Lys Lys Pro
 65                  70                  75                  80

ctg ttg ttc ttt ggc tgg cct tat agg gct ggg act gaa gcg gac ccc      288
Leu Leu Phe Phe Gly Trp Pro Tyr Arg Ala Gly Thr Glu Ala Asp Pro
                 85                  90                  95

gga ccc ggt tca gtt gag aca act ccg cac ggg ccg gtt cat tta tgg      336
Gly Pro Gly Ser Val Glu Thr Thr Pro His Gly Pro Val His Leu Trp
            100                 105                 110

acg gga gat aac acc cag cca aac ttt gag aac atg ggg aat ttt tat      384
Thr Gly Asp Asn Thr Gln Pro Asn Phe Glu Asn Met Gly Asn Phe Tyr
        115                 120                 125

tcg gca gcc agg gat cct ata ttt ttt tcg cac cac tcc aac gtc gat      432
Ser Ala Ala Arg Asp Pro Ile Phe Phe Ser His His Ser Asn Val Asp
    130                 135                 140

cgc atg tgg                                                          441
Arg Met Trp
145


<210> SEQ ID NO 16
<211> LENGTH: 147
<212> TYPE: PRT
<213> ORGANISM: CHERRY

<400> SEQUENCE: 16

Asp Pro Thr Phe Ala Leu Pro Phe Trp Asn Trp Asp Ala Pro Ala Gly
  1               5                  10                  15

Met Gln Leu Pro Ala Leu Tyr Ala Asn Pro Asp Ser Pro Leu Tyr Asp
             20                  25                  30

Glu Leu Arg Ala Ala Thr His Gln Pro Pro Ala Leu Leu Asp Leu Glu
         35                  40                  45

Phe Asn Gly Thr Asp Glu Lys Val Asn Arg Glu Ala Gln Val Asn Ser
     50                  55                  60

Asn Leu Lys Ile Met Tyr Arg Gln Met Val Ser Asn Ala Lys Lys Pro
 65                  70                  75                  80

Leu Leu Phe Phe Gly Trp Pro Tyr Arg Ala Gly Thr Glu Ala Asp Pro
                 85                  90                  95

Gly Pro Gly Ser Val Glu Thr Thr Pro His Gly Pro Val His Leu Trp
            100                 105                 110

Thr Gly Asp Asn Thr Gln Pro Asn Phe Glu Asn Met Gly Asn Phe Tyr
        115                 120                 125

Ser Ala Ala Arg Asp Pro Ile Phe Phe Ser His His Ser Asn Val Asp
    130                 135                 140

Arg Met Trp
145


<210> SEQ ID NO 17
```

```
<211> LENGTH: 548
<212> TYPE: DNA
<213> ORGANISM: PEACH
<220> FEATURE:
<221> NAME/KEY: CDS
<222> LOCATION: (1)..(546)

<400> SEQUENCE: 17

gat ccg acg ttc gct ttg ccc ttc tgg aac tgg gac gct cct gac ggc      48
Asp Pro Thr Phe Ala Leu Pro Phe Trp Asn Trp Asp Ala Pro Asp Gly
  1               5                  10                  15

atg tac atg cca gcc att ttc gag gac gac ccc gta tta aac cct ctc      96
Met Tyr Met Pro Ala Ile Phe Glu Asp Asp Pro Val Leu Asn Pro Leu
             20                  25                  30

tac gat gcc aac cga aac gcc aag cac cgt gtg ccg ggg acg gtt tta     144
Tyr Asp Ala Asn Arg Asn Ala Lys His Arg Val Pro Gly Thr Val Leu
         35                  40                  45

gac ctc aac tac cac ggc aag gac gac aat acc aag gac gac gac aca     192
Asp Leu Asn Tyr His Gly Lys Asp Asp Asn Thr Lys Asp Asp Asp Thr
     50                  55                  60

ata atc cgg cat aat ctc gtc acc atg aac tcg caa atg ctg tct att     240
Ile Ile Arg His Asn Leu Val Thr Met Asn Ser Gln Met Leu Ser Ile
 65                  70                  75                  80

tca agc aca gac tgg tgc tca ttc ttc ggt cat cct tac cgc gct gga     288
Ser Ser Thr Asp Trp Cys Ser Phe Phe Gly His Pro Tyr Arg Ala Gly
                 85                  90                  95

tac caa cca aac ccc ggt gct ggc aat att gag aaa atc cct cac agt     336
Tyr Gln Pro Asn Pro Gly Ala Gly Asn Ile Glu Lys Ile Pro His Ser
            100                 105                 110

acc gtc cac aat tgg act ggt acg gac tca agt ttg cca cca aac act     384
Thr Val His Asn Trp Thr Gly Thr Asp Ser Ser Leu Pro Pro Asn Thr
        115                 120                 125

ggg gag gac atg gga gtt tta tac tct gcg ggt aga gat ccc att ttt     432
Gly Glu Asp Met Gly Val Leu Tyr Ser Ala Gly Arg Asp Pro Ile Phe
    130                 135                 140

ttc gca cac cat gcc aac gtg gac cgc atg tgg tac ttg tgg aag aac     480
Phe Ala His His Ala Asn Val Asp Arg Met Trp Tyr Leu Trp Lys Asn
145                 150                 155                 160

aac ttt ggg gga cag gac ata gaa gac act gat tgg ctt gac agc tcg     528
Asn Phe Gly Gly Gln Asp Ile Glu Asp Thr Asp Trp Leu Asp Ser Ser
                165                 170                 175

ttt ctg ttc tac gac gaa aa                                          548
Phe Leu Phe Tyr Asp Glu
            180


<210> SEQ ID NO 18
<211> LENGTH: 182
<212> TYPE: PRT
<213> ORGANISM: PEACH

<400> SEQUENCE: 18

Asp Pro Thr Phe Ala Leu Pro Phe Trp Asn Trp Asp Ala Pro Asp Gly
  1               5                  10                  15

Met Tyr Met Pro Ala Ile Phe Glu Asp Asp Pro Val Leu Asn Pro Leu
             20                  25                  30

Tyr Asp Ala Asn Arg Asn Ala Lys His Arg Val Pro Gly Thr Val Leu
         35                  40                  45

Asp Leu Asn Tyr His Gly Lys Asp Asp Asn Thr Lys Asp Asp Asp Thr
     50                  55                  60

Ile Ile Arg His Asn Leu Val Thr Met Asn Ser Gln Met Leu Ser Ile
 65                  70                  75                  80
```

```
Ser Ser Thr Asp Trp Cys Ser Phe Phe Gly His Pro Tyr Arg Ala Gly
                 85                  90                  95

Tyr Gln Pro Asn Pro Gly Ala Gly Asn Ile Glu Lys Ile Pro His Ser
            100                 105                 110

Thr Val His Asn Trp Thr Gly Thr Asp Ser Ser Leu Pro Pro Asn Thr
        115                 120                 125

Gly Glu Asp Met Gly Val Leu Tyr Ser Ala Gly Arg Asp Pro Ile Phe
    130                 135                 140

Phe Ala His His Ala Asn Val Asp Arg Met Trp Tyr Leu Trp Lys Asn
145                 150                 155                 160

Asn Phe Gly Gly Gln Asp Ile Glu Asp Thr Asp Trp Leu Asp Ser Ser
                165                 170                 175

Phe Leu Phe Tyr Asp Glu
            180


<210> SEQ ID NO 19
<211> LENGTH: 465
<212> TYPE: DNA
<213> ORGANISM: PEAR
<220> FEATURE:
<221> NAME/KEY: CDS
<222> LOCATION: (1)..(465)

<400> SEQUENCE: 19

gat ccg acg ttt gcg ttg ccc ttt tgg aac tgg gat gct cca gaa ggg       48
Asp Pro Thr Phe Ala Leu Pro Phe Trp Asn Trp Asp Ala Pro Glu Gly
  1               5                  10                  15

atg tac atg cca acc ata ttt gag gag gat ggt gta att aac cct ctc       96
Met Tyr Met Pro Thr Ile Phe Glu Glu Asp Gly Val Ile Asn Pro Leu
             20                  25                  30

tat gat ccc tac cga aat gac aag cac cgg cgt cca ggg aca atc gtg      144
Tyr Asp Pro Tyr Arg Asn Asp Lys His Arg Arg Pro Gly Thr Ile Val
         35                  40                  45

gac ctc aac tac ggg cta ggc atg gac aac aac acc cga gac act gac      192
Asp Leu Asn Tyr Gly Leu Gly Met Asp Asn Asn Thr Arg Asp Thr Asp
     50                  55                  60

aca ata gag aat tat aat ctc ttc acc atg cac aac aaa atg ttg agt      240
Thr Ile Glu Asn Tyr Asn Leu Phe Thr Met His Asn Lys Met Leu Ser
 65                  70                  75                  80

ggt gct cgc tgg gac tgg tgc tta ttc ttt ggc cat cct tac agg gca      288
Gly Ala Arg Trp Asp Trp Cys Leu Phe Phe Gly His Pro Tyr Arg Ala
                 85                  90                  95

ggg gac aac cca aat cca gga gcc ggc aac atc gag ctt gtt ccc cat      336
Gly Asp Asn Pro Asn Pro Gly Ala Gly Asn Ile Glu Leu Val Pro His
            100                 105                 110

aac acc gtc cac gat tgg act ggc act act caa gac tca acc cag ggt      384
Asn Thr Val His Asp Trp Thr Gly Thr Thr Gln Asp Ser Thr Gln Gly
        115                 120                 125

ggg gtg gac atg ggg ata ttc tac tct gca ggt aga gat cca gtg ttt      432
Gly Val Asp Met Gly Ile Phe Tyr Ser Ala Gly Arg Asp Pro Val Phe
    130                 135                 140

tac gct cac cat gcc aac gtc gat cgc atg tgg                          465
Tyr Ala His His Ala Asn Val Asp Arg Met Trp
145                 150                 155


<210> SEQ ID NO 20
<211> LENGTH: 155
<212> TYPE: PRT
<213> ORGANISM: PEAR
```

-continued

<400> SEQUENCE: 20

```
Asp Pro Thr Phe Ala Leu Pro Phe Trp Asn Trp Asp Ala Pro Glu Gly
  1               5                  10                  15

Met Tyr Met Pro Thr Ile Phe Glu Glu Asp Gly Val Ile Asn Pro Leu
             20                  25                  30

Tyr Asp Pro Tyr Arg Asn Asp Lys His Arg Arg Pro Gly Thr Ile Val
         35                  40                  45

Asp Leu Asn Tyr Gly Leu Gly Met Asp Asn Asn Thr Arg Asp Thr Asp
     50                  55                  60

Thr Ile Glu Asn Tyr Asn Leu Phe Thr Met His Asn Lys Met Leu Ser
 65                  70                  75                  80

Gly Ala Arg Trp Asp Trp Cys Leu Phe Phe Gly His Pro Tyr Arg Ala
                 85                  90                  95

Gly Asp Asn Pro Asn Pro Gly Ala Gly Asn Ile Glu Leu Val Pro His
            100                 105                 110

Asn Thr Val His Asp Trp Thr Gly Thr Thr Gln Asp Ser Thr Gln Gly
        115                 120                 125

Gly Val Asp Met Gly Ile Phe Tyr Ser Ala Gly Arg Asp Pro Val Phe
    130                 135                 140

Tyr Ala His His Ala Asn Val Asp Arg Met Trp
145                 150                 155
```

<210> SEQ ID NO 21
<211> LENGTH: 527
<212> TYPE: DNA
<213> ORGANISM: PEAR
<220> FEATURE:
<221> NAME/KEY: CDS
<222> LOCATION: (1)..(525)

<400> SEQUENCE: 21

```
gat ccg acg ttt gct ttg ccg ttt tgg aac tac gac gcg cca gct ggc       48
Asp Pro Thr Phe Ala Leu Pro Phe Trp Asn Tyr Asp Ala Pro Ala Gly
  1               5                  10                  15

atg caa atc cct gcc ttg tac act aac ccg gac tct cca ctt tac gac       96
Met Gln Ile Pro Ala Leu Tyr Thr Asn Pro Asp Ser Pro Leu Tyr Asp
             20                  25                  30

aag ttc cgc gct gcc agc cat cag ccg ccg act ctc atc gat ctt gac      144
Lys Phe Arg Ala Ala Ser His Gln Pro Pro Thr Leu Ile Asp Leu Asp
         35                  40                  45

ttc aac ggc acg gac gaa aca att tcc aac gat gct cga atc gac gcc      192
Phe Asn Gly Thr Asp Glu Thr Ile Ser Asn Asp Ala Arg Ile Asp Ala
     50                  55                  60

aac ctc aaa ctc atg tat agg cag atg att tcc aac gcc aag aaa cag      240
Asn Leu Lys Leu Met Tyr Arg Gln Met Ile Ser Asn Ala Lys Lys Gln
 65                  70                  75                  80

ctg ttg ttc ttt ggt gcg ccc ttg agg gct ggc act gaa cca gat cca      288
Leu Leu Phe Phe Gly Ala Pro Leu Arg Ala Gly Thr Glu Pro Asp Pro
                 85                  90                  95

ggg cag ggt tca atc gaa acg gcc cca cat ggt ccg gtt cat tta tgg      336
Gly Gln Gly Ser Ile Glu Thr Ala Pro His Gly Pro Val His Leu Trp
            100                 105                 110

acc gga gat aac acg caa cct aat att gaa gac atg ggg aat ttt tac      384
Thr Gly Asp Asn Thr Gln Pro Asn Ile Glu Asp Met Gly Asn Phe Tyr
        115                 120                 125

tcc gct gga agg gat cca ata ttt ttt gcg cac cat tcg aat gtg gat      432
Ser Ala Gly Arg Asp Pro Ile Phe Phe Ala His His Ser Asn Val Asp
    130                 135                 140
```

-continued

```
cga atg tgg aat att tgg aaa agt tta ggg act aaa gat aaa gat att      480
Arg Met Trp Asn Ile Trp Lys Ser Leu Gly Thr Lys Asp Lys Asp Ile
145                 150                 155                 160

aac gat ccg gat tgg ttg gat tcg ggg ttc ttg ttc tac gat gaa aa       527
Asn Asp Pro Asp Trp Leu Asp Ser Gly Phe Leu Phe Tyr Asp Glu
                165                 170                 175
```

<210> SEQ ID NO 22
<211> LENGTH: 175
<212> TYPE: PRT
<213> ORGANISM: PEAR

<400> SEQUENCE: 22

```
Asp Pro Thr Phe Ala Leu Pro Phe Trp Asn Tyr Asp Ala Pro Ala Gly
  1               5                  10                  15

Met Gln Ile Pro Ala Leu Tyr Thr Asn Pro Asp Ser Pro Leu Tyr Asp
             20                  25                  30

Lys Phe Arg Ala Ala Ser His Gln Pro Pro Thr Leu Ile Asp Leu Asp
         35                  40                  45

Phe Asn Gly Thr Asp Glu Thr Ile Ser Asn Asp Ala Arg Ile Asp Ala
     50                  55                  60

Asn Leu Lys Leu Met Tyr Arg Gln Met Ile Ser Asn Ala Lys Lys Gln
 65                  70                  75                  80

Leu Leu Phe Phe Gly Ala Pro Leu Arg Ala Gly Thr Glu Pro Asp Pro
                 85                  90                  95

Gly Gln Gly Ser Ile Glu Thr Ala Pro His Gly Pro Val His Leu Trp
            100                 105                 110

Thr Gly Asp Asn Thr Gln Pro Asn Ile Glu Asp Met Gly Asn Phe Tyr
        115                 120                 125

Ser Ala Gly Arg Asp Pro Ile Phe Phe Ala His His Ser Asn Val Asp
    130                 135                 140

Arg Met Trp Asn Ile Trp Lys Ser Leu Gly Thr Lys Asp Lys Asp Ile
145                 150                 155                 160

Asn Asp Pro Asp Trp Leu Asp Ser Gly Phe Leu Phe Tyr Asp Glu
                165                 170                 175
```

<210> SEQ ID NO 23
<211> LENGTH: 674
<212> TYPE: DNA
<213> ORGANISM: COFFEE
<220> FEATURE:
<221> NAME/KEY: CDS
<222> LOCATION: (1)..(672)

<400> SEQUENCE: 23

```
ctg cat tgt gcg tat tgc aat ggt gcc tac gtc caa cca ggc tct gat       48
Leu His Cys Ala Tyr Cys Asn Gly Ala Tyr Val Gln Pro Gly Ser Asp
  1               5                  10                  15

caa gaa att tca gtc cat tac tcg tgg tta ttc ttc cct ttt cat aga       96
Gln Glu Ile Ser Val His Tyr Ser Trp Leu Phe Phe Pro Phe His Arg
             20                  25                  30

tgg tat ttg tac ttc tat gaa gga atc ttg gga aag cta ata ggc gat      144
Trp Tyr Leu Tyr Phe Tyr Glu Gly Ile Leu Gly Lys Leu Ile Gly Asp
         35                  40                  45

ccc agt ttt gga ctg ccc ttt tgg aac tgg gac aac att ggt ggc atg      192
Pro Ser Phe Gly Leu Pro Phe Trp Asn Trp Asp Asn Ile Gly Gly Met
     50                  55                  60

acc ata ccg tcc ata ttt atg gac caa tcg tca gca ttg tat aac gaa      240
Thr Ile Pro Ser Ile Phe Met Asp Gln Ser Ser Ala Leu Tyr Asn Glu
 65                  70                  75                  80
```

-continued

```
aat cgt aac caa agt cat ctg cca cca acg gtc gtg gac ttg ggg tat      288
Asn Arg Asn Gln Ser His Leu Pro Pro Thr Val Val Asp Leu Gly Tyr
                 85                  90                  95

aat ggt acg gat aga gat gca aca tgc aca gaa agg ata gaa aac aat      336
Asn Gly Thr Asp Arg Asp Ala Thr Cys Thr Glu Arg Ile Glu Asn Asn
            100                 105                 110

ttg gcg atc atg tac cgt caa atg gtc tct aat gcc acc act ggc aga      384
Leu Ala Ile Met Tyr Arg Gln Met Val Ser Asn Ala Thr Thr Gly Arg
        115                 120                 125

gat ttc ttt gga aag gaa tac cgg gcc ggc gat gag ccc aat gcc ttt      432
Asp Phe Phe Gly Lys Glu Tyr Arg Ala Gly Asp Glu Pro Asn Ala Phe
    130                 135                 140

gct ggc gca ggg tcc atc gag gcc agt ccc cat att cca ctc cac agg      480
Ala Gly Ala Gly Ser Ile Glu Ala Ser Pro His Ile Pro Leu His Arg
145                 150                 155                 160

tgg gtc ggc gat cca agg caa cca aat ggt gaa gat ttg ggt aat ttc      528
Trp Val Gly Asp Pro Arg Gln Pro Asn Gly Glu Asp Leu Gly Asn Phe
                165                 170                 175

tac tca gct gga aga gat gtt ctg ttc tat agc cat cat gca aat gtg      576
Tyr Ser Ala Gly Arg Asp Val Leu Phe Tyr Ser His His Ala Asn Val
            180                 185                 190

gac cgg atg tgg aca att tgg caa caa ttg gga ggt aaa agg aag gag      624
Asp Arg Met Trp Thr Ile Trp Gln Gln Leu Gly Gly Lys Arg Lys Glu
        195                 200                 205

gtc ccc gat cca gat tgg ctg aat tct tcc ttc att ttc tac gac gaa      672
Val Pro Asp Pro Asp Trp Leu Asn Ser Ser Phe Ile Phe Tyr Asp Glu
    210                 215                 220

aa                                                                   674


<210> SEQ ID NO 24
<211> LENGTH: 224
<212> TYPE: PRT
<213> ORGANISM: COFFEE

<400> SEQUENCE: 24

Leu His Cys Ala Tyr Cys Asn Gly Ala Tyr Val Gln Pro Gly Ser Asp
  1               5                  10                  15

Gln Glu Ile Ser Val His Tyr Ser Trp Leu Phe Phe Pro Phe His Arg
             20                  25                  30

Trp Tyr Leu Tyr Phe Tyr Glu Gly Ile Leu Gly Lys Leu Ile Gly Asp
         35                  40                  45

Pro Ser Phe Gly Leu Pro Phe Trp Asn Trp Asp Asn Ile Gly Gly Met
     50                  55                  60

Thr Ile Pro Ser Ile Phe Met Asp Gln Ser Ser Ala Leu Tyr Asn Glu
 65                  70                  75                  80

Asn Arg Asn Gln Ser His Leu Pro Pro Thr Val Val Asp Leu Gly Tyr
                 85                  90                  95

Asn Gly Thr Asp Arg Asp Ala Thr Cys Thr Glu Arg Ile Glu Asn Asn
            100                 105                 110

Leu Ala Ile Met Tyr Arg Gln Met Val Ser Asn Ala Thr Thr Gly Arg
        115                 120                 125

Asp Phe Phe Gly Lys Glu Tyr Arg Ala Gly Asp Glu Pro Asn Ala Phe
    130                 135                 140

Ala Gly Ala Gly Ser Ile Glu Ala Ser Pro His Ile Pro Leu His Arg
145                 150                 155                 160

Trp Val Gly Asp Pro Arg Gln Pro Asn Gly Glu Asp Leu Gly Asn Phe
                165                 170                 175
```

-continued

```
Tyr Ser Ala Gly Arg Asp Val Leu Phe Tyr Ser His His Ala Asn Val
            180                 185                 190

Asp Arg Met Trp Thr Ile Trp Gln Gln Leu Gly Gly Lys Arg Lys Glu
        195                 200                 205

Val Pro Asp Pro Asp Trp Leu Asn Ser Ser Phe Ile Phe Tyr Asp Glu
    210                 215                 220


<210> SEQ ID NO: 25
<211> LENGTH: 667
<212> TYPE: DNA
<213> ORGANISM: COFFEE
<220> FEATURE:
<221> NAME/KEY: CDS
<222> LOCATION: (3)..(665)

<400> SEQUENCE: 25

tg cat tgt gcg tat tgc aac ggt gcc tac atc caa tca ggc tct gat        47
   His Cys Ala Tyr Cys Asn Gly Ala Tyr Ile Gln Ser Gly Ser Asp
     1               5                  10                  15

caa gaa att caa gtc cat aac tcg tgg cta ttc ttt cct ttt cat aga       95
Gln Glu Ile Gln Val His Asn Ser Trp Leu Phe Phe Pro Phe His Arg
                 20                  25                  30

tgg tat ttg tac ttc tat gaa aga atc ttg gga aag cta ata ggc gat      143
Trp Tyr Leu Tyr Phe Tyr Glu Arg Ile Leu Gly Lys Leu Ile Gly Asp
             35                  40                  45

ccc agt ttt gga ctg ccc ttt tgg aac tgg gac aac att ggt ggt atg      191
Pro Ser Phe Gly Leu Pro Phe Trp Asn Trp Asp Asn Ile Gly Gly Met
         50                  55                  60

acc cta ccg tcc ata ttt cag gac caa tcg tca gca ctg tat aac caa      239
Thr Leu Pro Ser Ile Phe Gln Asp Gln Ser Ser Ala Leu Tyr Asn Gln
     65                  70                  75

aat cgt aac caa agt cat ctg cca cca aca gtc gtg gac ttg ggg tat      287
Asn Arg Asn Gln Ser His Leu Pro Pro Thr Val Val Asp Leu Gly Tyr
 80                  85                  90                  95

aat ggt acg gat aca gat gca aca gac ata gaa agg ata aaa aac aat      335
Asn Gly Thr Asp Thr Asp Ala Thr Asp Ile Glu Arg Ile Lys Asn Asn
                100                 105                 110

ttg gca atc atg tac cgt caa atg gtc act aat tcc acc act gcc aaa      383
Leu Ala Ile Met Tyr Arg Gln Met Val Thr Asn Ser Thr Thr Ala Lys
            115                 120                 125

gat ttc ttt gga aag gaa tac cgg gcc ggc gat gcg ccc agc ccg ggt      431
Asp Phe Phe Gly Lys Glu Tyr Arg Ala Gly Asp Ala Pro Ser Pro Gly
        130                 135                 140

gca ggg tcc atc gag gcc att ccc cat atc cca atc cac agg tgg gtc      479
Ala Gly Ser Ile Glu Ala Ile Pro His Ile Pro Ile His Arg Trp Val
    145                 150                 155

ggc gat cca agg cag cca aat ggt gaa gat atg ggt aat ttc tac tca      527
Gly Asp Pro Arg Gln Pro Asn Gly Glu Asp Met Gly Asn Phe Tyr Ser
160                 165                 170                 175

gct gga aga gat att gtg ttc tat agc cat cat gca aat gtg gac cgg      575
Ala Gly Arg Asp Ile Val Phe Tyr Ser His His Ala Asn Val Asp Arg
                180                 185                 190

atg tgg aca att tgg cag caa ttg gga ggt aaa agg aag gag gtc ccc      623
Met Trp Thr Ile Trp Gln Gln Leu Gly Gly Lys Arg Lys Glu Val Pro
            195                 200                 205

gat cca gat tgg ctg aat tct tcc ttc att ttc tac gat gaa aa           667
Asp Pro Asp Trp Leu Asn Ser Ser Phe Ile Phe Tyr Asp Glu
        210                 215                 220


<210> SEQ ID NO: 26
```

```
<211> LENGTH: 221
<212> TYPE: PRT
<213> ORGANISM: COFFEE

<400> SEQUENCE: 26

His Cys Ala Tyr Cys Asn Gly Ala Tyr Ile Gln Ser Gly Ser Asp Gln
  1               5                  10                  15

Glu Ile Gln Val His Asn Ser Trp Leu Phe Phe Pro Phe His Arg Trp
             20                  25                  30

Tyr Leu Tyr Phe Tyr Glu Arg Ile Leu Gly Lys Leu Ile Gly Asp Pro
         35                  40                  45

Ser Phe Gly Leu Pro Phe Trp Asn Trp Asp Asn Ile Gly Gly Met Thr
     50                  55                  60

Leu Pro Ser Ile Phe Gln Asp Gln Ser Ser Ala Leu Tyr Asn Gln Asn
 65                  70                  75                  80

Arg Asn Gln Ser His Leu Pro Pro Thr Val Val Asp Leu Gly Tyr Asn
                 85                  90                  95

Gly Thr Asp Thr Asp Ala Thr Asp Ile Glu Arg Ile Lys Asn Asn Leu
            100                 105                 110

Ala Ile Met Tyr Arg Gln Met Val Thr Asn Ser Thr Thr Ala Lys Asp
        115                 120                 125

Phe Phe Gly Lys Glu Tyr Arg Ala Gly Asp Ala Pro Ser Pro Gly Ala
    130                 135                 140

Gly Ser Ile Glu Ala Ile Pro His Ile Pro Ile His Arg Trp Val Gly
145                 150                 155                 160

Asp Pro Arg Gln Pro Asn Gly Glu Asp Met Gly Asn Phe Tyr Ser Ala
                165                 170                 175

Gly Arg Asp Ile Val Phe Tyr Ser His His Ala Asn Val Asp Arg Met
            180                 185                 190

Trp Thr Ile Trp Gln Gln Leu Gly Gly Lys Arg Lys Glu Val Pro Asp
        195                 200                 205

Pro Asp Trp Leu Asn Ser Ser Phe Ile Phe Tyr Asp Glu
    210                 215                 220


<210> SEQ ID NO: 27
<211> LENGTH: 588
<212> TYPE: DNA
<213> ORGANISM: APPLE
<220> FEATURE:
<221> NAME/KEY: CDS
<222> LOCATION: (1)..(588)

<400> SEQUENCE: 27

cat tgc gcg tat tgc gac ggc gcg tac gac caa gtc ggc ttc ccc aac       48
His Cys Ala Tyr Cys Asp Gly Ala Tyr Asp Gln Val Gly Phe Pro Asn
  1               5                  10                  15

ctc gag ctc caa atc cat caa tgc tgg ctt ttc ttc ccc ttc cat cgt       96
Leu Glu Leu Gln Ile His Gln Cys Trp Leu Phe Phe Pro Phe His Arg
             20                  25                  30

tac tac cta tac ttc cac gaa aga atc ttg gcc aaa ctc ata gac gat      144
Tyr Tyr Leu Tyr Phe His Glu Arg Ile Leu Ala Lys Leu Ile Asp Asp
         35                  40                  45

ccg acg ttc gcg ttg ccg ttt tgg aac tgg gac gcg cca gct ggc atg      192
Pro Thr Phe Ala Leu Pro Phe Trp Asn Trp Asp Ala Pro Ala Gly Met
     50                  55                  60

caa ctc cct gcc ttg ttc gct aac ccg gac tct ccg ctt tac gac gag      240
Gln Leu Pro Ala Leu Phe Ala Asn Pro Asp Ser Pro Leu Tyr Asp Glu
 65                  70                  75                  80
```

-continued

```
ctt cgc gct gcc agc cat cag ccg ccg act ctc atc gat ctt gac ttc      288
Leu Arg Ala Ala Ser His Gln Pro Pro Thr Leu Ile Asp Leu Asp Phe
                 85                  90                  95

aac ggc acg gat gaa aca atg tcc aac gat gct caa atc gaa gcc aac      336
Asn Gly Thr Asp Glu Thr Met Ser Asn Asp Ala Gln Ile Glu Ala Asn
            100                 105                 110

ctc aaa att atg tat agg cag atg gtt tcc aac tcc aag aaa ccg ctg      384
Leu Lys Ile Met Tyr Arg Gln Met Val Ser Asn Ser Lys Lys Pro Leu
        115                 120                 125

ttg ttc ttt ggt tcg ccc tac agg gct ggc act gaa cca gat cca ggg      432
Leu Phe Phe Gly Ser Pro Tyr Arg Ala Gly Thr Glu Pro Asp Pro Gly
    130                 135                 140

ggc ggt tca atc gaa acg acc cca cat ggt ccg gtt cat tta tgg acc      480
Gly Gly Ser Ile Glu Thr Thr Pro His Gly Pro Val His Leu Trp Thr
145                 150                 155                 160

gga gat aac acg caa cct aat ttt gaa gac atg ggg aat ttt tac tcc      528
Gly Asp Asn Thr Gln Pro Asn Phe Glu Asp Met Gly Asn Phe Tyr Ser
                165                 170                 175

gct gga agg gat cca ata ttt ttt tcg cac cat tcg aat ata gat cga      576
Ala Gly Arg Asp Pro Ile Phe Phe Ser His His Ser Asn Ile Asp Arg
            180                 185                 190

atg tgg aat att                                                      588
Met Trp Asn Ile
        195


<210> SEQ ID NO: 28
<211> LENGTH: 196
<212> TYPE: PRT
<213> ORGANISM: APPLE

<400> SEQUENCE: 28

His Cys Ala Tyr Cys Asp Gly Ala Tyr Asp Gln Val Gly Phe Pro Asn
  1               5                  10                  15

Leu Glu Leu Gln Ile His Gln Cys Trp Leu Phe Phe Pro Phe His Arg
             20                  25                  30

Tyr Tyr Leu Tyr Phe His Glu Arg Ile Leu Ala Lys Leu Ile Asp Asp
         35                  40                  45

Pro Thr Phe Ala Leu Pro Phe Trp Asn Trp Asp Ala Pro Ala Gly Met
     50                  55                  60

Gln Leu Pro Ala Leu Phe Ala Asn Pro Asp Ser Pro Leu Tyr Asp Glu
 65                  70                  75                  80

Leu Arg Ala Ala Ser His Gln Pro Pro Thr Leu Ile Asp Leu Asp Phe
                 85                  90                  95

Asn Gly Thr Asp Glu Thr Met Ser Asn Asp Ala Gln Ile Glu Ala Asn
            100                 105                 110

Leu Lys Ile Met Tyr Arg Gln Met Val Ser Asn Ser Lys Lys Pro Leu
        115                 120                 125

Leu Phe Phe Gly Ser Pro Tyr Arg Ala Gly Thr Glu Pro Asp Pro Gly
    130                 135                 140

Gly Gly Ser Ile Glu Thr Thr Pro His Gly Pro Val His Leu Trp Thr
145                 150                 155                 160

Gly Asp Asn Thr Gln Pro Asn Phe Glu Asp Met Gly Asn Phe Tyr Ser
                165                 170                 175

Ala Gly Arg Asp Pro Ile Phe Phe Ser His His Ser Asn Ile Asp Arg
            180                 185                 190

Met Trp Asn Ile
        195
```

```
<210> SEQ ID NO: 29
<211> LENGTH: 671
<212> TYPE: DNA
<213> ORGANISM: LETTUCE
<220> FEATURE:
<221> NAME/KEY: CDS
<222> LOCATION: (1)..(669)

<400> SEQUENCE: 29

ctg cat tgt gcg tat tgc gat ggg gca tac gat caa gtc ggt ttc cct       48
Leu His Cys Ala Tyr Cys Asp Gly Ala Tyr Asp Gln Val Gly Phe Pro
  1               5                  10                  15

gat ctc gag ctt caa gtc cat ggc tca tgg ttg ttc tta cct ttc cac       96
Asp Leu Glu Leu Gln Val His Gly Ser Trp Leu Phe Leu Pro Phe His
             20                  25                  30

cgc tat tac tta tac ttc ttc gac aaa att tgt ggc gga tta atc gat      144
Arg Tyr Tyr Leu Tyr Phe Phe Asp Lys Ile Cys Gly Gly Leu Ile Asp
         35                  40                  45

gat cca aat ttc gca atc cct ttt tgg aac tgg gat gca cct gat ggc      192
Asp Pro Asn Phe Ala Ile Pro Phe Trp Asn Trp Asp Ala Pro Asp Gly
     50                  55                  60

atg aag atc cct gat att tac acg aat aag aaa tct ccg ttg tac gat      240
Met Lys Ile Pro Asp Ile Tyr Thr Asn Lys Lys Ser Pro Leu Tyr Asp
 65                  70                  75                  80

gct ctt cgt gat gcg aag cat caa gca ccg tct ctg att gat ctt gac      288
Ala Leu Arg Asp Ala Lys His Gln Ala Pro Ser Leu Ile Asp Leu Asp
                 85                  90                  95

tac aat ggt gac gat gaa aat ctt agc cga tcg aga caa acc tcc aca      336
Tyr Asn Gly Asp Asp Glu Asn Leu Ser Arg Ser Arg Gln Thr Ser Thr
            100                 105                 110

aat ctc aca att atg tac aga caa atg gtg tct agt tcc aag act gct      384
Asn Leu Thr Ile Met Tyr Arg Gln Met Val Ser Ser Ser Lys Thr Ala
        115                 120                 125

agt ctt ttc atg ggt act cct tat cgt gca ggt gat gag gct agc cct      432
Ser Leu Phe Met Gly Thr Pro Tyr Arg Ala Gly Asp Glu Ala Ser Pro
    130                 135                 140

ggc tct ggc tcg ctc gag agc ata cca cat ggc ccg gtt cat atc tgg      480
Gly Ser Gly Ser Leu Glu Ser Ile Pro His Gly Pro Val His Ile Trp
145                 150                 155                 160

acc gga gat agg aac cag caa aat ggt gca gac atg ggt aac ttt tat      528
Thr Gly Asp Arg Asn Gln Gln Asn Gly Ala Asp Met Gly Asn Phe Tyr
                165                 170                 175

tct gca gcc aga gac cct att ttt tat gca cat cat gcg aat atc gac      576
Ser Ala Ala Arg Asp Pro Ile Phe Tyr Ala His His Ala Asn Ile Asp
            180                 185                 190

aga atg tgg tca gtt tgg aaa act cta gga gga aga agg aat gat ttt      624
Arg Met Trp Ser Val Trp Lys Thr Leu Gly Gly Arg Arg Asn Asp Phe
        195                 200                 205

aca gat aaa gac tgg ctt gat ttt ttg ttc ttg ttc tac gac gag aa       671
Thr Asp Lys Asp Trp Leu Asp Phe Leu Phe Leu Phe Tyr Asp Glu
    210                 215                 220


<210> SEQ ID NO: 30
<211> LENGTH: 223
<212> TYPE: PRT
<213> ORGANISM: LETTUCE

<400> SEQUENCE: 30

Leu His Cys Ala Tyr Cys Asp Gly Ala Tyr Asp Gln Val Gly Phe Pro
  1               5                  10                  15

Asp Leu Glu Leu Gln Val His Gly Ser Trp Leu Phe Leu Pro Phe His
```

-continued

```
            20                  25                  30

Arg Tyr Tyr Leu Tyr Phe Phe Asp Lys Ile Cys Gly Gly Leu Ile Asp
        35                  40                  45

Asp Pro Asn Phe Ala Ile Pro Phe Trp Asn Trp Asp Ala Pro Asp Gly
    50                  55                  60

Met Lys Ile Pro Asp Ile Tyr Thr Asn Lys Lys Ser Pro Leu Tyr Asp
65                  70                  75                  80

Ala Leu Arg Asp Ala Lys His Gln Ala Pro Ser Leu Ile Asp Leu Asp
                85                  90                  95

Tyr Asn Gly Asp Asp Glu Asn Leu Ser Arg Ser Arg Gln Thr Ser Thr
            100                 105                 110

Asn Leu Thr Ile Met Tyr Arg Gln Met Val Ser Ser Ser Lys Thr Ala
        115                 120                 125

Ser Leu Phe Met Gly Thr Pro Tyr Arg Ala Gly Asp Glu Ala Ser Pro
    130                 135                 140

Gly Ser Gly Ser Leu Glu Ser Ile Pro His Gly Pro Val His Ile Trp
145                 150                 155                 160

Thr Gly Asp Arg Asn Gln Gln Asn Gly Ala Asp Met Gly Asn Phe Tyr
                165                 170                 175

Ser Ala Ala Arg Asp Pro Ile Phe Tyr Ala His His Ala Asn Ile Asp
            180                 185                 190

Arg Met Trp Ser Val Trp Lys Thr Leu Gly Gly Arg Arg Asn Asp Phe
        195                 200                 205

Thr Asp Lys Asp Trp Leu Asp Phe Leu Phe Leu Phe Tyr Asp Glu
    210                 215                 220


<210> SEQ ID NO: 31
<211> LENGTH: 668
<212> TYPE: DNA
<213> ORGANISM: FRENCH BEAN
<220> FEATURE:
<221> NAME/KEY: CDS
<222> LOCATION: (1)..(666)

<400> SEQUENCE: 31

cat tgt gcg tac tgt aat gga gcc tat cac ctg tct cat cct ttc caa       48
His Cys Ala Tyr Cys Asn Gly Ala Tyr His Leu Ser His Pro Phe Gln
  1               5                  10                  15

gac aca aaa ctc gac att cac agg tct tgg ttt ttc ttt ccc ttc cac       96
Asp Thr Lys Leu Asp Ile His Arg Ser Trp Phe Phe Phe Pro Phe His
            20                  25                  30

cgt tgg tac att tac ttc ttt gaa cga att ttg ggg aac ttg att ggt      144
Arg Trp Tyr Ile Tyr Phe Phe Glu Arg Ile Leu Gly Asn Leu Ile Gly
        35                  40                  45

gac cct aac ttt gct tta cca ttt tgg agt tgg gat tct ata gag ggc      192
Asp Pro Asn Phe Ala Leu Pro Phe Trp Ser Trp Asp Ser Ile Glu Gly
    50                  55                  60

atg caa atg cca tcg tat ttc gca aac cct aac tcg tca gtt tat cac      240
Met Gln Met Pro Ser Tyr Phe Ala Asn Pro Asn Ser Ser Val Tyr His
65                  70                  75                  80

aaa ctc cga cac cag aaa cac ctg cca ccc cac gtg gtg gac ctg aac      288
Lys Leu Arg His Gln Lys His Leu Pro Pro His Val Val Asp Leu Asn
                85                  90                  95

tat gca agt gaa agt agc tat gtc cct tct cat caa caa gtt tcg tat      336
Tyr Ala Ser Glu Ser Ser Tyr Val Pro Ser His Gln Gln Val Ser Tyr
            100                 105                 110

aat tta gcc acc atg tac aga caa atg gtg cta gca agt acc acg gaa      384
Asn Leu Ala Thr Met Tyr Arg Gln Met Val Leu Ala Ser Thr Thr Glu
```

```
        115                 120                 125

ttg ttc atg gga ggc cct ttt cga cta ggg gat aac cct cgt cct ggt      432
Leu Phe Met Gly Gly Pro Phe Arg Leu Gly Asp Asn Pro Arg Pro Gly
    130                 135                 140

cct ggt tct gtg gag gct gct cca cat aac acc gtt cat aca tgg gtt      480
Pro Gly Ser Val Glu Ala Ala Pro His Asn Thr Val His Thr Trp Val
145                 150                 155                 160

ggt gga gcc gaa act cca aac cat gag gac atg gga acg ttt tac aca      528
Gly Gly Ala Glu Thr Pro Asn His Glu Asp Met Gly Thr Phe Tyr Thr
                165                 170                 175

gct gct aga gac ccc att ttc tat ggt cat cac tcg aac ttg gat cga      576
Ala Ala Arg Asp Pro Ile Phe Tyr Gly His His Ser Asn Leu Asp Arg
            180                 185                 190

atg tgg gcg ata tgg aaa aca ctg gga gaa gga aga aag gac tat agt      624
Met Trp Ala Ile Trp Lys Thr Leu Gly Glu Gly Arg Lys Asp Tyr Ser
        195                 200                 205

gat gaa gat tgg tta gat tct gag ttt ttc ttc tat gac gaa aa           668
Asp Glu Asp Trp Leu Asp Ser Glu Phe Phe Phe Tyr Asp Glu
    210                 215                 220


<210> SEQ ID NO: 32
<211> LENGTH: 222
<212> TYPE: PRT
<213> ORGANISM: FRENCH BEAN

<400> SEQUENCE: 32

His Cys Ala Tyr Cys Asn Gly Ala Tyr His Leu Ser His Pro Phe Gln
  1               5                  10                  15

Asp Thr Lys Leu Asp Ile His Arg Ser Trp Phe Phe Phe Pro Phe His
             20                  25                  30

Arg Trp Tyr Ile Tyr Phe Phe Glu Arg Ile Leu Gly Asn Leu Ile Gly
        35                  40                  45

Asp Pro Asn Phe Ala Leu Pro Phe Trp Ser Trp Asp Ser Ile Glu Gly
     50                  55                  60

Met Gln Met Pro Ser Tyr Phe Ala Asn Pro Asn Ser Ser Val Tyr His
 65                  70                  75                  80

Lys Leu Arg His Gln Lys His Leu Pro Pro His Val Val Asp Leu Asn
                 85                  90                  95

Tyr Ala Ser Glu Ser Ser Tyr Val Pro Ser His Gln Gln Val Ser Tyr
            100                 105                 110

Asn Leu Ala Thr Met Tyr Arg Gln Met Val Leu Ala Ser Thr Thr Glu
        115                 120                 125

Leu Phe Met Gly Gly Pro Phe Arg Leu Gly Asp Asn Pro Arg Pro Gly
    130                 135                 140

Pro Gly Ser Val Glu Ala Ala Pro His Asn Thr Val His Thr Trp Val
145                 150                 155                 160

Gly Gly Ala Glu Thr Pro Asn His Glu Asp Met Gly Thr Phe Tyr Thr
                165                 170                 175

Ala Ala Arg Asp Pro Ile Phe Tyr Gly His His Ser Asn Leu Asp Arg
            180                 185                 190

Met Trp Ala Ile Trp Lys Thr Leu Gly Glu Gly Arg Lys Asp Tyr Ser
        195                 200                 205

Asp Glu Asp Trp Leu Asp Ser Glu Phe Phe Phe Tyr Asp Glu
    210                 215                 220


<210> SEQ ID NO: 33
<211> LENGTH: 689
```

```
<212> TYPE: DNA
<213> ORGANISM: FRENCH BEAN
<220> FEATURE:
<221> NAME/KEY: CDS
<222> LOCATION: (1)..(687)

<400> SEQUENCE: 33

cac tgc gcg tat tgc aat ggt gcc tat cac caa gtt ggg ttt cct gac       48
His Cys Ala Tyr Cys Asn Gly Ala Tyr His Gln Val Gly Phe Pro Asp
  1               5                  10                  15

ctt gac tta caa gtc cac aac tcc tgg cta ttc ttc cct tac cat cgt       96
Leu Asp Leu Gln Val His Asn Ser Trp Leu Phe Phe Pro Tyr His Arg
             20                  25                  30

ttt tac ctt tat ttc tat gag aga ata ttg gga agc ttg att ggt gac      144
Phe Tyr Leu Tyr Phe Tyr Glu Arg Ile Leu Gly Ser Leu Ile Gly Asp
         35                  40                  45

cca act ttt gct att cca ttt tgg aac tgg gac cac cct aaa ggt ggc      192
Pro Thr Phe Ala Ile Pro Phe Trp Asn Trp Asp His Pro Lys Gly Gly
     50                  55                  60

atg acg atg cct tcc ctt ttc aca gat aaa aac tcc cct tta tat gac      240
Met Thr Met Pro Ser Leu Phe Thr Asp Lys Asn Ser Pro Leu Tyr Asp
 65                  70                  75                  80

cct cgc agg aat ctt tct cat caa cca cca act ctt ata gac cta gat      288
Pro Arg Arg Asn Leu Ser His Gln Pro Pro Thr Leu Ile Asp Leu Asp
                 85                  90                  95

tat aac aga aag gac gat aac aat ccc aac cag agt gaa agt gtt gct      336
Tyr Asn Arg Lys Asp Asp Asn Asn Pro Asn Gln Ser Glu Ser Val Ala
            100                 105                 110

gac caa atc tct agt aac ctt act ata atg tat agg aac gtt gtc tcg      384
Asp Gln Ile Ser Ser Asn Leu Thr Ile Met Tyr Arg Asn Val Val Ser
        115                 120                 125

ggt ggg aaa ctc ccg aag ctc ttc ctt gga agc cct tat cgt gct ggt      432
Gly Gly Lys Leu Pro Lys Leu Phe Leu Gly Ser Pro Tyr Arg Ala Gly
    130                 135                 140

tca gat cct gac cct ggt gct ggg agc cta gag cat gtt cct cat att      480
Ser Asp Pro Asp Pro Gly Ala Gly Ser Leu Glu His Val Pro His Ile
145                 150                 155                 160

cca gtt cac tct tgg tgt ggt gat ccc cga gag cct aac cgt gag gac      528
Pro Val His Ser Trp Cys Gly Asp Pro Arg Glu Pro Asn Arg Glu Asp
                165                 170                 175

atg gga gtc ttc tat tca gct ggc aaa gac cct att ttt tat gct cac      576
Met Gly Val Phe Tyr Ser Ala Gly Lys Asp Pro Ile Phe Tyr Ala His
            180                 185                 190

cat gcc aac gtg gat aga gtg tgg agc ata tgg aaa aca ata cca ggt      624
His Ala Asn Val Asp Arg Val Trp Ser Ile Trp Lys Thr Ile Pro Gly
        195                 200                 205

ggg aaa aga agg gat ttc act gat cct gat tgg cta gaa tct agc ttt      672
Gly Lys Arg Arg Asp Phe Thr Asp Pro Asp Trp Leu Glu Ser Ser Phe
    210                 215                 220

ttg ttc tac gat gaa aa                                               689
Leu Phe Tyr Asp Glu
225


<210> SEQ ID NO: 34
<211> LENGTH: 229
<212> TYPE: PRT
<213> ORGANISM: FRENCH BEAN

<400> SEQUENCE: 34

His Cys Ala Tyr Cys Asn Gly Ala Tyr His Gln Val Gly Phe Pro Asp
  1               5                  10                  15
```

-continued

```
Leu Asp Leu Gln Val His Asn Ser Trp Leu Phe Phe Pro Tyr His Arg
            20                  25                  30

Phe Tyr Leu Tyr Phe Tyr Glu Arg Ile Leu Gly Ser Leu Ile Gly Asp
        35                  40                  45

Pro Thr Phe Ala Ile Pro Phe Trp Asn Trp Asp His Pro Lys Gly Gly
    50                  55                  60

Met Thr Met Pro Ser Leu Phe Thr Asp Lys Asn Ser Pro Leu Tyr Asp
65                  70                  75                  80

Pro Arg Arg Asn Leu Ser His Gln Pro Pro Thr Leu Ile Asp Leu Asp
                85                  90                  95

Tyr Asn Arg Lys Asp Asp Asn Asn Pro Asn Gln Ser Glu Ser Val Ala
            100                 105                 110

Asp Gln Ile Ser Ser Asn Leu Thr Ile Met Tyr Arg Asn Val Val Ser
        115                 120                 125

Gly Gly Lys Leu Pro Lys Leu Phe Leu Gly Ser Pro Tyr Arg Ala Gly
    130                 135                 140

Ser Asp Pro Asp Pro Gly Ala Gly Ser Leu Glu His Val Pro His Ile
145                 150                 155                 160

Pro Val His Ser Trp Cys Gly Asp Pro Arg Glu Pro Asn Arg Glu Asp
                165                 170                 175

Met Gly Val Phe Tyr Ser Ala Gly Lys Asp Pro Ile Phe Tyr Ala His
            180                 185                 190

His Ala Asn Val Asp Arg Val Trp Ser Ile Trp Lys Thr Ile Pro Gly
        195                 200                 205

Gly Lys Arg Arg Asp Phe Thr Asp Pro Asp Trp Leu Glu Ser Ser Phe
    210                 215                 220

Leu Phe Tyr Asp Glu
225


<210> SEQ ID NO: 35
<211> LENGTH: 662
<212> TYPE: DNA
<213> ORGANISM: FRENCH BEAN
<220> FEATURE:
<221> NAME/KEY: CDS
<222> LOCATION: (1)..(660)

<400> SEQUENCE: 35

cat tgt gcg tat tgt gac ggt gca tat cac caa gtt ggg ttc cct gac       48
His Cys Ala Tyr Cys Asp Gly Ala Tyr His Gln Val Gly Phe Pro Asp
  1               5                  10                  15

ctt gat ctc caa gtc cac aac tct tgg ctc ttc ttt ccc ttc cat cga       96
Leu Asp Leu Gln Val His Asn Ser Trp Leu Phe Phe Pro Phe His Arg
            20                  25                  30

tgg tat ctc tat ttc tac gaa aga atc ttg ggg agc ttg atc aac gac      144
Trp Tyr Leu Tyr Phe Tyr Glu Arg Ile Leu Gly Ser Leu Ile Asn Asp
        35                  40                  45

cca acc ttc gcc ctc ccg ttt tgg aac tgg gat gct ccc aag ggc atg      192
Pro Thr Phe Ala Leu Pro Phe Trp Asn Trp Asp Ala Pro Lys Gly Met
    50                  55                  60

caa ctt cct tcc att tat gca gac cct aaa tca cct ctc tat gat cct      240
Gln Leu Pro Ser Ile Tyr Ala Asp Pro Lys Ser Pro Leu Tyr Asp Pro
 65                  70                  75                  80

ctt cgc aat tct aat cat caa cct cca aca ctc gtt gac ctt gac ttc      288
Leu Arg Asn Ser Asn His Gln Pro Pro Thr Leu Val Asp Leu Asp Phe
                85                  90                  95

gac att gag gat cct gat gcc gat gga aaa atc tcc tcc aac ctt acc      336
Asp Ile Glu Asp Pro Asp Ala Asp Gly Lys Ile Ser Ser Asn Leu Thr
```

-continued

```
            100                 105                 110

ata atg tat agg caa gtt gtg tct aat ggg aaa act cct aga ctg ttc      384
Ile Met Tyr Arg Gln Val Val Ser Asn Gly Lys Thr Pro Arg Leu Phe
        115                 120                 125

ctt gga aat gct tac cgt gct gga gat gaa ccc gac ccg ggt ggt gga      432
Leu Gly Asn Ala Tyr Arg Ala Gly Asp Glu Pro Asp Pro Gly Gly Gly
    130                 135                 140

tcc gta gag aac gtt cca cat gga cct gtt cat gta tgg acc ggt gat      480
Ser Val Glu Asn Val Pro His Gly Pro Val His Val Trp Thr Gly Asp
145                 150                 155                 160

atc gac cag ccc aac att gag aac atg gga act ttc tat tcg gct gca      528
Ile Asp Gln Pro Asn Ile Glu Asn Met Gly Thr Phe Tyr Ser Ala Ala
                165                 170                 175

aga gac ccc att ttc ttc tct cat cat tcc aat ata gat agg atg tgg      576
Arg Asp Pro Ile Phe Phe Ser His His Ser Asn Ile Asp Arg Met Trp
            180                 185                 190

tcc ata tgg aaa aca ctt ggt ggg aaa aga agg gat ttc agt gac tcg      624
Ser Ile Trp Lys Thr Leu Gly Gly Lys Arg Arg Asp Phe Ser Asp Ser
        195                 200                 205

gat tgg tta gaa tct ggg ctt ctc ttt tac gac gag aa                   662
Asp Trp Leu Glu Ser Gly Leu Leu Phe Tyr Asp Glu
    210                 215                 220


<210> SEQ ID NO: 36
<211> LENGTH: 220
<212> TYPE: PRT
<213> ORGANISM: FRENCH BEAN

<400> SEQUENCE: 36

His Cys Ala Tyr Cys Asp Gly Ala Tyr His Gln Val Gly Phe Pro Asp
  1               5                  10                  15

Leu Asp Leu Gln Val His Asn Ser Trp Leu Phe Phe Pro Phe His Arg
             20                  25                  30

Trp Tyr Leu Tyr Phe Tyr Glu Arg Ile Leu Gly Ser Leu Ile Asn Asp
         35                  40                  45

Pro Thr Phe Ala Leu Pro Phe Trp Asn Trp Asp Ala Pro Lys Gly Met
     50                  55                  60

Gln Leu Pro Ser Ile Tyr Ala Asp Pro Lys Ser Pro Leu Tyr Asp Pro
 65                  70                  75                  80

Leu Arg Asn Ser Asn His Gln Pro Pro Thr Leu Val Asp Leu Asp Phe
                 85                  90                  95

Asp Ile Glu Asp Pro Asp Ala Asp Gly Lys Ile Ser Ser Asn Leu Thr
            100                 105                 110

Ile Met Tyr Arg Gln Val Val Ser Asn Gly Lys Thr Pro Arg Leu Phe
        115                 120                 125

Leu Gly Asn Ala Tyr Arg Ala Gly Asp Glu Pro Asp Pro Gly Gly Gly
    130                 135                 140

Ser Val Glu Asn Val Pro His Gly Pro Val His Val Trp Thr Gly Asp
145                 150                 155                 160

Ile Asp Gln Pro Asn Ile Glu Asn Met Gly Thr Phe Tyr Ser Ala Ala
                165                 170                 175

Arg Asp Pro Ile Phe Phe Ser His His Ser Asn Ile Asp Arg Met Trp
            180                 185                 190

Ser Ile Trp Lys Thr Leu Gly Gly Lys Arg Arg Asp Phe Ser Asp Ser
        195                 200                 205

Asp Trp Leu Glu Ser Gly Leu Leu Phe Tyr Asp Glu
    210                 215                 220
```

```
<210> SEQ ID NO: 37
<211> LENGTH: 426
<212> TYPE: DNA
<213> ORGANISM: BANANA
<220> FEATURE:
<221> NAME/KEY: CDS
<222> LOCATION: (1)..(426)

<400> SEQUENCE: 37

ttg ccg ttt tgg aac tgg gac acc aag gac ggc atg acg ttc ccc gcc       48
Leu Pro Phe Trp Asn Trp Asp Thr Lys Asp Gly Met Thr Phe Pro Ala
  1               5                  10                  15

atc ttc cag gat gcg gca tcc ccg ctg tac gac ccg aga cgc gac caa       96
Ile Phe Gln Asp Ala Ala Ser Pro Leu Tyr Asp Pro Arg Arg Asp Gln
             20                  25                  30

cgc cac gtc aag gac ggc aag atc ctc gac ctc aag tac gcc tac acc      144
Arg His Val Lys Asp Gly Lys Ile Leu Asp Leu Lys Tyr Ala Tyr Thr
         35                  40                  45

gaa aac act gca tcc gac agc gag atc ata cgg gag aac ctc tgc ttc      192
Glu Asn Thr Ala Ser Asp Ser Glu Ile Ile Arg Glu Asn Leu Cys Phe
     50                  55                  60

ata cag aag acg ttc aag cac agc ctg tcg ctg gcg gaa ctg ttc atg      240
Ile Gln Lys Thr Phe Lys His Ser Leu Ser Leu Ala Glu Leu Phe Met
 65                  70                  75                  80

ggg gat ccc gtg cgc gcg ggg gag aag gag atc cag gag gct aat ggg      288
Gly Asp Pro Val Arg Ala Gly Glu Lys Glu Ile Gln Glu Ala Asn Gly
                 85                  90                  95

cag atg gaa gtc atc cac aat gcg gcg cac atg tgg gtc gga gag ccg      336
Gln Met Glu Val Ile His Asn Ala Ala His Met Trp Val Gly Glu Pro
            100                 105                 110

gac gga tac aag gaa aac atg ggg gac ttc tcc acc gcc gcc cgc gat      384
Asp Gly Tyr Lys Glu Asn Met Gly Asp Phe Ser Thr Ala Ala Arg Asp
        115                 120                 125

tct gtt ttc ttc tgc cac cat tgc aat gtc gac agc atg tgg              426
Ser Val Phe Phe Cys His His Cys Asn Val Asp Ser Met Trp
    130                 135                 140


<210> SEQ ID NO: 38
<211> LENGTH: 142
<212> TYPE: PRT
<213> ORGANISM: BANANA

<400> SEQUENCE: 38

Leu Pro Phe Trp Asn Trp Asp Thr Lys Asp Gly Met Thr Phe Pro Ala
  1               5                  10                  15

Ile Phe Gln Asp Ala Ala Ser Pro Leu Tyr Asp Pro Arg Arg Asp Gln
             20                  25                  30

Arg His Val Lys Asp Gly Lys Ile Leu Asp Leu Lys Tyr Ala Tyr Thr
         35                  40                  45

Glu Asn Thr Ala Ser Asp Ser Glu Ile Ile Arg Glu Asn Leu Cys Phe
     50                  55                  60

Ile Gln Lys Thr Phe Lys His Ser Leu Ser Leu Ala Glu Leu Phe Met
 65                  70                  75                  80

Gly Asp Pro Val Arg Ala Gly Glu Lys Glu Ile Gln Glu Ala Asn Gly
                 85                  90                  95

Gln Met Glu Val Ile His Asn Ala Ala His Met Trp Val Gly Glu Pro
            100                 105                 110

Asp Gly Tyr Lys Glu Asn Met Gly Asp Phe Ser Thr Ala Ala Arg Asp
        115                 120                 125
```

```
Ser Val Phe Phe Cys His His Cys Asn Val Asp Ser Met Trp
    130                 135                 140


<210> SEQ ID NO: 39
<211> LENGTH: 512
<212> TYPE: DNA
<213> ORGANISM: BANANA
<220> FEATURE:
<221> NAME/KEY: CDS
<222> LOCATION: (1)..(510)

<400> SEQUENCE: 39

ttg ccg ttt tgg aac tgg gac gca ccc ggc gga atg atg ctg ccg tcg       48
Leu Pro Phe Trp Asn Trp Asp Ala Pro Gly Gly Met Met Leu Pro Ser
  1               5                  10                  15

atc tac gcc gac cct tcg tcg ccc ctc tac gac aaa ctt cgc gac gcc       96
Ile Tyr Ala Asp Pro Ser Ser Pro Leu Tyr Asp Lys Leu Arg Asp Ala
             20                  25                  30

aag cac caa cca cct gtc ctt gtc gac ctc gac tac aat gga acc gac      144
Lys His Gln Pro Pro Val Leu Val Asp Leu Asp Tyr Asn Gly Thr Asp
         35                  40                  45

cca acc ttc ccc gac gac cag caa atc gat cac aac ctc aag atc atg      192
Pro Thr Phe Pro Asp Asp Gln Gln Ile Asp His Asn Leu Lys Ile Met
     50                  55                  60

tac cgc caa gtc ttc tcc aac ggc aag acg ccg ttg ctg ttc tta ggc      240
Tyr Arg Gln Val Phe Ser Asn Gly Lys Thr Pro Leu Leu Phe Leu Gly
 65                  70                  75                  80

tca gct tac cgt gcc ggt gac cag cct aac ccc ggc gcg gga tcc atc      288
Ser Ala Tyr Arg Ala Gly Asp Gln Pro Asn Pro Gly Ala Gly Ser Ile
                 85                  90                  95

gag aac atg ccg cac aac aac atg cac ttg tgg acc ggc gac cgc acc      336
Glu Asn Met Pro His Asn Asn Met His Leu Trp Thr Gly Asp Arg Thr
            100                 105                 110

cag ccc aac ttc gag aac atg ggc acc ttc tac gcg gcg gcg cgc gac      384
Gln Pro Asn Phe Glu Asn Met Gly Thr Phe Tyr Ala Ala Ala Arg Asp
        115                 120                 125

ccc atc ttc ttc gcc cac cac gcc aac atc gac cga atg tgg tac ctg      432
Pro Ile Phe Phe Ala His His Ala Asn Ile Asp Arg Met Trp Tyr Leu
    130                 135                 140

tgg aag aag ctc agc agg aag cac cag gac ttc aat gac tcg gac tgg      480
Trp Lys Lys Leu Ser Arg Lys His Gln Asp Phe Asn Asp Ser Asp Trp
145                 150                 155                 160

ctc aaa gct tcc ttc ctc ttc tat gac gaa aa                           512
Leu Lys Ala Ser Phe Leu Phe Tyr Asp Glu
                165                 170


<210> SEQ ID NO: 40
<211> LENGTH: 170
<212> TYPE: PRT
<213> ORGANISM: BANANA

<400> SEQUENCE: 40

Leu Pro Phe Trp Asn Trp Asp Ala Pro Gly Gly Met Met Leu Pro Ser
  1               5                  10                  15

Ile Tyr Ala Asp Pro Ser Ser Pro Leu Tyr Asp Lys Leu Arg Asp Ala
             20                  25                  30

Lys His Gln Pro Pro Val Leu Val Asp Leu Asp Tyr Asn Gly Thr Asp
         35                  40                  45

Pro Thr Phe Pro Asp Asp Gln Gln Ile Asp His Asn Leu Lys Ile Met
     50                  55                  60
```

-continued

```
Tyr Arg Gln Val Phe Ser Asn Gly Lys Thr Pro Leu Leu Phe Leu Gly
 65                  70                  75                  80

Ser Ala Tyr Arg Ala Gly Asp Gln Pro Asn Pro Gly Ala Gly Ser Ile
                85                  90                  95

Glu Asn Met Pro His Asn Asn Met His Leu Trp Thr Gly Asp Arg Thr
            100                 105                 110

Gln Pro Asn Phe Glu Asn Met Gly Thr Phe Tyr Ala Ala Ala Arg Asp
        115                 120                 125

Pro Ile Phe Phe Ala His His Ala Asn Ile Asp Arg Met Trp Tyr Leu
    130                 135                 140

Trp Lys Lys Leu Ser Arg Lys His Gln Asp Phe Asn Asp Ser Asp Trp
145                 150                 155                 160

Leu Lys Ala Ser Phe Leu Phe Tyr Asp Glu
                165                 170


<210> SEQ ID NO: 41
<211> LENGTH: 662
<212> TYPE: DNA
<213> ORGANISM: RICE
<220> FEATURE:
<221> NAME/KEY: CDS
<222> LOCATION: (1)..(660)

<400> SEQUENCE: 41

ttg ccg tat tgg aat tgg gac gcg ccg gcc ggc atg tcg ttc ccg gcg       48
Leu Pro Tyr Trp Asn Trp Asp Ala Pro Ala Gly Met Ser Phe Pro Ala
  1               5                  10                  15

atc tac gcc aac tgc agg ctg tcg tcg ctg tac gac cca agg cga aat       96
Ile Tyr Ala Asn Cys Arg Leu Ser Ser Leu Tyr Asp Pro Arg Arg Asn
            20                  25                  30

cag gcg cac cag cca ccg ttc ccg ctc gac ctc aac tac agc gga acc      144
Gln Ala His Gln Pro Pro Phe Pro Leu Asp Leu Asn Tyr Ser Gly Thr
        35                  40                  45

gac cca acc atc ccg gaa gat cag ctg atc gat cag aac ctc aag atc      192
Asp Pro Thr Ile Pro Glu Asp Gln Leu Ile Asp Gln Asn Leu Lys Ile
     50                  55                  60

atg tac cgc cag gcc agt aat cac ata cac agt ttg aca caa act agg      240
Met Tyr Arg Gln Ala Ser Asn His Ile His Ser Leu Thr Gln Thr Arg
 65                  70                  75                  80

aat taa ttg aag tag cta ctg aaa acc gta gat agc aaa ctc caa att      288
Asn     Leu Lys     Leu Leu Lys Thr Val Asp Ser Lys Leu Gln Ile
                85                  90                  95

aat tag tcg act tta aat tgg atc gcg tgt cta ata tga aca gta taa      336
Asn     Ser Thr Leu Asn Trp Ile Ala Cys Leu Ile     Thr Val
            100                 105                 110

ttt atg atg tat cag atg att tcg ggg gct agg aag aaa gag ctg ttc      384
Phe Met Met Tyr Gln Met Ile Ser Gly Ala Arg Lys Lys Glu Leu Phe
        115                 120                 125

atg gga cat ccg tac agc gcc ggc gac cag ccg aaa ccg ggg gcg ggc      432
Met Gly His Pro Tyr Ser Ala Gly Asp Gln Pro Lys Pro Gly Ala Gly
    130                 135                 140

acc gtc gag ttc gtg ccg cac aac acc gtc cac aac tgg acc ggc gac      480
Thr Val Glu Phe Val Pro His Asn Thr Val His Asn Trp Thr Gly Asp
145                 150                 155                 160

ccg agg cag ccg aac ggc gag gac atg ggc atg ttc tac tcg gcg gcg      528
Pro Arg Gln Pro Asn Gly Glu Asp Met Gly Met Phe Tyr Ser Ala Ala
                165                 170                 175

cgc gac ccg gtg ttc ttc gcg cac cac ggc aac gtc gac cgc atg tgg      576
Arg Asp Pro Val Phe Phe Ala His His Gly Asn Val Asp Arg Met Trp
            180                 185                 190
```

-continued

```
tac att cgc cac ggc ctc ttc ccc cgc gac acc gac ttc gcc gac ccc      624
Tyr Ile Arg His Gly Leu Phe Pro Arg Asp Thr Asp Phe Ala Asp Pro
        195                 200                 205

gac tgg ctc gac gcg acc ttc ctg ttg tac gac gaa aa                   662
Asp Trp Leu Asp Ala Thr Phe Leu Leu Tyr Asp Glu
    210                 215                 220


<210> SEQ ID NO: 42
<211> LENGTH: 81
<212> TYPE: PRT
<213> ORGANISM: RICE

<400> SEQUENCE: 42

Leu Pro Tyr Trp Asn Trp Asp Ala Pro Ala Gly Met Ser Phe Pro Ala
  1               5                  10                  15

Ile Tyr Ala Asn Cys Arg Leu Ser Ser Leu Tyr Asp Pro Arg Arg Asn
             20                  25                  30

Gln Ala His Gln Pro Pro Phe Pro Leu Asp Leu Asn Tyr Ser Gly Thr
         35                  40                  45

Asp Pro Thr Ile Pro Glu Asp Gln Leu Ile Asp Gln Asn Leu Lys Ile
     50                  55                  60

Met Tyr Arg Gln Ala Ser Asn His Ile His Ser Leu Thr Gln Thr Arg
 65                  70                  75                  80

Asn


<210> SEQ ID NO: 43
<211> LENGTH: 12
<212> TYPE: PRT
<213> ORGANISM: RICE

<400> SEQUENCE: 43

Leu Leu Lys Thr Val Asp Ser Lys Leu Gln Ile Asn
  1               5                  10


<210> SEQ ID NO: 44
<211> LENGTH: 10
<212> TYPE: PRT
<213> ORGANISM: RICE

<400> SEQUENCE: 44

Ser Thr Leu Asn Trp Ile Ala Cys Leu Ile
  1               5                  10


<210> SEQ ID NO: 45
<211> LENGTH: 108
<212> TYPE: PRT
<213> ORGANISM: RICE

<400> SEQUENCE: 45

Phe Met Met Tyr Gln Met Ile Ser Gly Ala Arg Lys Lys Glu Leu Phe
  1               5                  10                  15

Met Gly His Pro Tyr Ser Ala Gly Asp Gln Pro Lys Pro Gly Ala Gly
             20                  25                  30

Thr Val Glu Phe Val Pro His Asn Thr Val His Asn Trp Thr Gly Asp
         35                  40                  45

Pro Arg Gln Pro Asn Gly Glu Asp Met Gly Met Phe Tyr Ser Ala Ala
     50                  55                  60

Arg Asp Pro Val Phe Phe Ala His His Gly Asn Val Asp Arg Met Trp
 65                  70                  75                  80
```

-continued

```
Tyr Ile Arg His Gly Leu Phe Pro Arg Asp Thr Asp Phe Ala Asp Pro
                 85                  90                  95

Asp Trp Leu Asp Ala Thr Phe Leu Leu Tyr Asp Glu
            100                 105


<210> SEQ ID NO: 46
<211> LENGTH: 622
<212> TYPE: DNA
<213> ORGANISM: RICE
<220> FEATURE:
<221> NAME/KEY: CDS
<222> LOCATION: (1)..(300)
<220> FEATURE:
<221> NAME/KEY: CDS
<222> LOCATION: (303)..(620)

<400> SEQUENCE: 46

ttg ccg ttt tgg aac tgg gat gca ccg gac gcg atg agc atg ccg gcg       48
Leu Pro Phe Trp Asn Trp Asp Ala Pro Asp Ala Met Ser Met Pro Ala
  1               5                  10                  15

atg tac acc gac cag tcc tcg ccg ttg ttc gat ccc cgg cgg aac ggg       96
Met Tyr Thr Asp Gln Ser Ser Pro Leu Phe Asp Pro Arg Arg Asn Gly
             20                  25                  30

cgg cac gtg ccg ccg aag ctg atc gat ctg gac tac aat ggg agg gag      144
Arg His Val Pro Pro Lys Leu Ile Asp Leu Asp Tyr Asn Gly Arg Glu
         35                  40                  45

cca cgg ttc acc gac aac caa cag gtt gat caa aac cta cgt gtc atg      192
Pro Arg Phe Thr Asp Asn Gln Gln Val Asp Gln Asn Leu Arg Val Met
     50                  55                  60

tac cgt cag gta tat gtg caa tgc gtg cat cga tgc agc gcg ttc gtc      240
Tyr Arg Gln Val Tyr Val Gln Cys Val His Arg Cys Ser Ala Phe Val
 65                  70                  75                  80

tct acg aaa ttt acc cac gta cgt gac cag aaa atg tac tga aac gtg      288
Ser Thr Lys Phe Thr His Val Arg Asp Gln Lys Met Tyr     Asn Val
                 85                  90                  95

cat gtc aaa ttg gt ttt cag atg atc tcg ctg agt ccg acg ccg tcg       335
His Val Lys Leu    Phe Gln Met Ile Ser Leu Ser Pro Thr Pro Ser
            100                 105                 110

ctc ttc ttc ggc agc ccg tac cgc gcc ggc gac gac ccg aac cag ggg      383
Leu Phe Phe Gly Ser Pro Tyr Arg Ala Gly Asp Asp Pro Asn Gln Gly
            115                 120                 125

cca ggt ccc gtt gag aac atc ccg cac ggg ccg gtg cac atc tgg tgc      431
Pro Gly Pro Val Glu Asn Ile Pro His Gly Pro Val His Ile Trp Cys
        130                 135                 140

ggc gac ccg gag cag ccg gcc ggc gag gac atg ggc aac ttc tac tcg      479
Gly Asp Pro Glu Gln Pro Ala Gly Glu Asp Met Gly Asn Phe Tyr Ser
    145                 150                 155

gcc ggc cgc gac cct ctc ttt tac gcg cac cac gcc aac atc gac cgc      527
Ala Gly Arg Asp Pro Leu Phe Tyr Ala His His Ala Asn Ile Asp Arg
160                 165                 170                 175

atg tgg gcc gtc tgg aag gga ctc gac ccg cgt cgc cac acc gac ctc      575
Met Trp Ala Val Trp Lys Gly Leu Asp Pro Arg Arg His Thr Asp Leu
                180                 185                 190

acc gac cca gac tgg ctc gac gcc tcc ttc ctc ttc tat gac gaa aa       622
Thr Asp Pro Asp Trp Leu Asp Ala Ser Phe Leu Phe Tyr Asp Glu
            195                 200                 205


<210> SEQ ID NO: 47
<211> LENGTH: 93
<212> TYPE: PRT
<213> ORGANISM: RICE

<400> SEQUENCE: 47
```

-continued

```
Leu Pro Phe Trp Asn Trp Asp Ala Pro Asp Ala Met Ser Met Pro Ala
  1               5                  10                  15

Met Tyr Thr Asp Gln Ser Ser Pro Leu Phe Asp Pro Arg Arg Asn Gly
             20                  25                  30

Arg His Val Pro Pro Lys Leu Ile Asp Leu Asp Tyr Asn Gly Arg Glu
         35                  40                  45

Pro Arg Phe Thr Asp Asn Gln Gln Val Asp Gln Asn Leu Arg Val Met
     50                  55                  60

Tyr Arg Gln Val Tyr Val Gln Cys Val His Arg Cys Ser Ala Phe Val
 65                  70                  75                  80

Ser Thr Lys Phe Thr His Val Arg Asp Gln Lys Met Tyr
                 85                  90


<210> SEQ ID NO: 48
<211> LENGTH: 112
<212> TYPE: PRT
<213> ORGANISM: RICE

<400> SEQUENCE: 48

Asn Val His Val Lys Leu Phe Gln Met Ile Ser Leu Ser Pro Thr Pro
  1               5                  10                  15

Ser Leu Phe Phe Gly Ser Pro Tyr Arg Ala Gly Asp Asp Pro Asn Gln
             20                  25                  30

Gly Pro Gly Pro Val Glu Asn Ile Pro His Gly Pro Val His Ile Trp
         35                  40                  45

Cys Gly Asp Pro Glu Gln Pro Ala Gly Glu Asp Met Gly Asn Phe Tyr
     50                  55                  60

Ser Ala Gly Arg Asp Pro Leu Phe Tyr Ala His His Ala Asn Ile Asp
 65                  70                  75                  80

Arg Met Trp Ala Val Trp Lys Gly Leu Asp Pro Arg Arg His Thr Asp
                 85                  90                  95

Leu Thr Asp Pro Asp Trp Leu Asp Ala Ser Phe Leu Phe Tyr Asp Glu
            100                 105                 110


<210> SEQ ID NO: 49
<211> LENGTH: 551
<212> TYPE: DNA
<213> ORGANISM: POTATO
<220> FEATURE:
<221> NAME/KEY: CDS
<222> LOCATION: (1)..(549)

<400> SEQUENCE: 49

gat ccg acg ttc gct ttg cca tat tgg aat tgg gac cat cca aag ggt       48
Asp Pro Thr Phe Ala Leu Pro Tyr Trp Asn Trp Asp His Pro Lys Gly
  1               5                  10                  15

atg cgt tta cct ccc atg ttc gat cgt gaa att act ccc ctt tat gat       96
Met Arg Leu Pro Pro Met Phe Asp Arg Glu Ile Thr Pro Leu Tyr Asp
             20                  25                  30

gaa aga cgt aat cca cac gtc cgt aat gga acc ata atc gat ttt agt      144
Glu Arg Arg Asn Pro His Val Arg Asn Gly Thr Ile Ile Asp Phe Ser
         35                  40                  45

tct tct aaa gac gaa gtt cct act gat gtt aaa cag acg gtg act aac      192
Ser Ser Lys Asp Glu Val Pro Thr Asp Val Lys Gln Thr Val Thr Asn
     50                  55                  60

aac tta act gta atg tac cgt caa atg ata act aat gct gca tgc cct      240
Asn Leu Thr Val Met Tyr Arg Gln Met Ile Thr Asn Ala Ala Cys Pro
 65                  70                  75                  80
```

-continued

```
ttg cag ttc ttc ggt gct cgt tac gtt ctt ggg aat aat aat atg aat      288
Leu Gln Phe Phe Gly Ala Arg Tyr Val Leu Gly Asn Asn Asn Met Asn
                85                  90                  95

gat cgg gga act att gaa aac agc cct cat act ccg gtc cac att tgg      336
Asp Arg Gly Thr Ile Glu Asn Ser Pro His Thr Pro Val His Ile Trp
            100                 105                 110

gct ggt aca gaa caa ggt tca act ttt cct aat ggt gat acg tca tac      384
Ala Gly Thr Glu Gln Gly Ser Thr Phe Pro Asn Gly Asp Thr Ser Tyr
        115                 120                 125

ggt gag gat atg ggc aat ttc tac tca gcc gct tta gac ccg gtt ttc      432
Gly Glu Asp Met Gly Asn Phe Tyr Ser Ala Ala Leu Asp Pro Val Phe
    130                 135                 140

tat agc cac cac gcc aat gta gac cgt atg tgg aat ata tgg aaa gga      480
Tyr Ser His His Ala Asn Val Asp Arg Met Trp Asn Ile Trp Lys Gly
145                 150                 155                 160

tta ggc ggg aaa aaa aag gat atc aca gac aca gat tgg ttg aac tcc      528
Leu Gly Gly Lys Lys Lys Asp Ile Thr Asp Thr Asp Trp Leu Asn Ser
                165                 170                 175

gaa ttc ttt ttc tac gac gaa aa                                       551
Glu Phe Phe Phe Tyr Asp Glu
            180


<210> SEQ ID NO: 50
<211> LENGTH: 183
<212> TYPE: PRT
<213> ORGANISM: POTATO

<400> SEQUENCE: 50

Asp Pro Thr Phe Ala Leu Pro Tyr Trp Asn Trp Asp His Pro Lys Gly
  1               5                  10                  15

Met Arg Leu Pro Pro Met Phe Asp Arg Glu Ile Thr Pro Leu Tyr Asp
            20                  25                  30

Glu Arg Arg Asn Pro His Val Arg Asn Gly Thr Ile Ile Asp Phe Ser
        35                  40                  45

Ser Ser Lys Asp Glu Val Pro Thr Asp Val Lys Gln Thr Val Thr Asn
     50                  55                  60

Asn Leu Thr Val Met Tyr Arg Gln Met Ile Thr Asn Ala Ala Cys Pro
 65                  70                  75                  80

Leu Gln Phe Phe Gly Ala Arg Tyr Val Leu Gly Asn Asn Asn Met Asn
                85                  90                  95

Asp Arg Gly Thr Ile Glu Asn Ser Pro His Thr Pro Val His Ile Trp
            100                 105                 110

Ala Gly Thr Glu Gln Gly Ser Thr Phe Pro Asn Gly Asp Thr Ser Tyr
        115                 120                 125

Gly Glu Asp Met Gly Asn Phe Tyr Ser Ala Ala Leu Asp Pro Val Phe
    130                 135                 140

Tyr Ser His His Ala Asn Val Asp Arg Met Trp Asn Ile Trp Lys Gly
145                 150                 155                 160

Leu Gly Gly Lys Lys Lys Asp Ile Thr Asp Thr Asp Trp Leu Asn Ser
                165                 170                 175

Glu Phe Phe Phe Tyr Asp Glu
            180


<210> SEQ ID NO: 51
<211> LENGTH: 682
<212> TYPE: DNA
<213> ORGANISM: POTATO
<220> FEATURE:
<221> NAME/KEY: CDS
```

<222> LOCATION: (3)..(680)

<400> SEQUENCE: 51

```
tg cac tgt gcg tat tgt aac ggt gct tat aga att ggt ggc aaa gag        47
   His Cys Ala Tyr Cys Asn Gly Ala Tyr Arg Ile Gly Gly Lys Glu
     1               5                  10                  15

tta caa gtt cat aat tct tgg ctt ttc ttc ccg ttc cat aga tgg tac       95
Leu Gln Val His Asn Ser Trp Leu Phe Phe Pro Phe His Arg Trp Tyr
                 20                  25                  30

ttg tac ttc cac gag aga atc gtg gga aaa ttc att gat gat cca act      143
Leu Tyr Phe His Glu Arg Ile Val Gly Lys Phe Ile Asp Asp Pro Thr
             35                  40                  45

ttc gct tta cca tat tgg aat tgg gac cat cca aaa ggt atg cgt ttt      191
Phe Ala Leu Pro Tyr Trp Asn Trp Asp His Pro Lys Gly Met Arg Phe
         50                  55                  60

cct gcc atg tat gat cgt gaa ggg act tcc ctt ttc gat gta aca cgt      239
Pro Ala Met Tyr Asp Arg Glu Gly Thr Ser Leu Phe Asp Val Thr Arg
     65                  70                  75

gac caa agt cac cga aat gga gca gta atc gat ctt ggt ttt ttc ggc      287
Asp Gln Ser His Arg Asn Gly Ala Val Ile Asp Leu Gly Phe Phe Gly
 80                  85                  90                  95

aat gaa gtt gaa aca act caa ctc cag ttg atg agc aat aat tta aca      335
Asn Glu Val Glu Thr Thr Gln Leu Gln Leu Met Ser Asn Asn Leu Thr
                100                 105                 110

cta atg tac cgt caa atg gta act aat gct cca tgt cct cgg atg ttc      383
Leu Met Tyr Arg Gln Met Val Thr Asn Ala Pro Cys Pro Arg Met Phe
            115                 120                 125

ttt ggc ggg cct tat gat ctc ggg gtt aac act gaa ctc ccg gga act      431
Phe Gly Gly Pro Tyr Asp Leu Gly Val Asn Thr Glu Leu Pro Gly Thr
        130                 135                 140

ata gaa aac atc cct cac ggt cct gtc cac atc tgg tct ggt aca gtg      479
Ile Glu Asn Ile Pro His Gly Pro Val His Ile Trp Ser Gly Thr Val
    145                 150                 155

aga ggt tca act ttg ccc aat ggt gca ata tca aac ggt gag aat atg      527
Arg Gly Ser Thr Leu Pro Asn Gly Ala Ile Ser Asn Gly Glu Asn Met
160                 165                 170                 175

ggt cat ttt tac tca gct ggt ttg gac ccg gtt ttc ttt tgc cat cac      575
Gly His Phe Tyr Ser Ala Gly Leu Asp Pro Val Phe Phe Cys His His
                180                 185                 190

agc aat gtg gat cgg atg tgg agc gaa tgg aaa gcg aca gga ggg aaa      623
Ser Asn Val Asp Arg Met Trp Ser Glu Trp Lys Ala Thr Gly Gly Lys
            195                 200                 205

aga acg gat atc aca cat aaa gat tgg ttg aac tcc gag ttc ttt ttc      671
Arg Thr Asp Ile Thr His Lys Asp Trp Leu Asn Ser Glu Phe Phe Phe
        210                 215                 220

tat gac gaa aa                                                       682
Tyr Asp Glu
    225
```

<210> SEQ ID NO: 52
<211> LENGTH: 226
<212> TYPE: PRT
<213> ORGANISM: POTATO

<400> SEQUENCE: 52

```
His Cys Ala Tyr Cys Asn Gly Ala Tyr Arg Ile Gly Gly Lys Glu Leu
  1               5                  10                  15

Gln Val His Asn Ser Trp Leu Phe Phe Pro Phe His Arg Trp Tyr Leu
             20                  25                  30

Tyr Phe His Glu Arg Ile Val Gly Lys Phe Ile Asp Asp Pro Thr Phe
```

-continued

```
        35                  40                  45

Ala Leu Pro Tyr Trp Asn Trp Asp His Pro Lys Gly Met Arg Phe Pro
     50                  55                  60

Ala Met Tyr Asp Arg Glu Gly Thr Ser Leu Phe Asp Val Thr Arg Asp
 65                  70                  75                  80

Gln Ser His Arg Asn Gly Ala Val Ile Asp Leu Gly Phe Phe Gly Asn
                 85                  90                  95

Glu Val Glu Thr Thr Gln Leu Gln Leu Met Ser Asn Asn Leu Thr Leu
            100                 105                 110

Met Tyr Arg Gln Met Val Thr Asn Ala Pro Cys Pro Arg Met Phe Phe
        115                 120                 125

Gly Gly Pro Tyr Asp Leu Gly Val Asn Thr Glu Leu Pro Gly Thr Ile
    130                 135                 140

Glu Asn Ile Pro His Gly Pro Val His Ile Trp Ser Gly Thr Val Arg
145                 150                 155                 160

Gly Ser Thr Leu Pro Asn Gly Ala Ile Ser Asn Gly Glu Asn Met Gly
                165                 170                 175

His Phe Tyr Ser Ala Gly Leu Asp Pro Val Phe Phe Cys His His Ser
            180                 185                 190

Asn Val Asp Arg Met Trp Ser Glu Trp Lys Ala Thr Gly Gly Lys Arg
        195                 200                 205

Thr Asp Ile Thr His Lys Asp Trp Leu Asn Ser Glu Phe Phe Phe Tyr
    210                 215                 220

Asp Glu
225


<210> SEQ ID NO: 53
<211> LENGTH: 536
<212> TYPE: DNA
<213> ORGANISM: POTATO
<220> FEATURE:
<221> NAME/KEY: CDS
<222> LOCATION: (1)..(534)

<400> SEQUENCE: 53

ttg ccg tat tgg aat tgg gac cat cca aaa ggt atg cgt tta cct ccc       48
Leu Pro Tyr Trp Asn Trp Asp His Pro Lys Gly Met Arg Leu Pro Pro
  1               5                  10                  15

atg ttc gat cgt gaa act act ccc ctt tat gat gca aga cgt aat cca       96
Met Phe Asp Arg Glu Thr Thr Pro Leu Tyr Asp Ala Arg Arg Asn Pro
             20                  25                  30

cat gtc cgt aat gga acc ata atc gat ttt agt tct cct aga gac gaa      144
His Val Arg Asn Gly Thr Ile Ile Asp Phe Ser Ser Pro Arg Asp Glu
        35                  40                  45

gtt att act gat gtt gga caa acg gtg act aac aac tta act tta atg      192
Val Ile Thr Asp Val Gly Gln Thr Val Thr Asn Asn Leu Thr Leu Met
     50                  55                  60

tac cgt tca atg ata act aat gct gca tgc cct ttg caa ttc ttt ggt      240
Tyr Arg Ser Met Ile Thr Asn Ala Ala Cys Pro Leu Gln Phe Phe Gly
 65                  70                  75                  80

gct cgt tac gtc ctt ggg aat aac gat tcc aaa ggt cag gga act att      288
Ala Arg Tyr Val Leu Gly Asn Asn Asp Ser Lys Gly Gln Gly Thr Ile
                 85                  90                  95

gaa aac atc cct cat act ccg gtc cac ata tgg gct ggt act gta aga      336
Glu Asn Ile Pro His Thr Pro Val His Ile Trp Ala Gly Thr Val Arg
            100                 105                 110

aat acg gat ttg ggt ggt ggt aaa ctg tca tta ggt gaa gat atg ggt      384
Asn Thr Asp Leu Gly Gly Gly Lys Leu Ser Leu Gly Glu Asp Met Gly
```

-continued

```
        115                 120                 125

aat ttc tac tca gcc gct tta gac ccg gtt ttc tat tgc cac cac gcc      432
Asn Phe Tyr Ser Ala Ala Leu Asp Pro Val Phe Tyr Cys His His Ala
    130                 135                 140

aat gtg gac cga atg tgg aaa gta tgg aaa gga tta cgc ggg aaa aga      480
Asn Val Asp Arg Met Trp Lys Val Trp Lys Gly Leu Arg Gly Lys Arg
145                 150                 155                 160

agg gat atc ata gat cca gat tgg ttg aac tct gaa ttc ttt ttc tac      528
Arg Asp Ile Ile Asp Pro Asp Trp Leu Asn Ser Glu Phe Phe Phe Tyr
                165                 170                 175

gac gag aa                                                           536
Asp Glu
```

<210> SEQ ID NO: 54
<211> LENGTH: 178
<212> TYPE: PRT
<213> ORGANISM: POTATO

<400> SEQUENCE: 54

```
Leu Pro Tyr Trp Asn Trp Asp His Pro Lys Gly Met Arg Leu Pro Pro
  1               5                  10                  15

Met Phe Asp Arg Glu Thr Thr Pro Leu Tyr Asp Ala Arg Arg Asn Pro
             20                  25                  30

His Val Arg Asn Gly Thr Ile Ile Asp Phe Ser Ser Pro Arg Asp Glu
         35                  40                  45

Val Ile Thr Asp Val Gly Gln Thr Val Thr Asn Asn Leu Thr Leu Met
     50                  55                  60

Tyr Arg Ser Met Ile Thr Asn Ala Ala Cys Pro Leu Gln Phe Phe Gly
 65                  70                  75                  80

Ala Arg Tyr Val Leu Gly Asn Asn Asp Ser Lys Gly Gln Gly Thr Ile
                 85                  90                  95

Glu Asn Ile Pro His Thr Pro Val His Ile Trp Ala Gly Thr Val Arg
            100                 105                 110

Asn Thr Asp Leu Gly Gly Gly Lys Leu Ser Leu Gly Glu Asp Met Gly
        115                 120                 125

Asn Phe Tyr Ser Ala Ala Leu Asp Pro Val Phe Tyr Cys His His Ala
    130                 135                 140

Asn Val Asp Arg Met Trp Lys Val Trp Lys Gly Leu Arg Gly Lys Arg
145                 150                 155                 160

Arg Asp Ile Ile Asp Pro Asp Trp Leu Asn Ser Glu Phe Phe Phe Tyr
                165                 170                 175

Asp Glu
```

<210> SEQ ID NO: 55
<211> LENGTH: 515
<212> TYPE: DNA
<213> ORGANISM: POTATO
<220> FEATURE:
<221> NAME/KEY: CDS
<222> LOCATION: (1)..(513)

<400> SEQUENCE: 55

```
ttg ccg ttc tgg aat tgg gat cat cca aaa ggt atg cgt ata cct ccc       48
Leu Pro Phe Trp Asn Trp Asp His Pro Lys Gly Met Arg Ile Pro Pro
  1               5                  10                  15

atg ttt gat cgt gag ggg tca tct ctt tac gat gat aaa cgt aac caa       96
Met Phe Asp Arg Glu Gly Ser Ser Leu Tyr Asp Asp Lys Arg Asn Gln
             20                  25                  30
```

-continued

```
aac cat cgc aat gga act att att gat ctt ggt cat ttt ggt aag gaa       144
Asn His Arg Asn Gly Thr Ile Ile Asp Leu Gly His Phe Gly Lys Glu
        35                  40                  45

gtt gac aca cct cag ctc cag ata atg act aat aat tta aca cta atg       192
Val Asp Thr Pro Gln Leu Gln Ile Met Thr Asn Asn Leu Thr Leu Met
    50                  55                  60

tac cgt caa atg gtg act aat gct cct tgt ccg ccc caa ttc ttc ggt       240
Tyr Arg Gln Met Val Thr Asn Ala Pro Cys Pro Pro Gln Phe Phe Gly
65                  70                  75                  80

gct gct tac cct ctg ggg act aaa cca agt ccg gga atg ggt act att       288
Ala Ala Tyr Pro Leu Gly Thr Lys Pro Ser Pro Gly Met Gly Thr Ile
                85                  90                  95

gag aac atc cct cat acc ccg gtt cac atc tgg acc ggt gat aca cct       336
Glu Asn Ile Pro His Thr Pro Val His Ile Trp Thr Gly Asp Thr Pro
            100                 105                 110

aga caa aaa aac ggt gaa aac atg ggt aat ttc tat tca gcc ggt tta       384
Arg Gln Lys Asn Gly Glu Asn Met Gly Asn Phe Tyr Ser Ala Gly Leu
        115                 120                 125

gac ccg att ttt tac tgt cac cac gca aat gtg gac cgg atg tgg gat       432
Asp Pro Ile Phe Tyr Cys His His Ala Asn Val Asp Arg Met Trp Asp
    130                 135                 140

gaa tgg aaa tta att ggc ggg aaa aga agg gat cta tca aat aaa gat       480
Glu Trp Lys Leu Ile Gly Gly Lys Arg Arg Asp Leu Ser Asn Lys Asp
145                 150                 155                 160

tgg ttg aac tca gaa ttc ttt ttc tat gac gag aa                        515
Trp Leu Asn Ser Glu Phe Phe Phe Tyr Asp Glu
                165                 170
```

```
<210> SEQ ID NO: 56
<211> LENGTH: 171
<212> TYPE: PRT
<213> ORGANISM: POTATO

<400> SEQUENCE: 56

Leu Pro Phe Trp Asn Trp Asp His Pro Lys Gly Met Arg Ile Pro Pro
  1               5                  10                  15

Met Phe Asp Arg Glu Gly Ser Ser Leu Tyr Asp Asp Lys Arg Asn Gln
            20                  25                  30

Asn His Arg Asn Gly Thr Ile Ile Asp Leu Gly His Phe Gly Lys Glu
        35                  40                  45

Val Asp Thr Pro Gln Leu Gln Ile Met Thr Asn Asn Leu Thr Leu Met
    50                  55                  60

Tyr Arg Gln Met Val Thr Asn Ala Pro Cys Pro Pro Gln Phe Phe Gly
65                  70                  75                  80

Ala Ala Tyr Pro Leu Gly Thr Lys Pro Ser Pro Gly Met Gly Thr Ile
                85                  90                  95

Glu Asn Ile Pro His Thr Pro Val His Ile Trp Thr Gly Asp Thr Pro
            100                 105                 110

Arg Gln Lys Asn Gly Glu Asn Met Gly Asn Phe Tyr Ser Ala Gly Leu
        115                 120                 125

Asp Pro Ile Phe Tyr Cys His His Ala Asn Val Asp Arg Met Trp Asp
    130                 135                 140

Glu Trp Lys Leu Ile Gly Gly Lys Arg Arg Asp Leu Ser Asn Lys Asp
145                 150                 155                 160

Trp Leu Asn Ser Glu Phe Phe Phe Tyr Asp Glu
                165                 170

<210> SEQ ID NO: 57
```

-continued

<211> LENGTH: 25
<212> TYPE: DNA
<213> ORGANISM: Artificial Sequence
<220> FEATURE:
<223> OTHER INFORMATION: Description of Artificial Sequence: PRIMER

<400> SEQUENCE: 57
gcgaattctt yytnccntty caymg 25

<210> SEQ ID NO: 58
<211> LENGTH: 28
<212> TYPE: DNA
<213> ORGANISM: Artificial Sequence
<220> FEATURE:
<223> OTHER INFORMATION: Description of Artificial Sequence: PRIMER

<400> SEQUENCE: 58
gcgaattcga rgayatgggn aayttyta 28

<210> SEQ ID NO: 59
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 59
gcgaattcaa ygtngaymgn atgtgg 26

<210> SEQ ID NO: 60
<211> LENGTH: 28
<212> TYPE: DNA
<213> ORGANISM: Artificial Sequence
<220> FEATURE:
<223> OTHER INFORMATION: Description of Artificial Sequence: PRIMER

<400> SEQUENCE: 60
gcgaattcga tccnacntty gckttncc 28

<210> SEQ ID NO: 61
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 61
gcgaattctn caytgygcnt aytg 24

<210> SEQ ID NO: 62
<211> LENGTH: 27
<212> TYPE: DNA
<213> ORGANISM: Artificial Sequence
<220> FEATURE:
<223> OTHER INFORMATION: Description of Artificial Sequence: PRIMER

<400> SEQUENCE: 62
gcgaattctt nccntwytgg aaytggg 27

<210> SEQ ID NO: 63
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 63

-continued

```
gcctgcagcc acatnckrtc nacrtt                                     26


<210> SEQ ID NO: 64
<211> LENGTH: 22
<212> TYPE: DNA
<213> ORGANISM: Artificial Sequence
<220> FEATURE:
<223> OTHER INFORMATION: Description of Artificial Sequence: PRIMER

<400> SEQUENCE: 64

gcctgcagtt ytcrtcrtag aa                                         22


<210> SEQ ID NO: 65
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 65

gcctgcagay arctnccngc aaactc                                     26


<210> SEQ ID NO: 66
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 66

gcctgcagtc ytcnarnarn tcng                                       24
```